US009694082B2

(12) United States Patent
Kaplan et al.

(10) Patent No.: US 9,694,082 B2
(45) Date of Patent: Jul. 4, 2017

(54) PH INDUCED SILK GELS AND USES THEREOF

(71) Applicant: TRUSTEES OF TUFTS COLLEGE, Medford, MA (US)

(72) Inventors: David L. Kaplan, Concord, MA (US); Tuna Yucel, Medford, MA (US); Tim Jia-Ching Lo, Medford, MA (US); Gary G. Leisk, Wilmington, MA (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 13/933,611

(22) Filed: Jul. 2, 2013

(65) Prior Publication Data
US 2014/0134240 A1  May 15, 2014

Related U.S. Application Data

(63) Continuation of application No. 12/974,796, filed on Dec. 21, 2010, now Pat. No. 8,501,172, which is a continuation-in-part of application No. PCT/US2009/058534, filed on Sep. 28, 2009.

(60) Provisional application No. 61/100,352, filed on Sep. 26, 2008, provisional application No. 61/156,976, filed on Mar. 3, 2009.

(51) Int. Cl.
| | |
|---|---|
| *A61K 39/395* | (2006.01) |
| *A61K 47/42* | (2017.01) |
| *A61L 27/22* | (2006.01) |
| *A61L 27/34* | (2006.01) |
| *A61L 27/36* | (2006.01) |
| *A61L 27/38* | (2006.01) |
| *A61L 27/52* | (2006.01) |
| *H01L 41/193* | (2006.01) |
| *A61K 9/10* | (2006.01) |
| *A61K 41/00* | (2006.01) |
| *A61L 26/00* | (2006.01) |

(52) U.S. Cl.
CPC ............... *A61K 47/42* (2013.01); *A61K 9/10* (2013.01); *A61K 41/00* (2013.01); *A61L 26/0047* (2013.01); *A61L 27/227* (2013.01); *A61L 27/34* (2013.01); *A61L 27/3604* (2013.01); *A61L 27/38* (2013.01); *A61L 27/52* (2013.01); *H01L 41/193* (2013.01)

(58) Field of Classification Search
CPC .................................................... A61K 39/395
USPC ................................................ 514/773, 18.6
See application file for complete search history.

(56) References Cited

U.S. PATENT DOCUMENTS

| | | | |
|---|---|---|---|
| 1,989,005 | A | 1/1935 | Fink et al. |
| 4,233,212 | A | 11/1980 | Otoi et al. |
| 4,820,418 | A | 4/1989 | Hirotsu et al. |
| 5,047,507 | A | 9/1991 | Buchegger et al. |
| 5,290,494 | A | 3/1994 | Coombes et al. |
| 5,606,019 | A | 2/1997 | Cappello |
| 5,728,810 | A | 3/1998 | Lewis et al. |
| 5,770,193 | A | 6/1998 | Vacanti et al. |
| 6,110,590 | A | 8/2000 | Zarkoob et al. |
| 6,175,053 | B1 | 1/2001 | Tsubouchi |
| 6,592,623 | B1 | 7/2003 | Bowlin et al. |
| 6,815,427 | B2 | 11/2004 | Tsubouchi et al. |
| 6,902,932 | B2 | 6/2005 | Altman et al. |
| 7,041,797 | B2 | 5/2006 | Vollrath |
| 7,057,023 | B2 | 6/2006 | Islam et al. |
| 7,285,637 | B2 | 10/2007 | Armato et al. |
| 7,635,755 | B2 | 12/2009 | Kaplan et al. |
| 7,662,409 | B2 | 2/2010 | Masters |
| 7,674,882 | B2 | 3/2010 | Kaplan et al. |
| 7,727,575 | B2 | 6/2010 | Kaplan et al. |
| 7,842,780 | B2 | 11/2010 | Kaplan et al. |
| 8,361,617 | B2 * | 1/2013 | Kaplan et al. ................ 428/357 |
| 2003/0183978 | A1 | 10/2003 | Asakura |
| 2004/0005363 | A1 | 1/2004 | Tsukada et al. |

(Continued)

FOREIGN PATENT DOCUMENTS

| | | |
|---|---|---|
| CA | 2405850 | 10/2002 |
| EP | 1440088 | 7/2004 |

(Continued)

OTHER PUBLICATIONS

Terry et al., "pH induced changes in the rheology of silk fibroin solution from the middle division of *Bombyx mori* silkworm", Biomacromolecules, 2004, pp. 768-772, vol. 5.
Packham, "Work of adhesion: contact angles and contact mechanics", International Journal of Adhesion and Adhesives, 1996, pp. 121-128, vol. 16.
Ando, Y., "Piezoelectric and related properties of hydrated silk fibroin." Reports on Progress in Polymer Physics, in Japan, XXIII:775-778 (1980).
Altman, G.H. et al., 2003. Silk-based biomaterials. Biomaterials 24 (3), 401-416.
Jin, H.-J., et al. (2005) Water-Stable Silk Films with Reduced Beta-Sheet Content. Adv. Funct. Matter 15, 1241-1247.

(Continued)

*Primary Examiner* — Maryam Monshipouri
(74) *Attorney, Agent, or Firm* — Choate, Hall & Stewart LLP

(57) ABSTRACT

This invention provides for compositions, methods and devices for rapidly converting silk fibroin solution into a silk fibroin gel using direct application of voltage, in a process called electrogelation. The silk fibroin gel may be reversibly converted back to liquid form by applying reverse voltage or may be converted further to β-sheet structure by applying shear force or other treatments. The electrogelated silk may be used as an extracted bulk gel, spray or stream of gel for processing into materials or devices, or may be used as silk gel coating to devices. Active agents may be embedded in the silk gel for various medical applications. This invention also provides for methods and compositions for preparing adhesive silk pH-gels. For example, the method comprises reducing pH level of a silk fibroin solution to increase the bulk or local proton concentration of the silk fibroin solution, thereby forming adhesive silk gels.

8 Claims, 30 Drawing Sheets

(56) References Cited

U.S. PATENT DOCUMENTS

| | | |
|---|---|---|
| 2004/0266992 A1 | 12/2004 | Migliaresi et al. |
| 2005/0260706 A1 | 11/2005 | Kaplan et al. |
| 2007/0187862 A1 | 8/2007 | Kaplan et al. |
| 2007/0212730 A1 | 9/2007 | Vepari et al. |
| 2008/0085272 A1 | 4/2008 | Kaplan et al. |
| 2008/0293919 A1 | 11/2008 | Kaplan et al. |
| 2009/0171467 A1 | 7/2009 | Mann et al. |
| 2009/0202614 A1 | 8/2009 | Kaplan et al. |
| 2009/0232963 A1 | 9/2009 | Kaplan et al. |
| 2009/0234026 A1 | 9/2009 | Kaplan et al. |
| 2009/0297588 A1 | 12/2009 | Rheinnecker et al. |
| 2010/0028451 A1 | 2/2010 | Kaplan et al. |
| 2010/0046902 A1 | 2/2010 | Kaplan et al. |
| 2010/0055438 A1 | 3/2010 | Kaplan et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0095827 A1 | 4/2010 | Rheinnecker et al. |
| 2010/0096763 A1 | 4/2010 | Kaplan et al. |
| 2010/0120116 A1 | 5/2010 | Kaplan et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0279112 A1 | 11/2010 | Kaplan et al. |
| 2010/0292338 A1 | 11/2010 | Rheinnecker et al. |
| 2011/0046686 A1 | 2/2011 | Kaplan et al. |
| 2011/0076384 A1 | 3/2011 | Cannizzaro et al. |
| 2011/0121485 A1 | 5/2011 | Rheinnecker et al. |
| 2011/0135697 A1 | 6/2011 | Omenetto et al. |
| 2011/0152214 A1 | 6/2011 | Boison et al. |
| 2011/0171239 A1 | 7/2011 | Kaplan et al. |
| 2012/0121820 A1 | 5/2012 | Kaplan et al. |
| 2012/0123519 A1 | 5/2012 | Lovett et al. |

FOREIGN PATENT DOCUMENTS

| | | |
|---|---|---|
| JP | 58-38449 | 8/1983 |
| JP | 60-259677 | 12/1985 |
| JP | 01-118544 | 5/1989 |
| JP | 04-263611 | 9/1992 |
| JP | 06-346314 | 12/1994 |
| JP | 08-295697 | 11/1996 |
| JP | 10-36676 | 2/1998 |
| JP | 2000273264 | 10/2000 |
| JP | 2004068161 | 3/2004 |
| WO | 99/01089 | 1/1999 |
| WO | 01/36531 | 5/2001 |
| WO | 01/56626 | 8/2001 |
| WO | 02/072931 | 9/2002 |
| WO | 03/022909 | 3/2003 |
| WO | 2004/041845 | 5/2004 |
| WO | 2005/012606 | 2/2005 |
| WO | 2008/150861 | 12/2008 |
| WO | 2009/156226 | 12/2009 |
| WO | 2011/006133 | 1/2011 |

OTHER PUBLICATIONS

Horan, R.L. et al., 2005. In vitro degradation of silk fibroin. Biomaterials 26 (17), 3385-3393.

Jin, H.J., Mechanism of silk processing in insects and spiders. Nature 424, 1057-1061, 2003.

Kim, U.J. et al., 2004. Structure and properties of silk hydrogels. Biomacromolecules 5, 786-792.

Li, et al. (2006) Electrospun Silk-BMP-2 Scaffolds for Bone Tissue Engineering, Biomaterials 27, 3115-3124.

Sofia, S., et al., Functionalized silk-based biomaterials for bone formation. Journal of Biomedical Materials Research, 2001, 54(1): 139-48.

Nazarov, R. et al., Porous 3-D scaffolds from regenerated silk fibroin. Biomacromolecules 5, 718-726, 2004.

Asakura et al., Conformational Characterization of B. Mori Silk Fibroin in the Solid State by High-Frequency 13C Cross Polarization-Magic Angel Spinning NMR, X-Ray Diffraction and Infrared Spectroscopy, Macromolecules, 18:1841-1845 (1985).

Chen et al., pH Sensitivity and Ion Sensitivity of Hydrogels Based on Complex-Forming Chitosan/Silk Fibroin Interpenetrating Polymer Network, J Appl Polymer Sci, 65:2257-2262 (1997).

Chen, X. et al., "Conformation Transition Kinetics of *Bombyx mori* Silk Protein" Proteins: Structure, Function, and Bioinformatics 68:223-231 (2007).

Database WPI Week 198205, Derwent Publications Ltd., London, GB; AN 1982-09092E & JP 56 166235 A, 12-21 1981 Abstract.

Demura et al., "Porous Membrane of *Bombyx mori* silk fibroin: structure characterization, physical properties and application to glucose oxidase immobilization", J. Membrane Science 59:39-52 (1991).

Demura et al., Immobilization of Biocatalysts with *Bombyx mori* Silk Fibroin by Several Kinds of Physical Treatment and its Application to Glucose Sensors, Biosensors 1989, 4: 361-372.

Doshi et al., Electrospinning Process and Applications of Electrospun Fibers, J. Electrostatics, 35: 151-160 (1995).

Huang et al., Generation of Synthetic Elastin-Mimetic Small Diameter Fibers and Fiber Networks, Macromolecules, 33:2989-2997 (2000).

Huang et al., Engineered collagen-PEO nanofibers and fabrics, J Biomater Sci Polymer Edn, 12(9):979-993 (2001).

Jin, et al., Electrospinning *Bombyx mori* Silk with Poly(ethlene oxide), Biomacromolecules 2002, 3: 1233-1239.

Kweon et al., Preparation of Semi-Interpenetrating Polymer Networks Composed of Silk Fibroin and Poly(ethylene glycol) Macromer, J. Appl Polymer Sci, 80; 1848-1853 (2001).

Lazaris et al., Spider silk fibers spun from soluble recombinant silk produced in mammalian cells, Science, 295: 472-476 (2002).

Liang et al., Improvements of the Physical Properties of Fibroin Membranes with Sodium Alginate, J. Appl Polymer Sci, 45:1937-1943 (1992).

Reneker et al., Nanometer Diameter Fibers of Polymer, Produced by Electrospinning, Nanotechnology, 7:216-223 (1996).

Cheng et al., Biomaterials, 29(22):3278-3288 (2008). "An electrochemical fabrication process for the assembly of an isotropically oriented collagen bundles."

Motta et al., Macromolecular Chemistry and Physics, 203(10-11):1658-1665 (2002). "Regenerated silk fibroin films: thermal and dynamic mechanical analysis."

Oui and Park, Adv Drug Deliv Rev, 53:321-329 (2001).

Servoli et al., Macromolecular Bioscience, 8(9):827-835 (2008). "Folding and assembly of fibroin driven by an AC electric field: effects on film properties."

\* cited by examiner

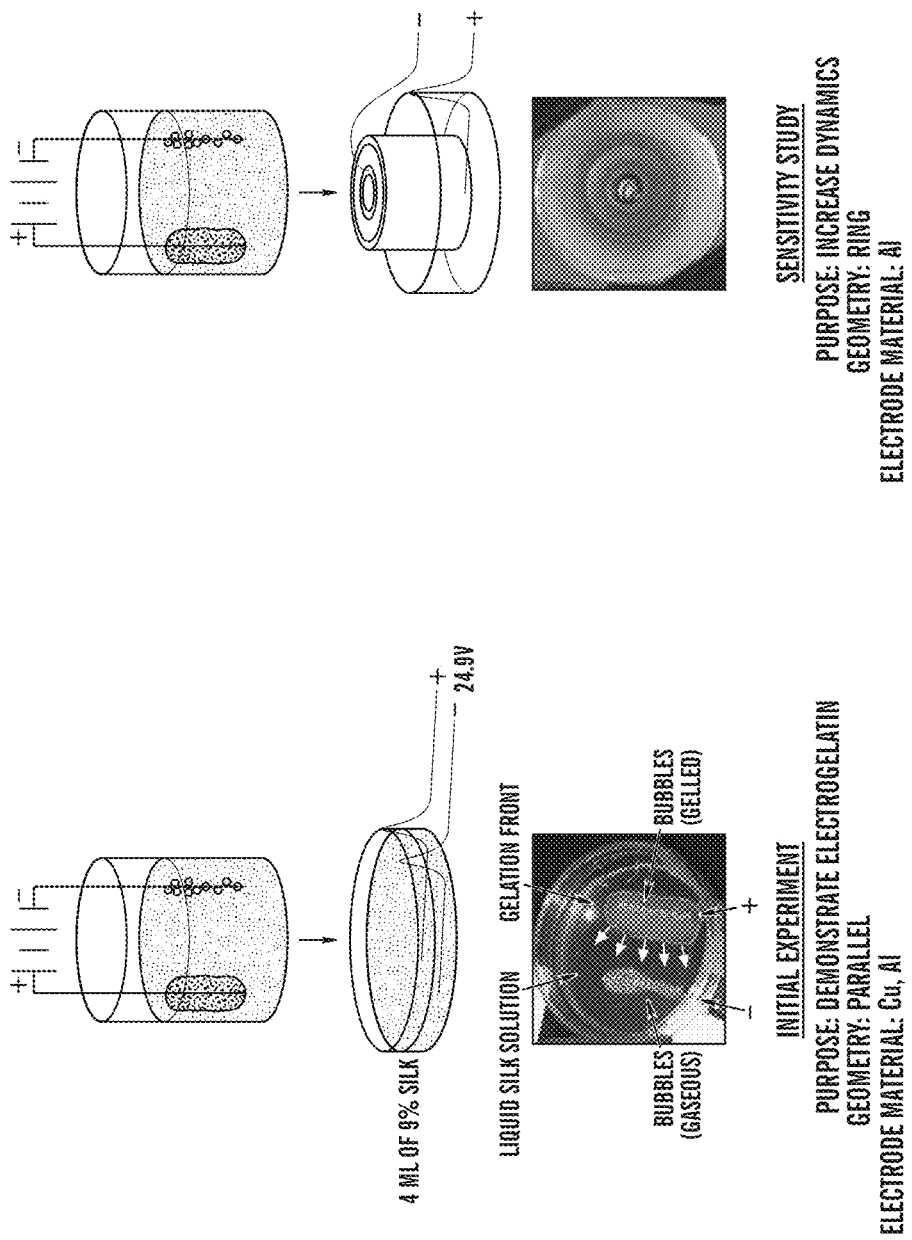

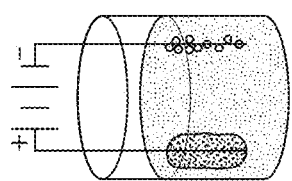 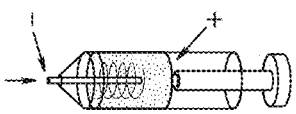 
FIG. 1D
APPLICATION EXPLORATION
PURPOSE: PRODUCT DEVELOPMENT
GEOMETRY: COIL
ELECTRODE MATERIAL: Al, STAINLESS STEEL, Pt
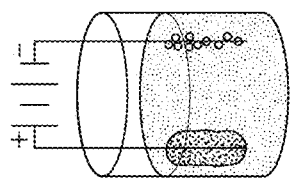 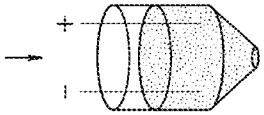 
FIG. 1C
FUNDAMENTAL STUDY
PURPOSE: SCIENTIFIC INVESTIGATION
GEOMETRY: PARALLEL
ELECTRODE MATERIAL: PENCIL LEAD, Pt

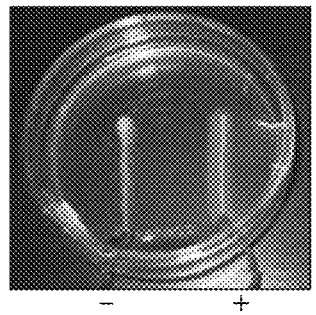
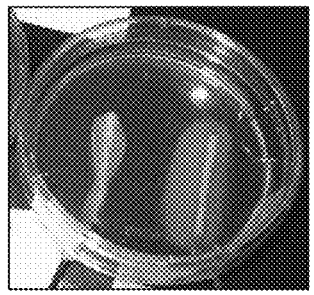
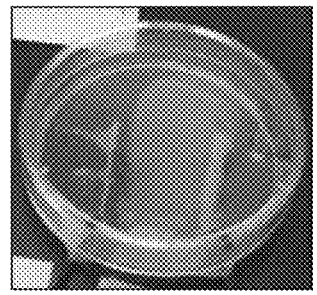
FIG. 5A  FIG. 5B  FIG. 5C
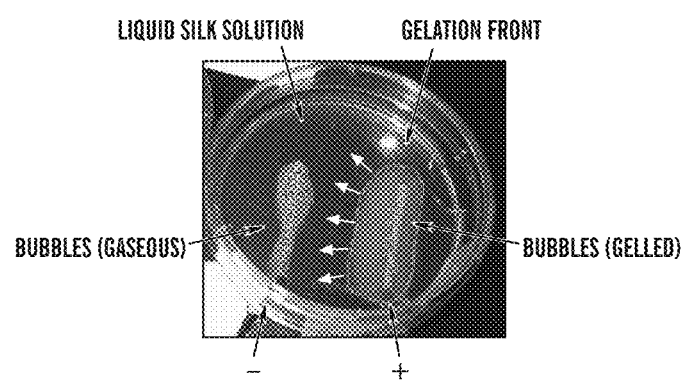
FIG. 6
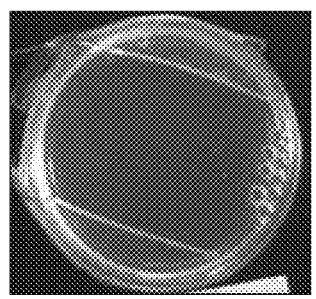
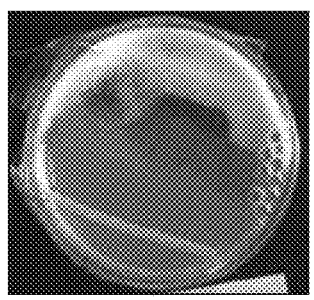
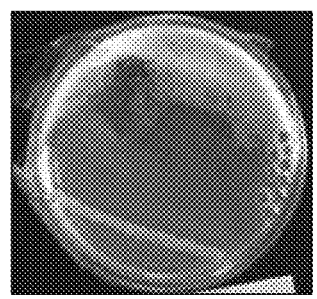
FIG. 7A  FIG. 7B  FIG. 7C

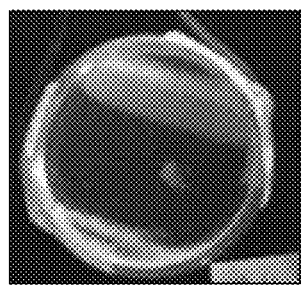 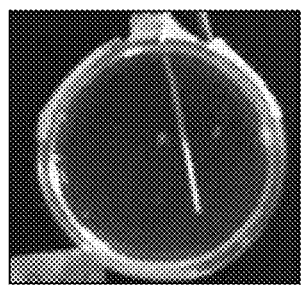 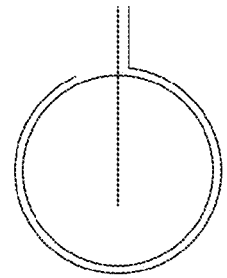
FIG. 8A　　FIG. 8B　　FIG. 8C
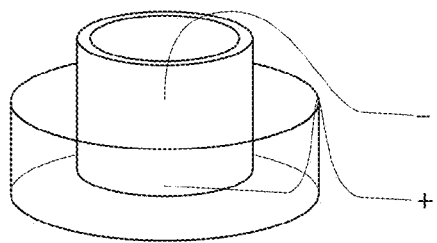 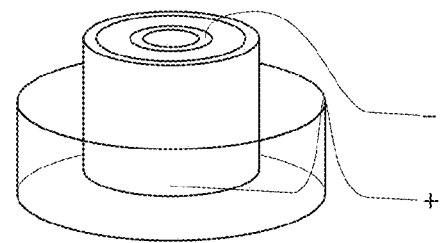
FIG. 9A　　　　FIG. 9B
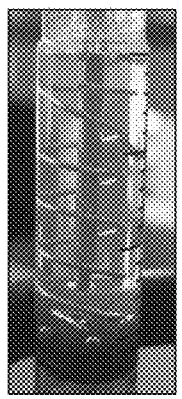 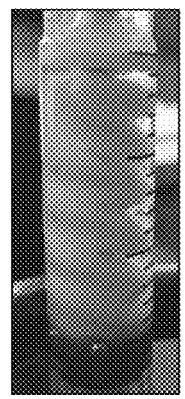 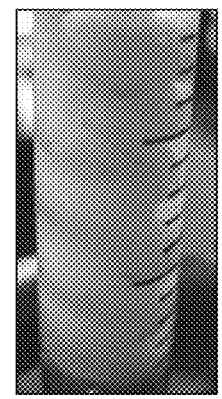
FIG. 10A　　FIG. 10B　　FIG. 10C

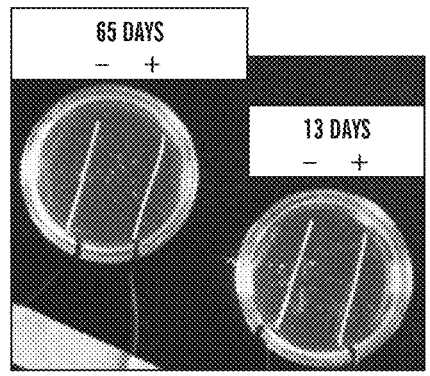 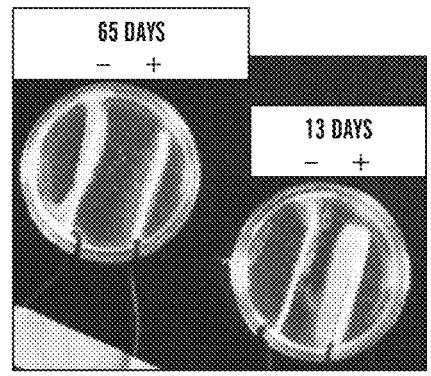
FIG. 11A  FIG. 11B
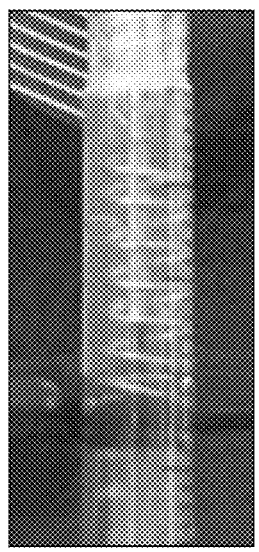 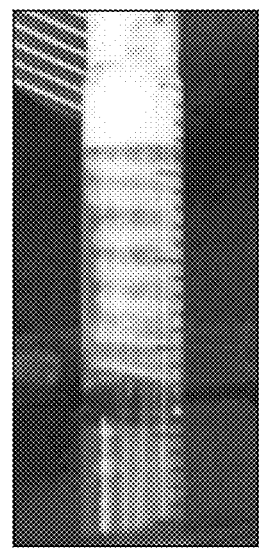 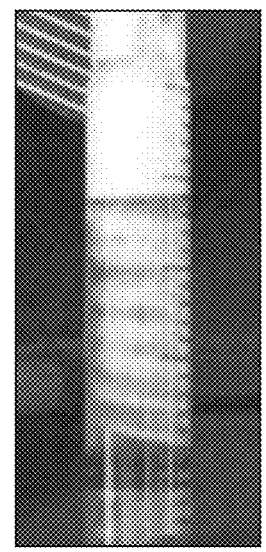
FIG. 12A  FIG. 12B  FIG. 12C

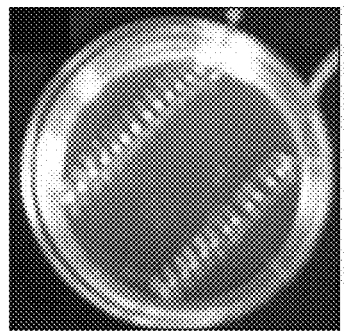 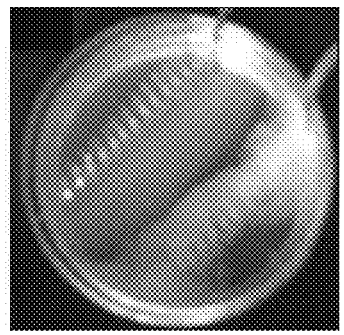 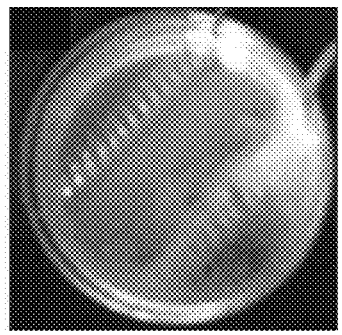
*FIG. 13A*     *FIG. 13B*     *FIG. 13C*
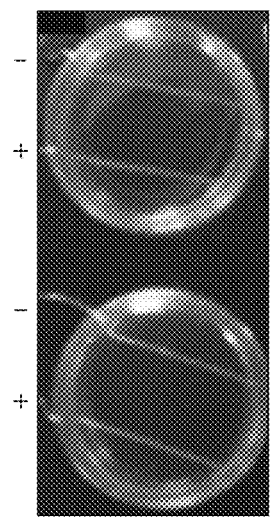 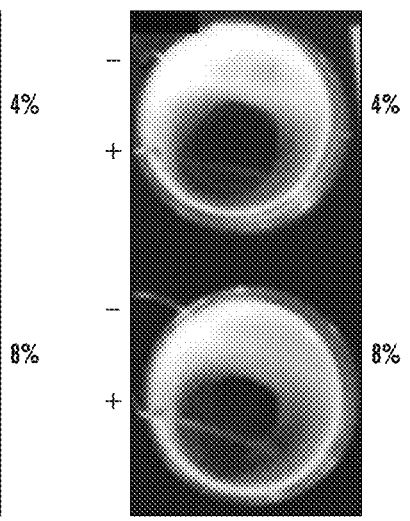 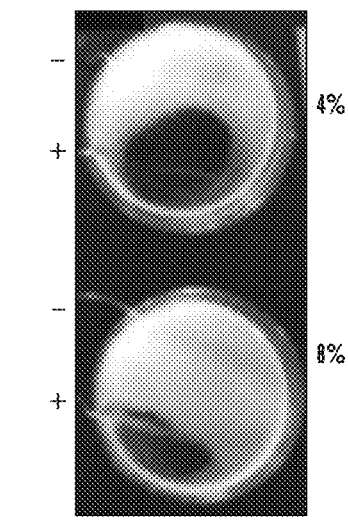
*FIG. 14A*     *FIG. 14B*     *FIG. 14C*

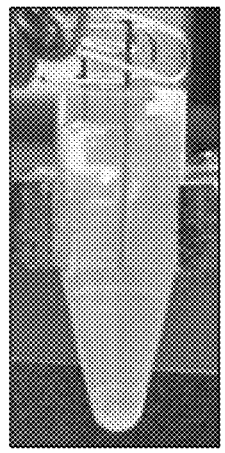 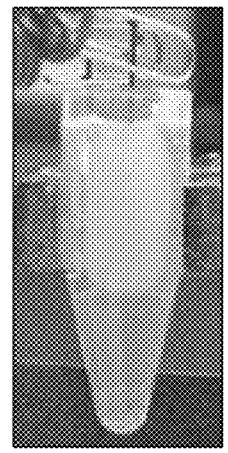 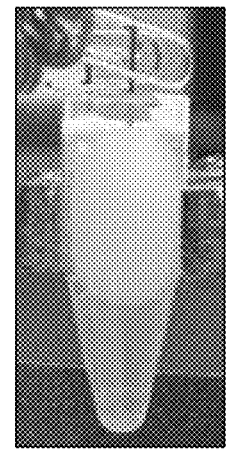
*FIG. 15A*     *FIG. 15B*     *FIG. 15C*
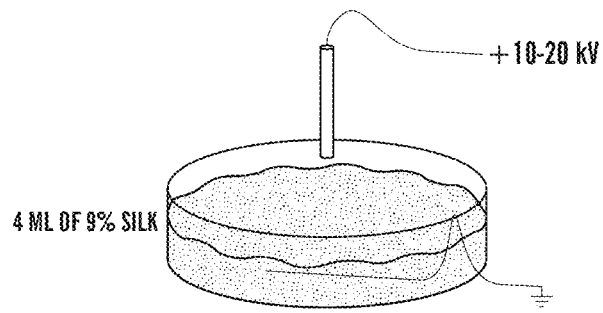
*FIG. 16*
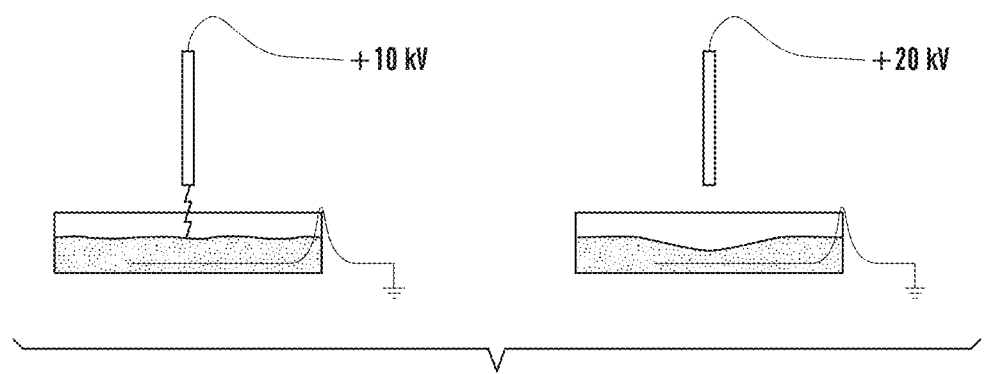
*FIG. 17*

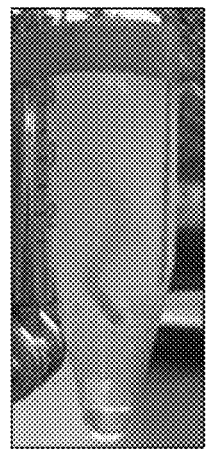 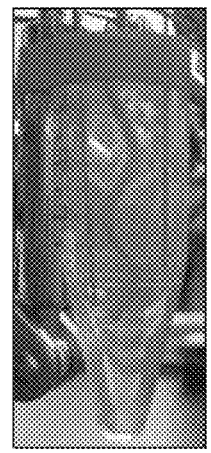
FIG. 18A  FIG. 18B
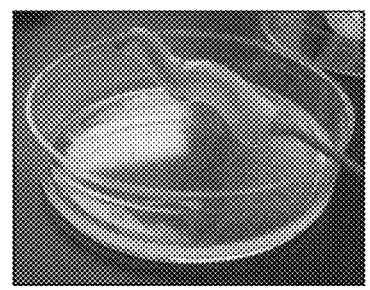
FIG. 18C
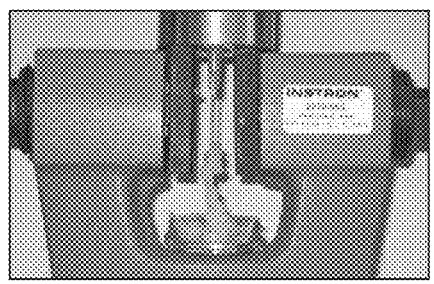 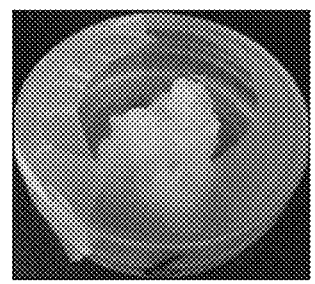
FIG. 19A  FIG. 19B

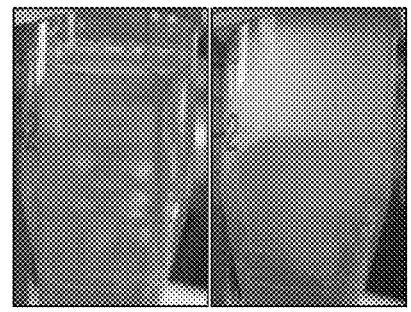
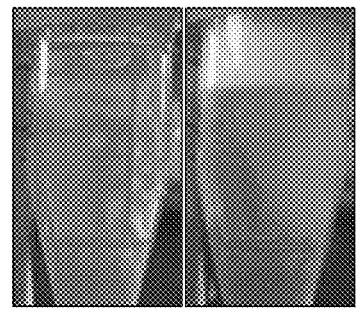
*FIG. 20A*          *FIG. 20B*
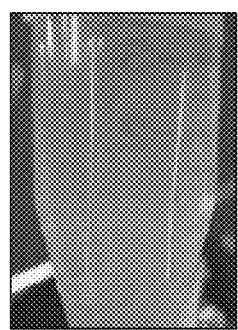
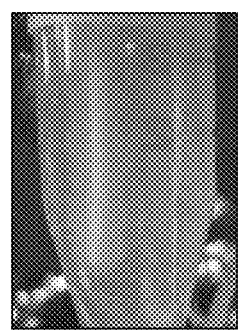
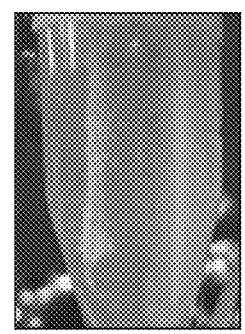
*FIG. 21A*     *FIG. 21B*     *FIG. 21C*

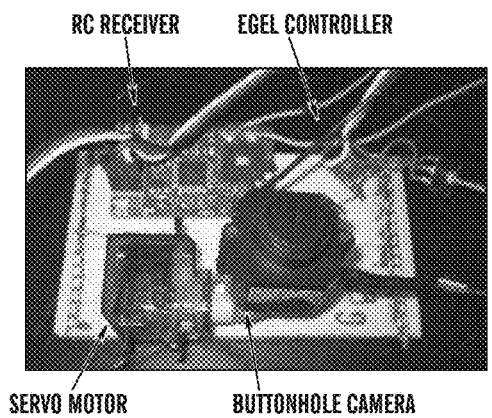 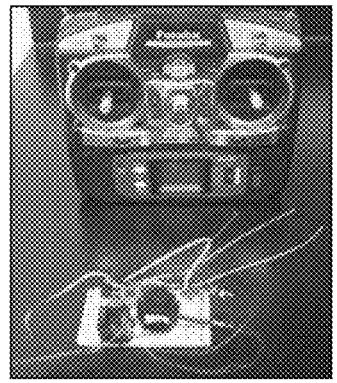
*FIG. 26A*   *FIG. 26B*
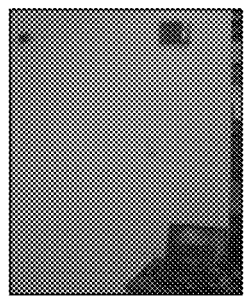 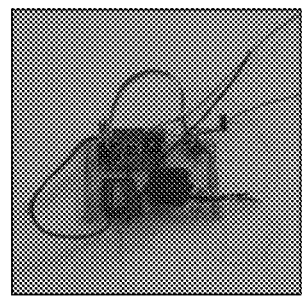 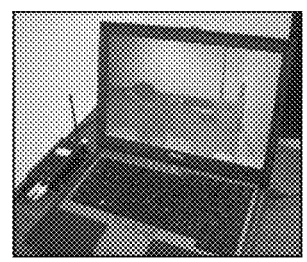
*FIG. 27A*   *FIG. 27B*   *FIG. 27C*

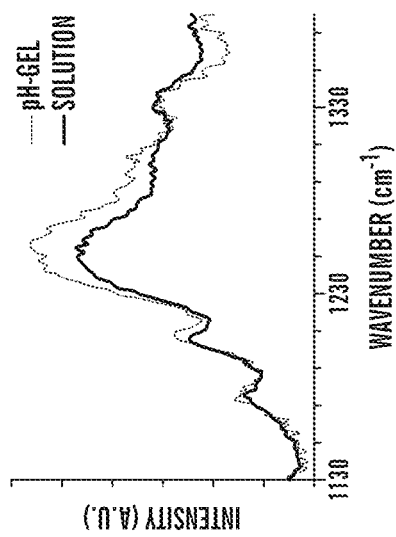
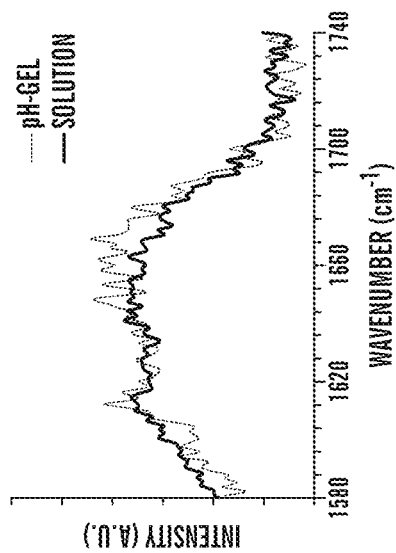
FIG. 35B
FIG. 35A

PH INDUCED SILK GELS AND USES THEREOF

CROSS REFERENCE TO RELATED APPLICATIONS

This application is a continuation of co-pending U.S. patent application Ser. No. 12/974,796 filed on Dec. 21, 2010, which is a continuation-in-part of PCT Application No. PCT/US2009/058534 filed on Sep. 28, 2009, which claims benefit under 35 U.S.C. §119(e) of U.S. Provisional Patent Application No. 61/100,352 filed on Sep. 26, 2008, and U.S. Provisional Patent Application No. 61/156,976 filed on Mar. 3, 2009, the contents of each of which are incorporated herein by reference in their entireties.

GOVERNMENT SUPPORT

This invention was made with government support under EB002520 awarded by the National Institutes of Health, under FA9550-07-1-0079 awarded by the U.S. Air Force, and under W911SR-08-C-0012 awarded by the U.S. Army Research, Development and Engineering Command Acquisition Center. The U.S. government has certain rights in the invention.

FIELD OF THE INVENTION

The present invention provides for methods and devices for rapidly and reversibly converting silk fibroin solution into a gel by applying an electric field. The invention also relates to methods and compositions for preparing adhesive silk gels.

BACKGROUND

Silk is generally defined as protein polymers spun into fibers by some Lepidoptera larvae such as silk worms and spiders. Silk is an intriguing biomaterial because of its light weight, incredible strength, and elasticity. The major components of silkworm *Bombyx mori* silk are fibroin protein and glue-like sericin protein. Silk fibroin protein compositions are attractive in biomedical applications, such as tissue engineering, because of their biocompatibility, slow degradability, and excellent mechanical properties. Degradable silk fibroin formulations offer mechanically robust materials for a wide range of mechanical and functional properties for biomedical applications including drug delivery. Among the useful silk fibroin preparations are silk gels. There remains a need for additional approaches to forming silk gels for a variety of applications.

SUMMARY OF THE INVENTION

The embodiments of the present invention provide for methods of reversibly converting solubilized silk fibroin solution into a silk fibroin gel by applying an electric field to the silk fibroin solution in a process called electrogelation. Applying an electric field to the solubilized silk fibroin solution may be performed, for example, by submerging electrodes in a solution of solubilized silk fibroin and applying a constant voltage across the electrodes. The electric field created by the voltage causes a conformational change of the silk fibroin from random coil to the silk I formation. Although voltages of up to about 50 VDC are effective in inducing gelation, higher voltages may be useful. In general, unless the silk fibroin solution has additional additives such as salt that reduce its electrical resistance, the voltage application may be performed at low current. In testing below about 50 VDC, the typical current is below about 10 milliamps. With the addition of salt to the solubilized silk fibroin solution, however, the current is increased dramatically, above about 80 milliamps, accompanied by increased gelation rates. When the DC voltage is reversed (reversal of the electrode polarity), the silk gel tends to convert back to a liquid form (random coil conformation).

Electrogelation has advantages over other mechanisms of inducing silk gelation, such as pH manipulation, heating, application of various ions and mechanical shearing, for several reasons. For example, an increase in the meta-stable silk I conformation of the silk fibroin achieved with electrogelation provides a more versatile material phase compared with β-sheet conformation generated by other gelation techniques. Additionally, the silk I structures exhibited in gel form can be transformed back to liquid form (random coil form); or through minimal additional molecular alignment, can be converted to β-sheet structures. This ability is an important characteristic of "smart structures."

Electrogelation can also be applied using a wide range of electrode materials and geometries, from platinum wire electrodes to mating metal plates to tissues (in vitro or in vivo) that can be coated with silk gel. Because a simple voltage need be applied, for example DC voltage from a battery-operated device, as opposed to other chemical manipulations, the process may be more benign in biomedical applications where living cells might be impacted.

An aspect of the present invention also provides for a piezoelectric silk material comprising a mixture of silk fibroin proteins having silk I conformation and silk β-sheet structure. The piezoelectric property of this silk material is characterized by the ratio of silk I conformation and silk β-sheet structure, which can be determined by the applying the methods presented herein. For example, the content of silk I conformation is adjusted by DC voltage and the content of silk β-sheet structure is effected by treating the electrogelated silk with dehydration, mechanical force, or thermodynamic treatment.

Additionally, various processing and delivery devices can be envisioned easily with electrogelation. A device has been created, as described herein, that processes and delivers electrogelated silk for biomedical and non-biomedical applications where either slow large-volume delivery, or fast spray and coating delivery is desired.

The electrogelation approach described herein has tremendous potential in various application areas, from toys to firefighting to medical procedures. The process itself is easy to implement, with various manifestations envisioned.

For example, one embodiment provides for a hand-held dispenser that allows a child to safely eject a rapid stream of electrogelated silk gel. This silk gel is edible, and can be flavored or colored, and also has the ability to stick to walls but remains biodegradable; features that make it an attractive alternative to the SILLY STRING® party novelty.

Silk gel generated by an electrogelation process of the present invention may also be used as biodegradable and biocompatible coatings on tissues or regenerated tissues (in vivo or in vitro) or medical devices such as medical implants. Such biodegradable and biocompatible implant coatings are of clinical interest due to their ability of continuously eluting desired drugs (e.g. anti inflammatory medication or growth factors) to the surrounding tissue of the implant.

Another embodiment provides for a hand-held device having a replaceable cartridge of silk solution. The cartridge may also contain specific cells or bioactive molecules that may be entrained in the silk solution. In the hands of a surgeon, silk gel can be ejected from the device in a coherent, slowly extruded stream to fill void space. In tissue reconstruction, for example, the gelated silk could be used to fill voids and encourage tissue growth.

Another embodiment provides for "soft robotics" in which the reversible electrogelation of silk solution provides a means of motion associated technology (e.g., camera). In particular, silk fibroin solution is not sticky, while silk gel is. This mucoadhesion characteristic mimics other natural mucoadhesives such as snail slime.

Another aspect of the invention relates to methods and compositions for preparing silk pH-gels.

In one embodiment, provided herein is a method of preparing a composition comprising a silk-based gel. The method comprises reducing pH level of a silk fibroin solution. Silk pH-gels herein can include silk gels that are induced by reducing pH, for example, either due to direction pH titration or due to indirect pH change, for instance, due to the electrolysis by electrogelation process described herein, thereby resulting increased proton concentration of silk fibroin solution, either locally or in bulk solution.

In one embodiment, the adhesive silk pH-gel is formed by reducing the local pH or bulk pH of the silk fibroin solution to an acidic pH. The step of reducing pH of the silk fibroin solution can comprise electrolyzing the silk fibroin solution to locally increase the proton concentration of the silk fibroin thereby forming the adhesive. The step of reducing pH of the silk fibroin solution can also comprise titrating the silk fibroin solution with an acid to an acid pH.

The adhesive silk pH-gel of the invention has an enhanced viscoelastic property that can provide an intimate contact with a surface of a subject and physically or chemically interact with a component of the subject, thereby adhering to the subject by forming a bonded interface with the subject.

Some embodiments of the invention also provide methods of attaching or adhering an adhesive silk-based gel to a surface of a subject. The method comprises exposing the subject to a silk fibroin solution; and reducing pH level of the silk fibroin solution thereby forming an adhesive comprising silk-based gel, wherein the silk-based gel adheres to the subject. The subject can be any subject needs to be adhered to, such as a biological tissue or organ, or anything that presents a mucosal surface.

The adhesive silk pH-gel can also comprise one or more active agents, and can be used in applications such as biodelivery and storage device, medical device, medical implants, tissue sealants, and tissue repairs such as wound dressing, biomimetic dynamic adhesive device, such as a surveillance platform containing the adhesive silk gels, cosmetic compositions, and cosmetic surgery materials.

BRIEF DESCRIPTION OF THE DRAWINGS

FIGS. 1A-1D present a schematic of electrogelation processes.

FIGS. 5A-5C show images of parallel electrode electrogelation experiment after 0 min, 20 min and 275 min of 22.2 VDC application.

FIG. 6 illustrates the silk fibroin solution electrogelation process.

FIGS. 7A-7C show images of parallel electrode electrogelation experiment after 0 min, 15 min, and 30 min of 74.9 VDC application.

FIGS. 8A-8C depict a comparison of parallel and ring electrode setups after 30 min exposure at 24.8 VDC.

FIGS. 9A-9B show a schematic of individual and dual aluminum tube electrode setups.

FIGS. 10A-10C show the results of syringe-based (3 ml) electrogelation utilizing spring-shaped electrode after 0 min, 5 min, and 15 min.

FIGS. 11A-11B show a comparison of electrogelation outcomes between 13-day-old and 65-day-old solubilized silk after 0 min and 10 min of 24.8 VDC voltage application.

FIGS. 12A-12C show the results of syringe-based (3 ml) electrogelation utilizing spring-shaped electrode after 0 min, 5 min, and 10 min of 24.8 VDC voltage application.

FIGS. 13A-13C depict electrogelation using parallel copper coil electrodes after 0 min, 5 min, and 10 min of 24.8 VDC voltage application.

FIGS. 14A-14C show the results of electrogelation of 4% and 8% solubilized silk with salt and DMEM using parallel electrode geometry with gelation times of 0 min, 5 min, and 10 min at 24.8 VDC voltage.

FIGS. 15A-15C show the electrogelation of solubilized silk at 24.8 VDC voltage using graphite electrodes.

FIG. 16 is a drawing of a high voltage electrogelation setup.

FIG. 17 is a schematic of high voltage electrogelation results.

FIGS. 18A-18C show a mixing-electrogelation device having two electrodes with auger between them, and gelation outcome.

FIGS. 19A-19B show the Instron® materials testing device (Grove City, Pa.) setup for extrusion, and a representative outcome.

FIGS. 20A and 20B are before and after photographs of platinum electrode gelations with silk solution and DMEM.

FIGS. 21A-21C show the results after reversing the electrode polarity such that the silk gel returns to liquid form.

FIGS. 26A and 26B show components of a surveillance platform that is mobilized by silk electrogelation.

FIGS. 27A-27C show images from the testing of the surveillance platform.

FIGS. 35A-35B are graphs showing the Raman spectra collected from silk solution and pH-gels in amide I region (FIG. 35A) and amide III region (FIG. 35B).

FIG. 37A show the change in elastic (G') and loss modulus (G") with incrementally increasing electrical field (1 V/mm/min). FIG. 37B shows the frequency sweeps collected from the e-gel (E=9 V/mm) and the pH-gel ([H+]=0.03 M). E-gel and pH-gel data are denoted by squares and triangles, respectively. FIG. 37C shows the time evolution of viscoelastic properties at different electric field strengths. FIG. 37D shows the time evolution of elastic modulus, normal force and current at 9 V/mm applied field.

DETAILED DESCRIPTION

Figure 2:
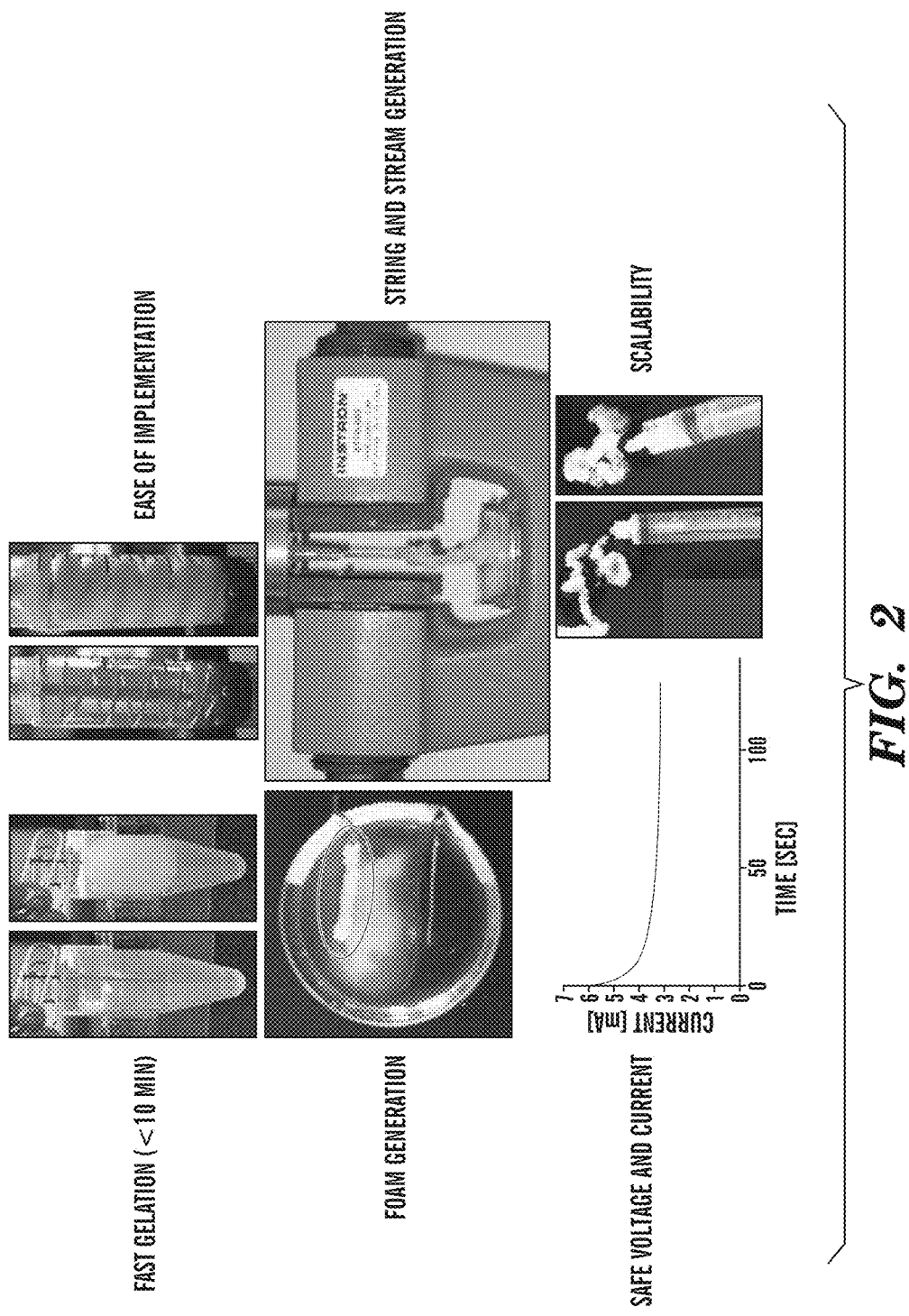
FIG. 2 shows several features of silk electrogelation.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Silk fibroin is a unique biopolymer that can be reconfigured from its native or synthesized states in various shapes and conformations. Silk fibroin protein has recently found uses well beyond textile and medical suture applications that have been the main modes of utilization in the past. For example, the generation of hydrogels (WO2005/012606; PCT/US08/65076), ultrathin films (WO2007/016524), thick films, conformal coatings (WO2005/000483; WO2005/123114), microspheres (PCT/US2007/020789), 3D porous matrices (WO2004/062697), solid blocks (WO2003/056297), microfluidic devices (PCT/US07/83646; PCT/US07/83634), electro-optical devices (PCT/US07/83639), and fibers with diameters ranging from the nanoscale (WO2004/0000915) to several centimeters (U.S. Pat. No. 6,902,932,) have been explored with implications in biomaterials and regenerative medicine (WO2006/042287; U.S. Patent Application Pub. No. 20070212730; PCT/US08/55072). The toughness of this natural fiber, unmatched in nature, confers impressive mechanical properties (both tensile and compressive) to silk-based materials which rival, if not exceed, most organic counterparts such as Kevlar® or other polymeric materials.

Silk has been used in biomedical applications for many years. Applications range from suture materials to tissue scaffolds used in the development of engineered tissues in the body, such as tendons, cartilage and ligaments. The forms of the silk required for particular applications vary. Much research, therefore, has gone into the development of silk films (Jin et al., 15 Adv. Funct. Matter 1241-47 (2005)), non-woven mats (Jin et al., 25 Biomats. 1039-47 (2004)), sponges (porous scaffolds) (Karageorgiou et al., Part A J. Biomed. Mats. Res. 324-34 (2006)), gels (Wang et al, 29 Biomats. 1054-64 (2008)), and other forms (Sofia et al., 54 J. Biomed. Materials Res. 139-48 (2000)).

For each of these forms, insect-derived silk is usually processed into solution using a two-stage procedure. In the case of silkworm silk, cocoons from *Bombyx mori* silkworms are boiled in an aqueous solution and subsequently rinsed to remove the glue-like sericin protein that covers the natural silk. The extracted silk fibroin is then solubilized (i.e., dissolved) in LiBr before being dialyzed in water. The solubilized silk fibroin concentration can then be adjusted according to the intended use. See U.S. Patent Application Pub. No. 20070187862. Alternatively, recombinant silk proteins may be used. These have proved advantageous when using spider silk because arachnid-derived silk proteins are often more difficult to collect in quantity. Kluge et al., 26(5) Trends Biotechnol. 244-51 (2008). Moreover, recombinant silk fibroin may be engineered to express heterologous proteins or peptides, such as dentin matrix protein 1 and RGD, providing additional biofunctionality to the silk fibroin proteins. Huang et al., 28(14) Biomats. 2358-67 (2007); Bini et al., 7(11) Biomacromolecules 3139-45 (2006).

The processing of silk solution into a target material form requires target-specific approaches that depend on the desired geometry and morphology. For example, electrospinning is a process used to generate nano-sized fibers that can be laid up into various mat and tubular structures. In this process a high voltage potential, typically between 10 kV-20 kV, is used to drive rapid ejection of a jet of silk solution from a needle, causing accelerated solidification of the jet into a sub-micron diameter solid fiber. The process can build up a layer with textile-like morphology and a smooth deposition underlayer. Li et al., 27 Biomats. 3115-24 (2006).

Another material form of special interest is silk gel. In biomedical applications, silk hydrogels are used for the encapsulation and delivery of cells and bioactive polymers. The high water content and mechanical response of hydrogels makes them suitable for some tissue restoration applications. In various polymer systems, a hydrogel is formed when the polymer chains cross-link into networks through chemical or physical means. Chemical triggers, such as cross-linking reagents, or physical stimulants, such as pH or temperature, have shown to be successful. Wang et al., 2008.

The silk electrogelation process as provided herein is very simple, involving the conversion of random-coil silk solution into a gel with an increase in the metastable silk I conformation by the application of an electric field using a voltage source, such as a DC or AC voltage source. Other methods of applying an electric field to the silk solution may also be used, such as current sources, antennas, lasers, and other generators. Interestingly, electrogelation using the present methods is reversible. When the DC voltage is reversed (reversal of the electrode polarity), the silk gel tends to convert back to a random coil conformation. The reversing process appears to be nearly complete, reversing can be repeated many times, and, perhaps most importantly, the nature of the material changes dramatically when alternating from gel to liquid silk solution. The gel has a very sticky, thick, mucus-like consistency. The liquid silk solution is not sticky at all and has a very low viscosity compared to the gel. The electrogelated silk, therefore, can be seen as an active silk muco-adhesive, analogous to the slime secretion that snails utilize for motion and for securing themselves to various surfaces.

In a simple silk electrogelation example, two parallel wires (electrodes) are placed along the bottom of a 70 mm diameter plastic culture dish that contains a few ml (4 ml) of ~9% solubilized silk fibroin solution, as shown in FIG. 1A. The liquid level may slightly cover the top of the electrodes and the electrodes, which in this instance were about 40 mm apart. A voltage potential of 22.2 VDC was applied using a high-current lithium polymer (Li-Pol) battery. The electrode connected to the positive terminal of the battery is denoted "+" (the anode) and the other electrode, connected to the negative terminal of the battery is denoted "−" (the cathode). As illustrated in the photograph of FIG. 1A, bubbles formed on both the positive and negative electrodes almost immediately after voltage application. The bubbles on the positive electrode, likely oxygen gas, soon became encapsulated in a growing "gel front" that emanated from the electrode outward, with a general directionality toward the negative electrode. Over the span of 275 minutes, a significant volume of the silk solution was gelated. This demonstrates the ability of the applied DC voltage to cause silk fibroin gelation. The effects of electrode surface area (FIG. 1B) and material (FIG. 1C) were also investigated. Other approaches, e.g., using coiled electrode geometries and/or using platinum as the electrode material (FIG. 1D) also resulted in silk fibroin gelation.

The power source of the electrogelation process can be any power source that provides a direct current voltage. Direct current is produced by sources such as batteries, thermocouples, solar cells, etc. Alternatively, alternating current (AC), the general powder source for business and residence, may also be used to induce the electrogelation process, although the gel formation may not be as fast as the gelation process induced by direct current voltage.

In general, after removal of the gelated silk from an electrogelation process, the resulting material is highly viscous, soft, and very tacky. Over time, the gelated silk may become very stiff. FIG. 2 shows several features of silk electrogelation. Electrogelation is a low voltage and current process and can cause gelation in less than 10 minutes. The process can be incorporated in hand-held devices, providing a low cost yet scalable approach to varying target gelation volumes. Modifications of the silk can impart flavor for some applications and allow the encapsulation of cells or bioactive molecules for others. The demonstrated ability to provide biocompatibility and controlled degradation of silk are also elements that can be incorporated in application-specific manifestations.

Figure 24:
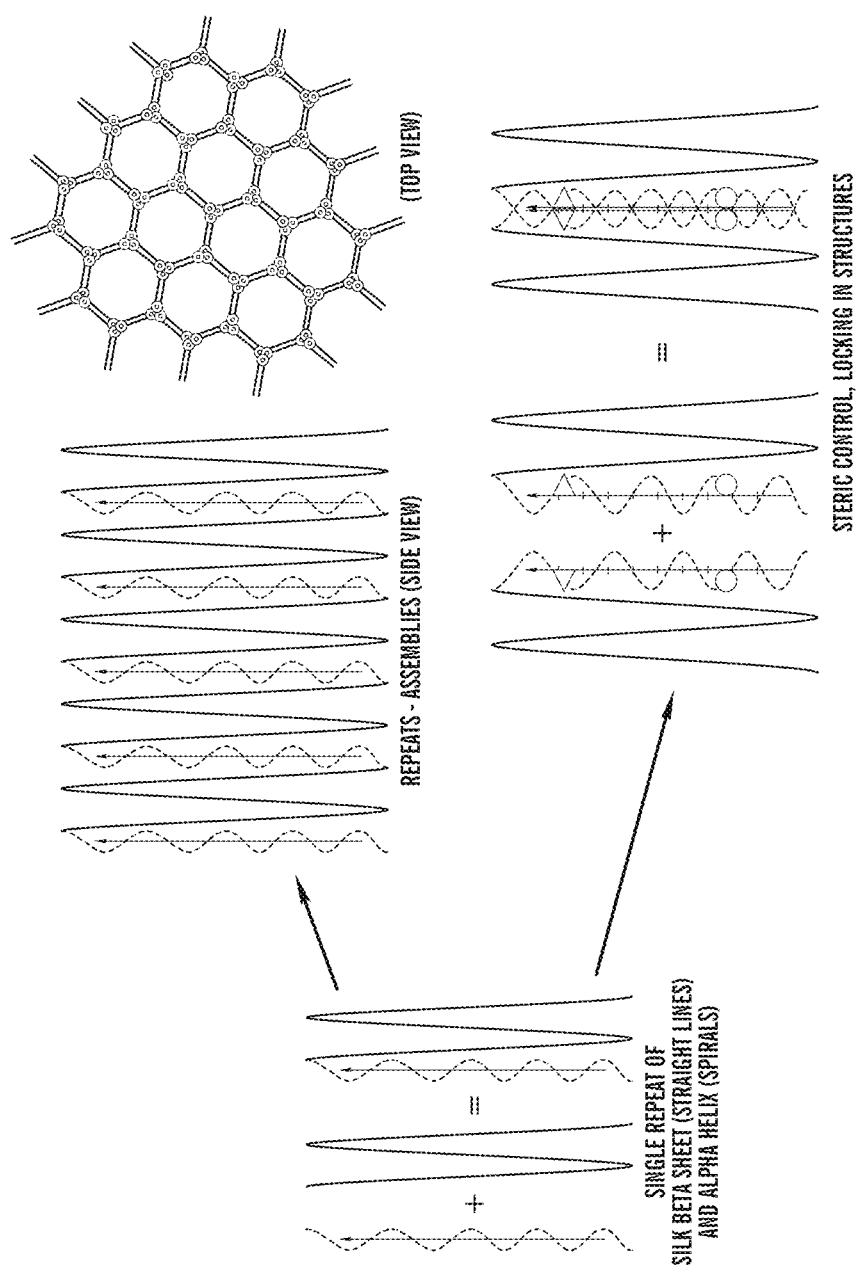
FIG. 24 is a schematic showing structural examples of piezoelectric silk-based proteins that may be created and manipulated using electrogelation.
Figure 25:
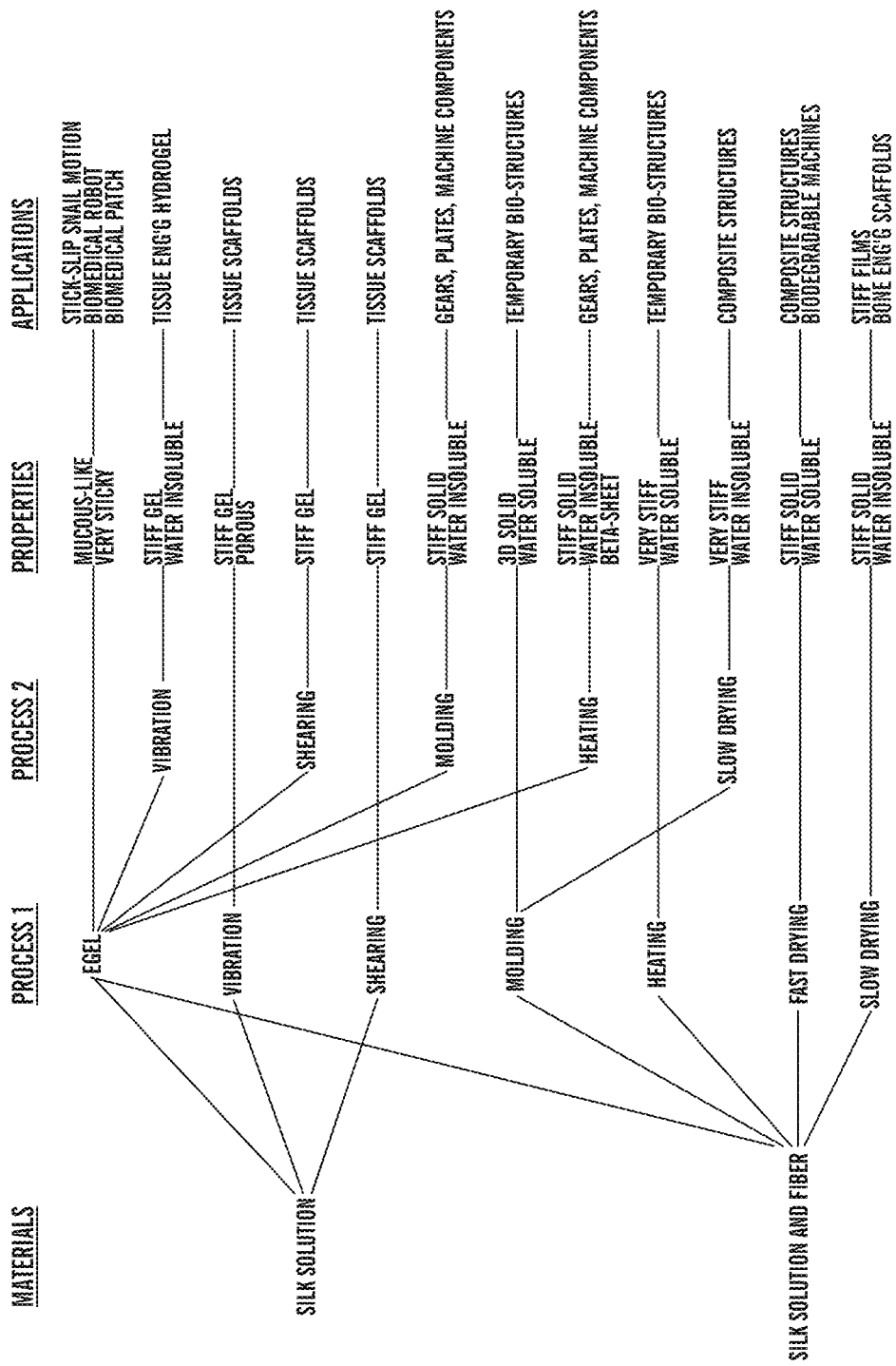
FIG. 25 is a depiction of silk processing techniques, predicted properties, and potential applications.
Figure 28A:
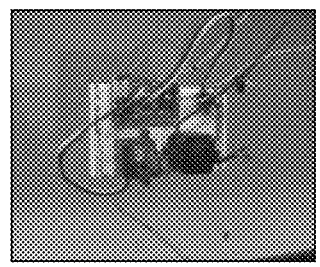
FIGS. 28A-28D show a surveillance platform mounted to acrylic and wood surfaces in both vertical and horizontal orientations through action of active silk muco-adhesive.
Figure 28B:
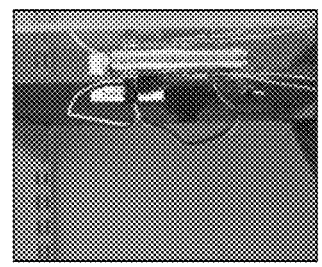
Figure 28C:
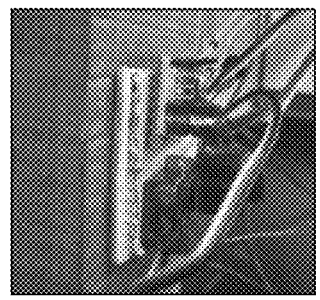
Figure 28D:
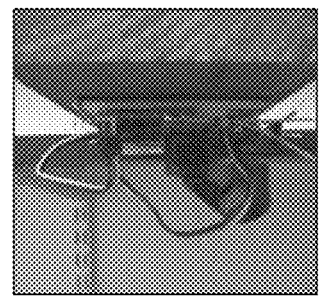
Figure 29A:
FIGS. 29A-29C show a helical coil electrogelation pad design.
Figure 29B:
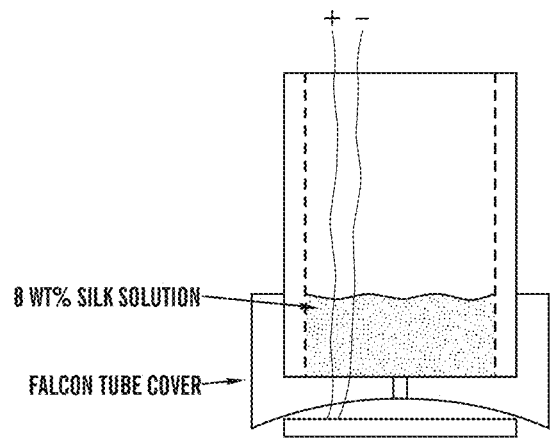
Figure 29C:
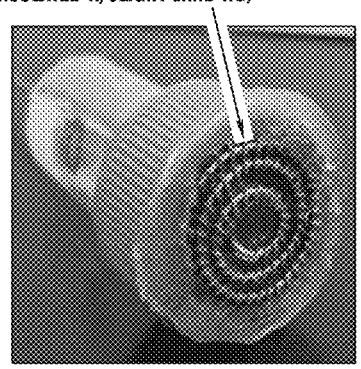
Figure 30C:
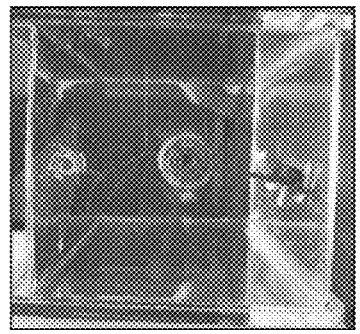
FIGS. 30A-30C show the electrogelation and controlled release from an underwater, vertical, Plexiglass surface.
Figure 31C:
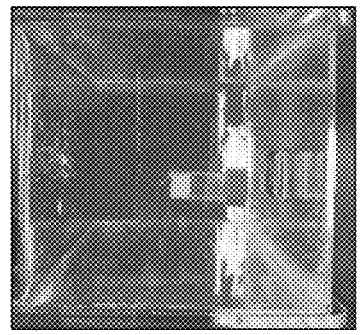
FIGS. 31A-31C show the electrogelation and controlled release as applied to the lifting of an underwater weight.
Figure 30B:
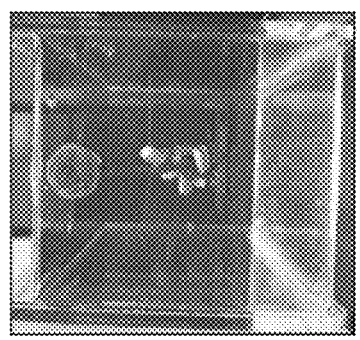
Figure 31B:
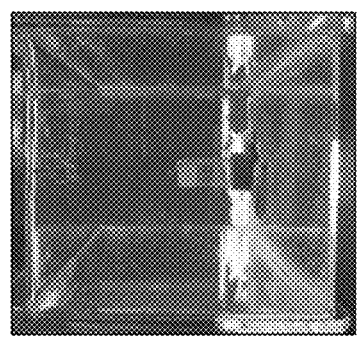
Figure 30A:
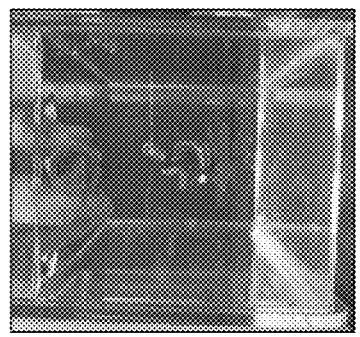
Figure 31A:
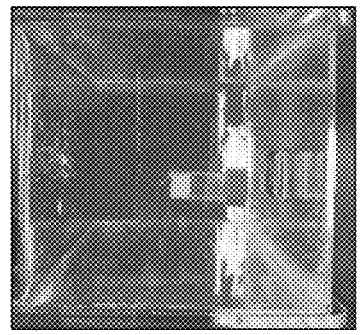

As noted, electrogelation appears to trigger a conformational shift of at least some of the silk fibroin from random coil to the silk I conformation. This phenomenon is unique from that achieved by some other mechanisms of inducing silk gelation, such as pH manipulation, heating, application of various ions and mechanical shearing, which tend to result primarily in β-sheet conformation. The increase in meta-stable silk I conformation achieved with electrogelation is a more versatile material phase to achieve than is the beta-sheet conformation. For example, the silk I gel form can be transformed back to liquid form (random coil); or through minimal additional molecular alignment, can be converted to β-sheet. This allows for the creation and manipulation of complexes comprising both structures, as shown in FIG. 24.

Interestingly, silk polypeptide chains in an α-helical arrangement have also been shown to exhibit piezoelectric properties. Piezoelectric materials are known to be as high as 75% efficient in converting an electrical signal into a physical dimension change, or vice versa. Bone exhibits piezoelectric properties due to a calcified (helical) collagen matrix, which comprises much of its structure. The minute electrical signals caused by the mechanical loading and unloading of bones plays an important role in both bone formation and repair. Matching these native properties in an implanted device has the potential to speed patient recovery and aid in the restoration of pre-injury motility. A hybrid material containing the strong and slow-degrading silk motifs along oriented silk I domains provides a strong "smart" materials platform that can be used in a number of biomedical applications including improved bone repair. By tailoring the relative ratios of α-helical content to β-sheet content, the strength, degradability, and piezoelectric properties of a silk macrostructures can be varied over a range of material properties.

Without being bound by theory, electrogelation might be explained as a conformation change due to an applied electric field. Although the typical introduction of electrodes and voltage directly in the water-based silk solution instigates electrolysis, it is not thought to play a major role in the electrogelation. Electrolysis quickly affects the pH level of the silk solution at the electrodes: the pH near the positive electrodes decreases (below pH 4), while it increases near the negative electrode (above pH 13). It is likely that oxygen gas is generated at the positive electrode and hydrogen gas at the negative, influencing the pH levels. Importantly, these pH changes do not appear to be a requirement for electrogelation, which occurs independent of pH in the silk fibroin. Electrogelation may be achieved at pH ranges of about pH 6 to about pH 7.5. In terms of an electrical explanation of the process, it is important to recognize that the silk protein consists of highly repetitive amino acid sequences with small side chains (glycine, alanine, serine). In the presence of an electric field, polar side chains, which act as magnetic dipoles, may orient in the direction of the field and molecular conformations that have large electric moments perhaps increase in concentration. In the case of electrogelation, it is likely that the conformation change represented by the gel formation is due to such a mechanism. Neumann, 47 Prog. Biophys. Molec. Bio. 197-231 (1986).

Figure 3:
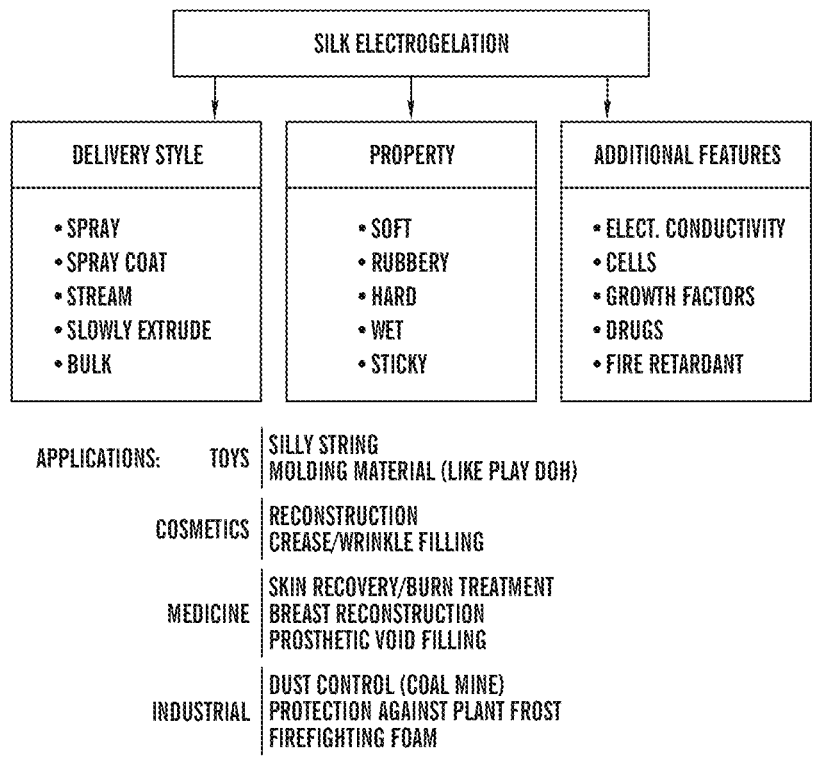
FIG. 3 presents various delivery styles, properties, and additional features of silk electrogelation.

Potential applications are depicted in FIG. 3, which describes various delivery styles, achievable gel properties, and additional features that are encompassed in the present invention. Electrogelated silk may be delivered in the form of a spray, stream, slow extrusion, and for creation of gel in bulk. Gel processing and manipulation have shown that soft, rubbery, hard, wet, and sticky consistencies can be achieved. Combinations of these properties are also achievable. For example, a soft, wet, and sticky form of the gelated silk can be created. These styles, properties, and features provide significant opportunity for electrogelation in many potential applications.

For example, SILLY STRING® party string (Just For Kicks, Inc.), is an aerosol can that ejects a liquid that forms into a sticky stream of brightly-colored plastic string. See e.g., the How Stuff Works web site. Although mainly marketed to children, the product has found a new application with the U.S. military in Iraq, where soldiers use it to reveal well-disguised trip wires on doorways and in rooms, thereby preventing serious harm to personnel. Santana, *N.J. woman collects Silly String for serious mission in Iraq*, USA TODAY (Dec. 11, 2006). Although the product is very popular, especially with children and during celebrations, it can be harmful when used around an open flame, can cause damage to wallpaper and other materials, and is not biodegradable and may be particularly harmful to marine life. Indeed, some locales such as Los Angeles (where clean-up from Halloween-night party string exceeds $200,000) have banned it. LAMC §56.02 (2004). A silk-based party string can be also ejected in a flexible stream; but unlike existing party string, the silk gel version is biodegradable and biocompatible, causing less harm to the environment and providing higher safety around children. In fact, the silk gel may also be flavored and ingested with minimal risk.

Another embodiment of the present invention provides for foams or gels for use in firefighting. Various firefighting gels are available commercially. For example, THERMO-GEL® gel concentrate (Thermo Technologies, LLC) transforms into a Class A fire retardant gel when added to water. It can be effective for fighting fires, in aviation applications, and for protecting structures. Another commercially available firefighting gel, AURORAGEL™ breakable fire gel (McCoy & Assoc., Inc.) stops and prevents fires by restricting availability of oxygen, isolating the fuel source with a layer of gel, and by lowering the temperature of what is burning. AURORAGEL™ fire gel, essentially a thick layer of gelled water, ensures that water stays in contact with surfaces. It can be sprayed on horizontal and vertical surfaces, but also on firefighters for additional protection. This gel can be delivered with a nozzle, contains safe gelling agents, and can be removed with calcium-containing water. Utilizing the electrogelation process described herein, silk-based gels may be utilized in firefighting applications. The ability to quickly gelate silk solution and spray it through a nozzle has been demonstrated. Utilizing chemical modifications the fire retardancy of the silk gel may be improved. The resulting gel may be composed of an all-aqueous system that is biocompatible and biodegradable and has the ability to be sprayed onto vertical and horizontal structural elements, and onto firefighters themselves for additional protection.

An important embodiment of the present invention provides for medical applications such as burn and wound treatment. Burn victims require treatment strategies that involve palliative measures to cool affected tissue and prevent infection to more intensive strategies that involve removal of severely damaged tissue and replacement with suitable material(s). Currently, there are many products on the market that can be used for burn treatment in emergency first-aid scenarios. For example, Water-Jel Technologies (Carlstadt, N.J.) produces blankets, dressings, and gels that incorporate a water-based hydrogel that has both bacteriostatic and biodegradable properties. The gel cools the burned area, can protect against infection, and can include lidocaine to relieve pain. BURNFREE Products (Sandy, Utah), has a similar line of burn treatment products. Their highly viscous gel remains in place on a burn wound, but can be rinsed off completely for further treatment. The gel contains anti-evaporative, thickening, and preservative additives to ensure functionality under expected usage conditions. Other more sophisticated products derived through tissue engineering research are becoming available on the market. OASIS® wound matrix from Cook Biotech, Inc. (West Lafayette, Ind.) is a material, derived from porcine sources, that may be used to treat second-degree burns, providing a moist environment that allows the patient's cells to replace damaged tissue.

For moderate skin burns, where significant damage has occurred, autografting can be one treatment strategy. Autografting involves replacement of damaged skin with healthy skin from elsewhere in the body. As an alternative to this approach, a product from Genzyme (Cambridge, Mass.), known as EPICEL® cultured epidermal autograft, can be used as a permanent skin replacement. By using the patient's skin cells (co-cultured with mouse cells), an allograft can be cultured without fear of immune rejection. The process may take two weeks, producing enough replacement skin to cover an entire body. EPICEL® cultured epidermal autograft is used at major burn centers in the U.S. Other products that are used in similar applications include Integra™ bilayer matrix wound dressing (Integra Lifescience Holdings Corp., Ontario, Canada); ALLODERM® acellular dermal matrix (Life-Cell Corp., Branchburg, N.J.); ORCEL® bilayered cellular matrix (Forticell Bioscience, Inc., New York, N.Y.); and APLIGRAF® living skin patch (Organogenesis Inc., Canton, Mass.).

A silk-based hydrogel product may have a significant impact in the treatment of wounds, particularly burn wounds. Because the silk gel is water-based and biodegradable, it can be easily applied or removed without generating waste. Its adhesive qualities and high viscosity allow it to stay in place, cooling the wound and preventing airborne contamination. With the application of tissue engineering approaches and recombinant techniques, cells, drugs, and/or other bioactive molecules may be incorporated into silk gels to protect the wound and stimulate tissue regeneration. For example, if the silk fibroin peptide employed in the electrogelation process does not include a recombinant growth factor such as VEGF or BMP-2, these may be conjugated to the fibroin protein or added to the fibroin solution at some suitable time before electrogelation is undertaken.

Furthermore, because silk gel may be manipulated to effect structural conformation, particularly in triggering β-sheet conformation, silk gel may be particularly useful in bone repair. For example recombinant silk peptides may be electrogelated to silk I conformation peptides in combinations of the silk consensus repeats and added helical domains in a parallel fashion with respect to the folding of the beta-sheets. In this way the dipole moments of the silk I conformation combine in an additive fashion and do not cancel each other out, leading to a net dipole moment of the material, which gives rise to bulk piezoelectric behavior as described above. By varying the content of the silk I domains, the net piezoelectric response can be tailored. Additionally, when producing a bulk material, the protein containing the silk I domains can be blended with unmodified silk proteins to increase the net strength of the system and alter the net piezoelectric properties of the system. The bulk material must be sufficiently anisotropically oriented such that a net dipole is present. By utilizing silk I conformations from the electrogelation process, which themselves self-assemble in a parallel manner, the overall system exhibits increased orientation. For production of fibers one can extrude protein from a narrow orifice to induce molecular alignment. Slow drying of the systems can aid in the most energetically favorable parallel arrangement resulting in a net dipole moment for the system. Initial materials may be tested on a microscopic level by AFM wherein the electrical response of a region is measured as the AFM tip impacts the surface. Measurements on bulk materials can be performed via a number of techniques including load testing while coupled to an electronic load. Electrogelation thus offers the ability to study and harness the relative ratios of silk-helical content in the protein matrixes, to optimize piezoelectric features related to mechanical properties, and identify suitable options in forming bulk systems useful for the bone repair system.

For example, because silk electrogelation may be achieved with hand-held commercial Li-Pol batteries, the present approach may prove extremely useful for first responders such as paramedics or field doctors in the military. Solubilized silk fibroin solution, which has less volume than silk gel, is aqueous and stable at ambient temperature, may be carried in a device equipped with a battery and a switch, such that when the silk gel is needed (e.g., to cover a wound), the medical personnel can expose a portion of the silk solution to the battery-operated field, and within ten minutes have silk gel suitable for use on the patient.

Figure 22:
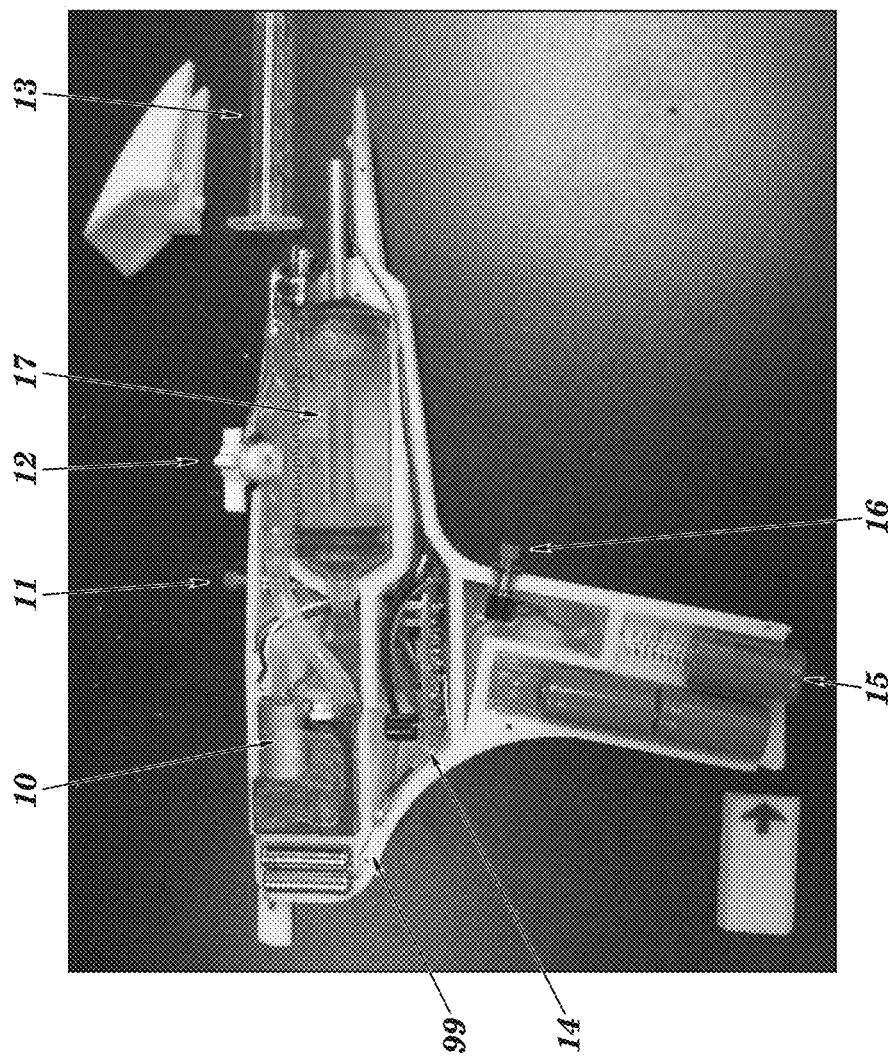
FIG. 22 is a photograph of an embodiment of a hand-held silk gel extruder with the following components labeled as follows: housing 99, hydraulic pump 10, process button 11, operation valve 12, silk cartridge 13, timing and logic board 14, rechargeable batteries 15, extrusion button 16, hydraulic drive 17.

For example, with reference to FIG. 22, this is an embodiment of a device and a housing (99) for generating internally electrogelated silk and delivering a steady stream for biomedical-type application, for instance. In use, the operation valve (12) is opened and the silk cartridge (13) containing silk fibroin solution is inserted. At this point, an LED displays a stand-by signal (e.g., green). The user presses the process button (11), which triggers the timing and logic board (14) to generate an electric field using batteries (15), which may be rechargeable batteries. The LED displays a different color (e.g., red), indicating that processing is underway. The timing and logic board (14) also adjustably monitors time for the gelation processing. When the preset time elapses, the LED changes color (e.g., back to green), and the user then closes the operation valve (12). When the user presses the extrusion button (16), the hydraulic pump (10) and the hydraulic drive (17) engage to eject the silk gel from the tip of the unit.

Figure 23:
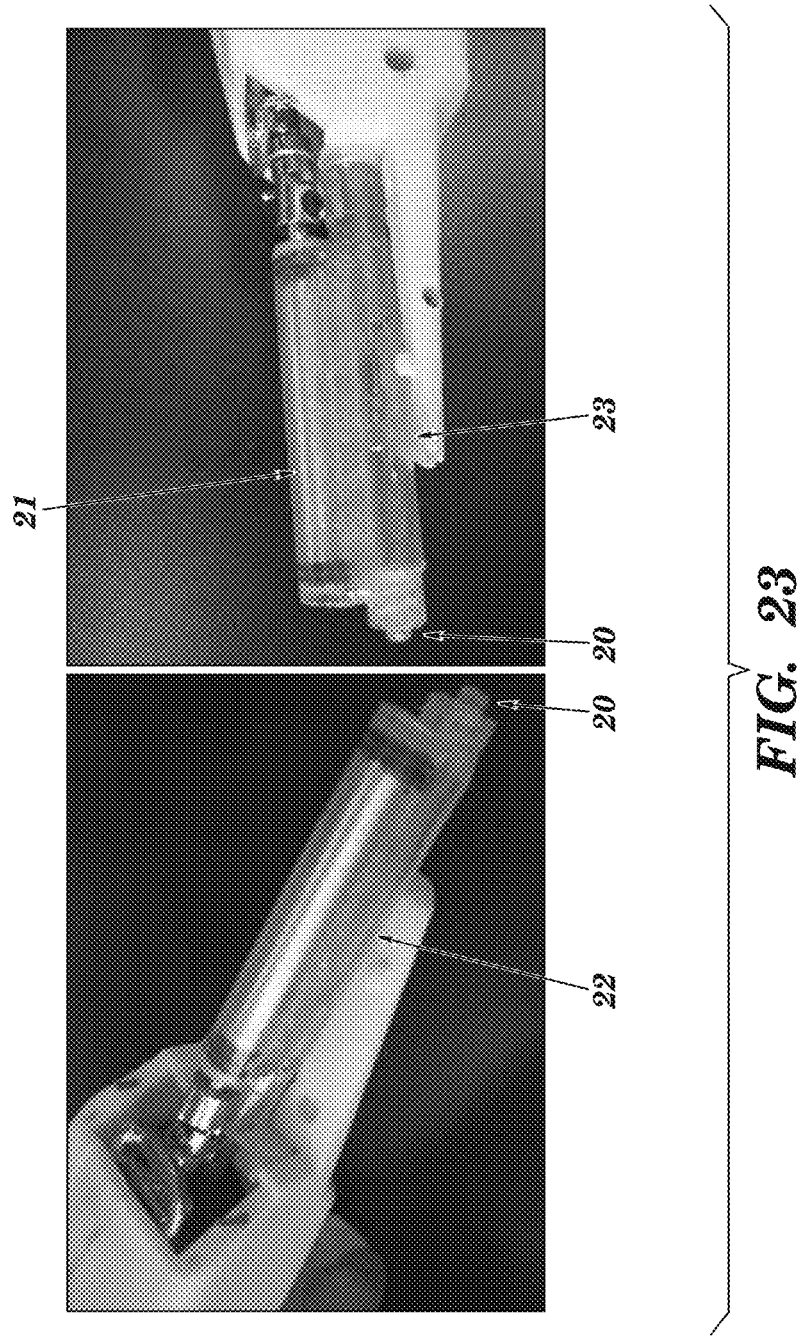
FIG. 23 shows the left and right perspectives of the delivery end of an embodiment for the delivery of silk gel to a particular site. The photographs are labeled as follows: nozzle attachment 20, valve and (−) platinum electrode 21, silk solution 22, (+) platinum electrode 23.

A device for the delivery of silk gel to a desired location may also use a special silk cartridge device as shown in FIG. 23. In this figure, DC voltage is supplied by batteries and creates an electric field in the silk solution (22) via a positive platinum electrode (23) immersed in the silk solution, and a tube-shaped negative electrode that also acts as a valve (21). Also shown is a nozzle attachment (20), which may be removed and exchanged for a nozzle with a larger or smaller aperture to effect the shear forces applied to the silk gel as it is ejected from the nozzle (20). By applying a selected shear force to the electrogelated silk, via the nozzle, the molecular conformation of the meta-stable silk gel may be manipulated from, e.g., silk I to beta-sheet, impacting the solubility and mechanical properties of the extruded silk gel.

Another embodiment of the present invention provides for an the electrogelation of silk fibroin for use as a medical filled material in cosmetic surgery or reconstruction. Current approaches to cosmetic enhancements may use injections of Botox® botulinum toxin type A (Allergan Inc., Irvine, Calif.), to paralyze facial muscles, temporarily eliminating frown lines or wrinkles. Alternatively, Cosmoderm® collagen dermal filler and Cosmoplast® collagen dermal filler are "human-based" protein implants, and Zyderm® and Zyplast® collagen implants are bovine-derived products that have been FDA-approved for smoothing facial lines, wrinkles and scars. Other materials, such as hyaluronic acid, can fill thin lips and facial creases. Hydroxylapatite, a mineral-like material found in human bones, can fill deeper creases. Additionally, adipose (fat) tissue can be harvested from the patient's own body and injected in facial locations where fillers build up creases or smooth wrinkles. Certain traumas or diseases that require the removal of tissue in affected areas can leave defects or voids that need filling. For example, a mastectomy results in the creation of large void space in the breast that could be eliminated by suturing a skin fold over where the breast once existed or by refilling the breast with an implant or adipose (fat) tissue harvested from the patient. Due to lack of revascularization, reduction in graft volume can be an issue. Tissue engineering approaches to adipose tissue for breast reconstruction have been pursued. Porous polymer foams, such as from PLGA, have been seeded with preadipocytes to generate adipose tissue formation. These materials are thought to be too stiff, making the patient uncomfortable. Injection of materials, such as alginate and hyaluronic acid hydrogels, has also been investigated. Patrick, 19 Seminars Surgical Oncol. 302-11 (2000).

Electrogelated silk may serve in both cosmetic surgery and for reconstructive surgeries. Silk hydrogels are easily tailored to have the properties desired for the particular application. For example, in breast reconstruction, a soft silk gel injection may provide a higher level of comfort for the patient than reported for implanted PLGA. The demonstrated ability to cell-seed silk-derived gels that can differentiate into viable engineered tissues is attractive for many surgical applications. If a rapid prototyping capability can be developed based on silk electrogelation, potentially 3D images scanned from a patient prior to surgery can be used to generated a 3D tissue engineering scaffold. Applying known tissue engineering strategies, seeded cells may differentiate into adipose tissue, providing both geometry that matches the patient's natural breast geometry and long-term stability.

As noted, electrogelated silk may be modified to allow for encapsulation of at least one agent into silk gels. The agent may be introduced into the silk fibroin solution before, during or immediately after applying voltage to the silk solution to generate an electric field. Some agents may be affected adversely by the voltage or current and hence may not be introduced into the silk fibroin solution until after the application of the electric field. For example, applying electric current may damage or destroy living cells, depending on the magnitude of the applied voltage and current. Hence caution may be applied to the procedures and conditions of encapsulating agents into the electrogelated silk, for example, the agent may be introduced to silk solution immediately after the application of the electric field.

The agent to be encapsulated into electrogelated silk can be any material capable of being encapsulated in the silk gel. For example, the agent may be a therapeutic agent or biological material, such as cells (including stem cells), proteins, peptides, nucleic acids (DNA, RNA, siRNA), nucleic acid analogues, nucleotides, oligonucleotides or sequences, peptide nucleic acids, aptamers, antibodies, hormones, hormone antagonists, growth factors or recombinant growth factors and fragments and variants thereof, cytokines, or enzymes, antibiotics, viruses, antivirals, toxins, prodrugs, chemotherapeutic agents, small molecules, drugs and combinations thereof. Exemplary agent suitable for encapsulation into electrogelated silk includes cells (including stem cells), erythropoietin (EPO), YIGSR peptides, glycosaminoglycans (GAGs), hyaluronic acid (HA), integrins, selectins, and cadherins; analgesics and analgesic combinations; steroids; antibiotics; insulin; interferons $\alpha$ and $\gamma$; interleukins; adenosine; chemotherapeutic agents (e.g., anticancer agents); tumor necrosis factors $\alpha$ and $\beta$; antibodies; cell attachment mediators, such as RGD or integrins, or other naturally derived or genetically engineered proteins, polysaccharides, glycoproteins, cytotoxins, prodrugs, immunogens, or lipoproteins.

One or more agents may be encapsulated into electrogelated silk. For instance, when encapsulating biological material such as cells, it may be desirable to add other materials to promote the growth of the agent, promote the functionality of the agent after it is released from the encapsulation, or increase the agent's ability to survive or retain its efficacy during the encapsulation period. Exemplary materials known to promote cell growth include, but are not limited to, cell growth media, such as Dulbecco's Modified Eagle Medium (DMEM), fetal bovine serum (FBS), non-essential amino acids and antibiotics, and growth and morphogenic factors such as fibroblast growth factor (e.g., FGF 1-9), transforming growth factors (TGFs), vascular endothelial growth factor (VEGF), epidermal growth factor (EGF), platelet derived growth factor (PDGF), insulin-like growth factor (IGF-I and IGF-II), bone morphogenetic growth factors (e.g., BMPs 1-7), bone morphogenetic-like proteins (e.g., GFD-5, GFD-7, and GFD-8), transforming growth factors (e.g., TGF-$\alpha$, TGF-$\beta$ I-III), nerve growth factors, and related proteins. Growth factors are known in the art, see, e.g., Rosen & Thies, CELLULAR & MOL. BASIS BONE FORMATION & REPAIR (R. G. Landes Co.). Additional material to be encapsulated in silk gel may include DNA, siRNA, antisense, plasmids, liposomes and related systems for delivery of genetic materials; peptides and proteins to active cellular signaling cascades; peptides and proteins to promote mineralization or related events from cells; adhesion peptides and proteins to improve gel-tissue interfaces; antimicrobial peptides; and proteins and related compounds.

The electrogelated silk encapsulating bioactive agent enables the delivery of active agents in a controlled released manner. Maintaining the bioactive agent in an active form throughout the electrogelated silk preparation process enables it to be active upon release from the silk gel. Controlled release of the active agent permits active agent to be released sustainably over time, with controlled release kinetics. In some instances, the bioactive agent is delivered continuously to the site where treatment is needed, for example, over several weeks. Controlled release over time, for example, over several days or weeks, or longer, permits continuous delivery of the bioactive agent to obtain preferred treatments. The controlled delivery vehicle is advantageous because it protects the bioactive agent from degradation in vivo in body fluids and tissue, for example, by proteases.

Controlled release of the active agent from the electrogelated silk may be designed to occur over time, for example, over 12 hours or 24 hours. The time of release may be selected, for example, to occur over a time period of about 12 hours to 24 hours; about 12 hours to 42 hours; or, e.g., about 12 to 72 hours. In another embodiment, release may occur for example on the order of about 1 day to 15 days. The controlled release time may be selected based on the condition treated. For example, longer times may be more effective for wound healing, whereas shorter delivery times may be more useful for some cardiovascular applications.

Controlled release of the active agent from the electrogelated silk in vivo may occur, for example, in the amount of about 1 ng to 1 mg/day. In other embodiments, the controlled release may occur in the amount of about 50 ng to 500 ng/day, or, in another embodiment, in the amount of about 100 ng/day. Delivery systems comprising therapeutic agent and a carrier may be formulated that include, for example, 10 ng to 1 mg therapeutic agent, or about 1 µg to 500 µg, or, for example, about 10 µg to 100 µg, depending on the therapeutic application.

A pharmaceutical formulation may be prepared that contains the electrogelated silk encapsulating bioactive agents. The bioactive agents may be one or more active agents described above. The formulation can be administered to a patient in need of the particular bioactive agent that has been encapsulated in the electrogelated silk.

The pharmaceutical formulation may also contain common components found in other pharmaceutical formulations, such as known excipients. Exemplary excipients include diluents, solvents, buffers, or other liquid vehicle, solubilizers, dispersing or suspending agents, isotonic agents, viscosity controlling agents, binders, lubricants, surfactants, preservatives, stabilizers and the like, as suited to particular dosage form desired. The formulations may also include bulking agents, chelating agents, and antioxidants. Where parenteral formulations are used, the formulation may additionally or alternately include sugars, amino acids, or electrolytes.

Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; oils such as peanut oil, cottonseed oil; safflower oil, sesame oil; olive oil; corn oil and soybean oil; esters such as ethyl oleate and ethyl laurate; agar; non-toxic compatible lubricants such as sodium lauryl sulfate and magnesium stearate; polyols, for example, of a molecular weight less than about 70,000 kD, such as trehalose, mannitol, and polyethylene glycol. See for example, U.S. Pat. No. 5,589,167, the disclosure of which is incorporated by reference herein. Exemplary surfactants include nonionic surfactants, such as Tween surfactants, polysorbates, such as polysorbate 20 or 80, etc., and the poloxamers, such as poloxamer 184 or 188, Pluronic polyols, and other ethylene/polypropylene block polymers, etc. Suitable buffers include Tris, citrate, succinate, acetate, or histidine buffers. Suitable preservatives include phenol, benzyl alcohol, metacresol, methyl paraben, propyl paraben, benzalconium chloride, and benzethonium chloride. Other additives include carboxymethylcellulose, dextran, and gelatin. Suitable stabilizing agents include heparin, pentosan polysulfate and other heparinoids, and divalent cations such as magnesium and zinc. Coloring agents, releasing agents, coating agents, sweetening, flavoring and perfuming agents, preservatives and antioxidants can also be present in the composition, according to the judgment of the formulator.

The pharmaceutical formulation may be administered by a variety of routes known in the art including topical, oral, ocular, nasal, transdermal or parenteral (including intravenous, intraperitoneal, intramuscular and subcutaneous injection as well as intranasal or inhalation administration) and implantation. The delivery may be systemic, regional, or local. Additionally, the delivery may be intrathecal, e.g., for CNS delivery.

The pharmaceutical formulations may contain common components found in other pharmaceutical formulations, such as known excipients. Exemplary excipients include diluents, solvents, buffers, or other liquid vehicle, solubilizers, dispersing or suspending agents, isotonic agents, viscosity controlling agents, binders, lubricants, surfactants, preservatives, stabilizers and the like, as suited to particular dosage form desired. The formulations may also include bulking agents, chelating agents, and antioxidants. Where parenteral formulations are used, the formulation may additionally or alternately include sugars, amino acids, or electrolytes.

Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; oils such as peanut oil, cottonseed oil; safflower oil, sesame oil; olive oil; corn oil and soybean oil; esters such as ethyl oleate and ethyl laurate; agar; non-toxic compatible lubricants such as sodium lauryl sulfate and magnesium stearate; polyols, for example, of a molecular weight less than about 70,000 kD, such as trehalose, mannitol, and polyethylene glycol. See e.g., U.S. Pat. No. 5,589,167. Exemplary surfactants include nonionic surfactants, such as Tween surfactants, polysorbates, such as polysorbate 20 or 80, etc., and the poloxamers, such as poloxamer 184 or 188, Pluronic polyols, and other ethylene/polypropylene block polymers, etc. Suitable buffers include Tris, citrate, succinate, acetate, or histidine buffers. Suitable preservatives include phenol, benzyl alcohol, metacresol, methyl paraben, propyl paraben, benzalconium chloride, and benzethonium chloride. Other additives include carboxymethylcellulose, dextran, and gelatin. Suitable stabilizing agents include heparin, pentosan polysulfate and other heparinoids, and divalent cations such as magnesium and zinc. Coloring agents, releasing agents, coating agents, sweetening, flavoring and perfuming agents, preservatives and antioxidants can also be present in the composition, according to the judgment of the formulator.

The pharmaceutical formulations containing the electrogelated silk encapsulating therapeutic agent can be administered in a controlled-release manner so that portions of the therapeutic agent are released in the patient over a period of time. The therapeutic agent may release quickly or slowly. For instance, the pharmaceutical formulation can be administered so that less than about 5% of the therapeutic agent is released in the patient from the electrogelated silk over a period of one month. Alternatively, a larger portion of the therapeutic agent may be released initially, with a smaller portion retained in the silk gel and released later. For example, the pharmaceutical formulation can be administered so that at least 5% of the therapeutic agent remains in the silk 10 days after administration.

The electrogelated silk may encapsulate various other active agents useful in a variety of fields. For instance, the active agent may be an enzyme or an enzyme-based electrode. The enzyme or enzyme-based electrode may be used in the field of tissue engineering, biosensors, the food industry, environmental control, or biomedical applications. The system can also be used as a reservoir for a variety of needs, such as in the food industry to harbor vitamins, nutrients, antioxidants and other additives; in the environmental field to harbor microorganisms for remediation or water treatments; in materials as additives to serve as a source of in situ detection and repair components, such as for nondestructive evaluation of material failures and self-repairs of the materials; and for biodetection schemes to help stabilize cells, molecules and related systems.

As noted herein, silk fibroin gels are edible and may be flavored. Hence, a flavored silk gel formulation of vitamins, nutraceuticals, or other pharmaceuticals may be produced for pediatric use. The gels may be preformed and packaged, or prepared as a solution in a suitable dispenser that will create the gel at the office or home under adult supervision.

Another embodiment of the present invention provides for electrogelated silk for use as biodegradable and biocompatible coatings on tissues, regenerated tissues, medical devices, and medical implants. Biodegradable and biocompatible implant coatings are of clinical interest due to their ability of continuously eluting desired drugs (e.g. anti inflammatory medication or growth factors) to the surrounding tissue of the implant. Additional drug delivery methods such as intravenous delivery thus can be avoided. By embedding drug in the implant or device coating, the drug is concentrated at the target site in a higher dosage and is less spread over the whole organism.

Current biodegradable biocompatible implant coatings such as PLA or PGA films involve elevated processing temperatures or harsh conditions that can damage the activity of drugs to be incorporated. In addition, due to the limitation of the conventional coating technique and coating materials, the conventional degradable implant coatings are only applicable to simple implant forms, and are not suitable for the coating of complex implant geometries such as implants having internal configurations or undercuts. The modern advanced biomechanical designs, however, often lead to complex implant forms that are used in biomedical field such as dental implantology, traumatology, orthopedics and cardio vascular applications. Hence a novel type of biodegradable biocompatible implant coating material and techniques are needed for complex implant designs such as spine cages, coronary stents, dental implants or hip and knee prostheses.

Electrogelation may prove superior to other medical device coating technique since electrogelation can be applied using a wide range of electrode materials and geometries, from platinum wire electrodes to mating metal plates to tissues (in vitro or in vivo) that can be coated with silk. Silk e-gel (silk e-gel, defined herein, refers to the electrogelated silk gel) in accordance with the present invention hence may be used as thin film coatings or bulk coatings on tissues or a variety of medical devices and medical implants.

The silk e-gel coating technique herein employs the silk electrogelation process described in the embodiments of the present invention. In a simple example for silk e-gel coating process, aqueous silk fibroin solution can be locally turned in a gel-like state by means of applying electric energy. The medical device such as an implant is used in effect as the positive electric pole (e.g., the implant or device is attached to the positive electric pole of the circuit) and is immersed into the aqueous silk solution until all surfaces of the device desired to be coated are in contact with the solution. When applying appropriate voltage and current (e.g., U=25V, I=10 mA), the aqueous silk solution surrounding the positive electric pole (the device) almost immediately turn into a gel like structure (so called e-gel effect) and the gel-like structure grows from the solution-contacting surface (either exterior surface or interior surface of a complex geometry) of the device to the surrounding silk solution until the electronic circuit is opened. The e-gel effect may be applied to any substrate (e.g., tissues or medical devices) inserted into the silk solution and can generate a homogenous biodegradable and biocompatible silk e-gel coating on the substrate.

The silk e-gel coating may be either in a form of bulk gel coatings or as a thin film coating. For example, the electrogelation process described above can generate a homogenous bulk silk e-gel coating that is growing on the surface of the substrate. Optionally, the silk e-gel coated substrate may be further treated with a dehydrating treatment method to achieve a stable beta-sheet conformation. Dehydrating treatment may refer to drying the silk e-gel coated substrate in the air or exposing the silk e-gel coated substrate to a flow of dehydrating gas such as nitrogen gas or a dehydrating solvent such as methanol. For example, drying the silk e-gel coating can induce the evaporation of water and convert the silk e-gel coating to a mechanically stable silk thin film on the substrate.

Figure 32A:
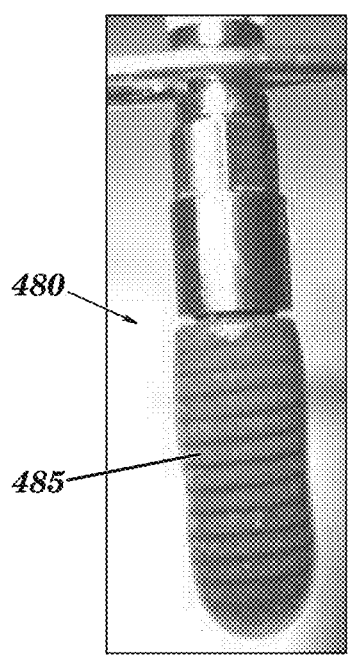
FIGS. 32A and 32B are pictures of a dental implant coated with the electrogelated gel before and after being dried for about 2 hours at room temperature.
Figure 32B:
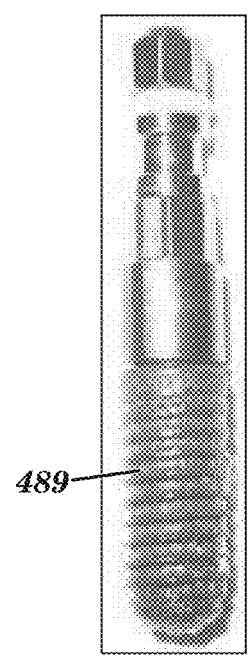

FIG. 32A illustrates a Straumann® dental implant (BL RC, ø 4.1 mm, 10 mm SLActive®, Straumann, Basel, Switzerland) coated with silk e-gel via the described direct electrogelation technique. The dental implant 480 is used as the positive electric pole and is inserted into about 4.5% silk solution. A voltage potential of 25V was applied on the dental implant 480 with a current of 10 mA for 10 seconds. A homogenous silk e-gel 485 is then formed on the dental implant 480. The silk e-gel coated dental implant 480 shown as in FIG. 32A may be dried for 2 hours at room temperature to evaporate water in the e-gel. The silk e-gel then shrinks and forms a mechanically stable silk thin film 489, as shown in FIG. 32B.

The substrates for coating of the electrogelated silk may include any number of tissues or regenerated tissue materials or medical devices and implants as well as any instrument, apparatus, appliance, material or other article that are used alone or in combination for diagnostic and/or therapeutic and/or surgical purposes and their proper application. For example, silk e-gel coating containing cell growth factor may be applied to skin tissue in vivo to promote burn wound healing. Exemplary medical devices and implants include devices and implants in dental applications such as dental filling materials, dental prosthetic devices (e.g., crowns, bridges, removable prostheses), dental implants (e.g., osseointegrated implant), and orthodontic appliances (e.g., dental braces or retainer); devices and implants in orthopaedic applications such as bone filling materials, arthroplasty devices (e.g., hip and knee prostheses), orthopedic implants (e.g., hip, knee, shoulder and elbow prosthesis, bone cements, prosthetic joint components), maxillofacial implants and devices (e.g., skull, face, and jaw prostheses), spinal devices or implants (e.g., spinal cord, spinal column, spine cage) and osteosynthesis devices and instrumentation for fixation of bones and/or joint components (e.g., nails, wires, pin, plates, rods, wires, screws or other fixators); devices and implants in traumatology applications such as wound healing devices or implants (skin, bone, and vascular wound grafts and patches, sutures, vascular wound repair devices, hemostatic dressings); cardiovascular devices and implants such as blood vessel prosthesis, stents, catheters, vascular grafts, heart valves and pacemakers; coagulation devices such as argon enhanced coagulation devices with coated probes; implantable artificial organs (e.g. artificial heart, liver, kidney, lungs, brain pacemaker and the like); or other small implantation materials such as occluders, filters, screws, bolts, nuts, pins, plates, gears, sleeve bearings, washers, anchors (for suture and/or tendon anchoring), plugs, nails and the like. Additionally, medical instruments such as scalpels, forceps, scoops, currettes, steotomes, chisels, gouges, strippers and the like may be coated with a silk e-gel and active agent such as antibiotic or anticoagulation drugs may be embedded in the silk e-gel coating to further effect patient outcomes. Likewise, veterinary implants, devices, and instruments may also include a silk fibroin gel in accordance with the present invention.

The substrate for coating of the electrogelated silk can be any materials that are suitable to be coated with silk gel through the electrogelation process. For example, the substrate may be electrically conductive materials such as metals, alloys, electrical conductive polymers or ceramics, or combination thereof. Exemplary metals or alloys for producing the devices and implants include, but not limited to, palladium, titanium, gold, platinum, silver, niobium, stainless steel, nickel, tin, copper, tantalum or alloys thereof, cobalt-chromium alloys, or Vitallium (CoCrMo alloy). Exemplary polymers for producing the devices and implants include, but are not limited to, silicones (breast prostheses, pacemaker leads), polyurethanes (pacemaker components), polymethacrylates (dental prostheses, bone cements), poly (ethylene terephthalate) (vascular grafts, heart valve sewing rings, sutures), polypropylene (sutures), polyethylene (prosthetic joint components), polytetrafluoroethylene (vascular prostheses), polyamides (sutures) and polylactides and poly (glycolic acids) (bioresorbables). Exemplary ceramic materials for producing the devices and implants include, but not limited to, metal oxides (alumina, zirconia) that are generally used in joint replacements and dental prostheses; Other materials such as materials based on calcium phosphate (bone fillers) and materials based on pyrolytic carbon (heart valves) may be also be used as the substrate for silk e-gel coating.

Optionally, one or more active agents may be embedded in a silk e-gel coating to be used as a functional coating. Alternatively, active agents can be loaded onto a pre-formed silk e-gel coating. The pre-formed silk e-gel coating may or may not contain an active agent, and the active agent in the pre-formed silk e-gel may or may not be the same as the active agent to be loaded onto the pre-formed silk e-gel coating. Alternatively, an active agent may be coated to the substrate as the first layer coating before the electrogelation process and a silk e-gel layer may be subsequently coated on the active agent-coated substrate. The active agent then will not be released until the silk e-gel is degraded. The active agents may be present as a liquid, a finely divided solid such as drug particles or any other appropriate physical form.

The active agent may be a therapeutic agent or a biological material such as the agents described above. By coating tissues or medical devices with the silk fibroin gel of the present invention, the tissue or device may provide further benefits than a similarly uncoated tissue or device. For example, wounded skin tissue may be coated with silk e-gel coating containing at least one cell growth factor (e.g., epidermal growth factor) to promote burn wound healing. Such silk e-gel coating process of wounded silk tissue may be performed in vivo to stimulate cells to re-epithelialize the wound. Alternatively, the silk e-gel coating process may also be performed in vitro on tissues or regenerated tissues for subsequent implantation. In another example, an implant may be coated with a silk e-gel containing an antibiotic or anti-inflammatory drug. Upon implantation, the gel may dissolve, and the antibiotic or anti-inflammatory drugs may be released as near to the incision or implant area as possible to achieve the lowest surgical site infection rates. Additionally, a drug embedding silk e-gel coated medical device or implant may reduce the need to frequently administer a drug to maintain adequate therapeutic concentrations.

Electrogelation has been shown herein to be reversible. In simple terms, electrogelation involves the conversion of a solubilized random-coil silk solution into a gel with significant silk I content by the application of an electric field via DC voltage. When the DC voltage is reversed (reversal of the electrode polarity), the silk gel tends to convert back to the random coil conformation. Indeed, the reversing process may be driven to near completion, and the electrogelation/reversing process can be repeated many times. Importantly, the nature of the silk material changes dramatically when alternating from the gel state to the liquid silk solution state: The gel has a very sticky, thick, mucus-like consistency. The liquid silk solution is not sticky at all and has a very low viscosity compared to the gel. The electrogelated silk, therefore, can be used as an active silk muco-adhesive, analogous to the slime secretion that snails and slugs utilize for motion and for securing themselves to various surfaces.

Other materials exhibit the ability to change stiffness or consistency based on the addition or subtraction of external energy or fields. For example, a class of fluids, commonly known as "smart fluids", are capable of changing properties in the presence of an electric or magnetic field. Typically, the fluid viscosity is modified with the presence and/or strength of the field applied. Additionally, magneto-rheological fluids contain a suspension of magnetic particles that align in the presence of a magnetic field. The fluid viscosity is effectively increased due to the alignment. Electro-rheological fluids consist of non-conducting particles that are suspended in an insulating fluid. The fluid viscosity can change dramatically in the present of an electric field. Further, thermoresponsive polymers can display material property changes with temperature change, such as solubility state and size.

Another aspect of the present invention relates to muco-adhesives. Typically polymers, these materials can be prepared as hydrogels, films, microspheres, sponges, tablets, or microtablets. Because of their potential for excellent adhesion to multiple surfaces, including wet surfaces, one application area has been in controlled and local drug delivery. MUCOAD™ (non-toxic, non-irritating, liquid muco-adhesive carrier, Strategic Pharmaceuticals Co., Washington, D.C.), is based on the hypromellose [hydroxypropyl methylcellulose (HPMC)] polymer. This product apparently has a high affinity to the mucosa and prolongs time of contact between a drug and mucosal tissue. It has potential for intranasal, ophthalmic (e.g., help relieve dry eye), vaginal, and rectal applications.

Further, a biologically-inspired robot that uses the friction of muco-adhesives to perform colonoscopies is being developed. Using balloon-like actuators to drive snail-like movement within the colon, the biological robot design relies on the use of materials at the robot-colon interface that provide the correct amount of friction and/or adhesion. This application employs a solid muco-adhesive film known as CARBOPOL® crosslinked acrylic acid-based polymer (NOVEON® Consumer Specialties, Wickliffe, Ohio), a high molecular weight cross-linked polymer of acrylic acid. This material can attach to mucus with physical bonds that form quickly. CARBOPOL® polymer may be used in tape form and successfully adhere to a pig colon, although shear damage limits the tape to single use application. Thus, every step of the robot required that new tape be dispensed (Dodou et al., Proc. 12th Int'l Conf Adv. Robotics 352-59 (Seattle, Wash., 2005). Water could be introduced to overcome the force of friction, allowing the tape to be disengaged. Dadou et al., 15(5) Minimally Invasive Therapy 286-95 (2006).

Although controlled drug delivery systems are available and significant progress has been made, there is still a significant need for systems that administer drugs in a manner that precisely matches physiological needs. Moreover, there is a need for tools to deliver peptide and protein drugs. Hydrogels have been used in drug delivery systems, protecting the drug and allowing controlled drug release through changes in gel structure driven by external stimuli. Stimuli that affect hydrogels include temperature, electric fields, solvent composition, light, pressure, sound, magnetic fields, pH, and ion introduction. Temperature-sensitive polymers, such as poly(N-iso-propylacrylamide) (PNIPAAm) and Poly(N,N-diethylacrylamide) (PDEAAm) are used extensively. Poly(propylene oxide) PPO and poly(ethylene oxide) PEO block copolymers have been used in controlled drug delivery based on sol-gel conversion at body temperature (e.g., PLURONICS® block copolymers, BASF).

Another class of stimulus-sensitive hydrogels are electro-sensitive hydrogels. Such hydrogels, which are also typically pH-sensitive, are usually made of polyelectrolytes and undergo shrinking or swelling in the presence of an applied electric field. Such materials have been applied in drug delivery. For example, hydrogels of poly(2-acrylamide-2-methylpropane sulfonic acid-co-n-butylmethacrylate) were used to release edrophonium chloride and hydrocortisone in a pulsatile manner using an electric current in distilled-deionized water. Electric fields have also been used to control erosion of hydrogels made of poly(ethyloxazoline)-PMA complex in saline solution. Typically, these hydrogels may also be actuated with an external electrical field. One of the limitations is difficulty in achieving the response in electrolytes; in other words, under physiological conditions. Oui & Park, 53 Adv. Drug Deliv. Rev. 321-39 (2001). Chemically crosslinked hyaluronic acid (HA) hydrogels have also been shown to be electro-sensitive. Using an electric field, pulsed release of negatively charged macromolecules can be achieved. Tomer et. al., 33 J. Contr. Release 405-13 (1995)).

Figure 39B:
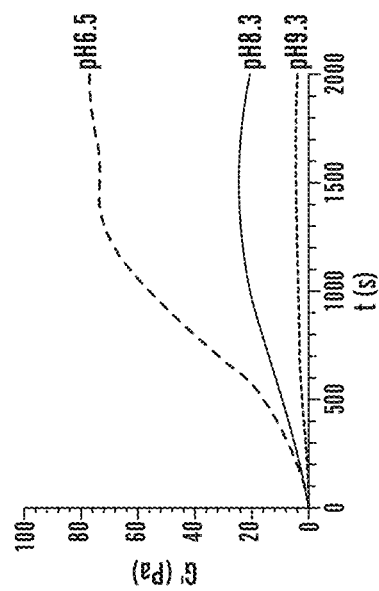
FIGS. 39A-39B are graphs showing the dependence of electrogelation kinetics on protein concentration (FIG. 39A) and solution pH (FIG. 39B) (for a silk concentration of 4.8 wt. %) at a field strength of 9 V/mm.

The versatility of silk and availability of different forms, conformations, and processing techniques opens up a wealth of potential application areas. FIG. 39 provides a brief overview of the processing strategies, predicted properties, and potential application areas. Note that processing techniques may be performed in sequence. The process labeled "Egel" is the electrogelation process described herein. Vibration can be applied in the form of high-intensity energy generated by an ultrasonicator or lower-intensity energy generated by an electric toothbrush-style actuator. Shearing force can be provided by straining a material through hands-on manipulation or by extruding it through an orifice (flow-induced shear). An oven may be used to effect fast drying, although a room-temperature process provides slow drying. It should be noted that this is not meant to be an exhaustive list, but to provide a context for the electrogelation process. Other processing techniques, such as pH modification, methanol treatment, and water annealing are also used to achieve desired silk outcomes.

Based on results of experiments and experience working with silk and silk-based materials, it is clear there are many potential applications of active silk muco-adhesives described herein, including robotic applications (non-biomedical) and biomedical applications.

There are many applications in the area of robotics for a material that can transition from very sticky to non-sticky. Wall- and ceiling-climbing robots are being pursued for applications that range from military and police surveillance to explosives placement, as well as for green chemistry adhesive and related applications. Active silk muco-adhesives would have a direct application in providing a controlled adhesion to walls and ceilings. The properties of the adhesive gel created through electrogelation seem to mimic the slime that land snails (e.g., *Helix lucorum*) produce. These snails extrude the slime out of their underside, creating a slimy path on which they crawl. In addition, these animals extrude a slightly more adhesive version of the slime to anchor themselves to leaves, rocks, or other surfaces. In the snail, locomotion is achieved through a wavelike response in its muscular foot (underside). The back section of their foot pushes forward, sliding in the slime. When stopped, the foot sticks in place. The section of foot in front of the stuck section then slides forward in the slime. In this way, the snail or slug slowly moves forward along the slime trail.

This method of locomotion may be easily utilized with the silk muco-adhesive, because the silk muco-adhesives can be utilized in two ways: providing a sticky slime that a robot can crawl along and as an adhesive anchoring system. This application does not need to take advantage of reverse gelation. In other words, the adhesive does not need to be active. A second form of locomotion can be achieved with the use of active adhesion. For example, individual robot 'feet' can contain small dispensers and electrogelation coils. When the robot needs to stick to a wall or ceiling, silk solution can be extruded through the appropriate dispenser and converted to gel through electrogelation. When the foot needs to be removed from the wall, reverse electrogelation converts the gel back to a liquid, eliminating the adhesion.

In surveillance applications, it can be important to stay in place for a long period of time. It is also important that on-board energy is not wasted in maintaining a position for this period of time. Silk muco-adhesives can be used to anchor a robot or other devices to various surfaces for an extended period. Electrogelated silk gel can adhere an object temporarily if reverse electrogelation or an applied force causes disruption of adhesion. It can also be used for long-term adhesion. It has been shown that an object can adhere to a painted wall surface for days and potentially weeks without expending energy. The limiting factor is potentially the length of time for the silk material to degrade. Another application area in robotics is in terms of payloads. The mission of a robot might be to deliver a camera, antenna, or other device for surveillance. Silk muco-adhesive can be used to anchor any such device to a wall for short-term or long-term surveillance. One strategy can be to have the robot extrude a steady stream of electrogelated silk with a fine wire embedded. The wire would adhere to the wall because of the muco-adhesive and act as an antenna.

Active silk muco-adhesives open up a range of missions for robots that heretofore have not been fully explored. Small-sized, snail-like robots can be constructed that fundamentally are based on the slime-dependent motion of snails. Like snails, silk muco-adhesives can allow a robotic snail to adhere to a variety of surfaces, ranging from smooth to rough. The types of surfaces can include glass, acrylic, wood, painted walls, cement, rocks, dirty and dusty surfaces, to name a few. Such robots could be used to: inspect the inside or outside of pipes, even with the presence of fluids; be used in forested areas to detect the intensity and presence of fires; help in rescue situations, such as collapsed houses or mines; be utilized on building surfaces or various natural surfaces, such as trees or rocks, to take data during severe weather, like tornados; be deployed in animal preserve areas to track endangered animals; or attach to animals in a temporary manner to allow study. Police or other rescue services could throw miniature versions of the robot against walls or road signs to provide a temporary method of gaining information, such as wireless video feeds.

Using this approach, a silk muco-adhesive was used to attach a surveillance platform to a wall. The platform contained a wireless video camera that streamed live images to a laptop, while a remote controller was used to move the camera on a motorized pivot. The controller was also used to provide controlled reverse gelation, which caused the platform to be gravity-fed down a surface. Because of the unique ability of silk muco-adhesive to adhere to underwater surfaces, a robot using a silk muco-adhesive in accordance with the present invention can perform many underwater missions: inspection of oil platforms and other underwater structures; covert attachment to boats and subs for surveillance and communication interception; and surveying of riverbeds and water floors. Perhaps swimming robots could use homing devices, such as sound or temperature sensors to find a ship, then attach via electrogelation; repair or reconnaissance missions could then be carried. To accommodate longer-duration missions, silk solution maintained at a high pH can be carried in on-board storage, the higher pH extending the longer storage-life of the silk.

Additionally, there is a wide range of biomedical application areas for active silk muco-adhesive. Given the tremendous potential to create a snail-like robot, a biomedical version can be created for medical diagnostics or treatment. For instance, a miniature version can enter the body either through swallowing or insertion through a small incision. The biomedical robot can move in, on, or around organs through adhesive locomotion. The ability to adhere to wet surfaces allows the robot to position itself near damage or diseased locations. Sensors or a camera can be used to relay critical information to medical personnel. Silk gel, stored inside the robot, can be deposited at a damage site, providing an initial temporary repair. The gel can contain drugs, growth factors, antibiotics, or other bioactive ingredients to encourage healing. In conjunction with other functionality, such as the application of vibration or the use of therapeutic ultrasound, the gel patch (in silk I conformation) can be manipulated into a beta-sheet conformation. In this form, the patch is considerably stronger and water insoluble. This allows the patch to have longer-term duration. The material can also be used on burns, wounds, or other locations on the outside of a body. Like for the internal applications, bioactive ingredients can be incorporated for improved healing, and the material is soothing and assists in protecting against infection and contamination. In another biomedical application, silk muco-adhesives can also be used to anchor a pill or other drug-release product to mucosa layers of various tissues. This provides the ability for sustained drug delivery.

Silk muco-adhesive can be useful in robotic design. Many key components in a biomedical robot that explores the inside of a human can take advantage of such materials. Electrogelated silk may also be important as an actuator. When silk solution is electrogelated, there is a stiffness change and also possibly a volume change. These characteristics can be exploited to make an actuator. In one embodiment, silk solution and gel can be used to adjust the angle of a plate. When the plate is used to support a miniature camera, the process can create motion without using a traditional mechanism. Another actuator design consists of a flexible tube or bladder-supported tube. When the silk solution changes volume during electrogelation, the tube can be actuated like a wagging finger. In all of the biomedical applications, the use of silk materials allows slow degradation over time, obviating the need for removing the device from the body.

Further, the systems above can be used to lay down fiber optic cable inside the body in the form of silk fiber optics. Because, as reported previously, silk fibers can serve as light guides, this embodiment offers options for in vivo imaging that provides new windows into healing, treating wounds, cancers or vessel deposits, and many related needs.

Aside from the robotic and related fields outlined above, these systems are useful in consumer related products such as toys, science projects, and new forms of artwork among others. Further, the option to functionalize the carrier to deposit, secrete or lay down new materials suggests options in remote construction, sealing actions, hazardous sites, boat hulls, and many other related applications on land, at sea, and in the air.

Another aspect of the invention relates to methods and compositions for preparing silk pH-gels. The term "Silk pH-gels" or "adhesive silk gels" herein refers to silk gels formed due to increased bulk or local proton concentration of the silk fibroin solution (or reduced local or bulk pH level), thereby forming adhesive silk hydrogels.

In one embodiment, the invention relates to a method of preparing an adhesive comprising a silk-based gel. The method comprises reducing pH level of a silk fibroin solution thereby forming an adhesive comprising a silk-based gel.

Any technique that can result in increased bulk or local proton concentration of silk fibroin solution can be used to induce the adhesive silk pH-gels. For example, pH of the silk fibroin solution can be directly titrated by an acid to reduce the pH level of the silk fibroin solution to an acidic pH, thereby forming the adhesive silk pH-gels. See, Example 30 and 31 for preparation and characterization of exemplified adhesive pH-gels by pH titration (i.e., pH-gels). Alternatively, pH level of the silk fibroin solution can be locally and indirectly reduced by electrolyzing a silk fibroin solution to locally increase the proton concentration of the silk fibroin, thereby forming the adhesive silk pH-gels. See, Example 31 for preparation and characterization of exemplified adhesive silk pH-gels by electrogelation (i.e., e-gels).

Accordingly, silk pH-gels herein can include silk gels that are induced by reducing pH, either due to direction pH titration or due to indirect pH change, for instance, due to the electrolysis by electrogelation process described herein, thereby resulting increased proton concentration of silk fibroin solution, either locally or in bulk solution. Hence the silk pH-gels herein can also include the silk e-gels in a broader definition, because these adhesive silk gels can all be induced by increasing the bulk or local proton concentration of silk fibroin solution, and may present similar physical or chemical characteristics. For example, Example 31 showed that the essential adhesive properties of the adhesive silk gels prepared by electrogelation of the silk fibroin solution can be captured by adhesive silk gels prepared by pH titration of the silk fibroin solution.

In one embodiment, the adhesive silk pH-gel is formed by reducing the local pH or bulk pH of the silk fibroin solution to an acidic pH, for instance about 6 or less, about 5 or less, about 4 or less, about 3 or less, about 2 or less, about 1.5 or less, or about 1 or less.

Adhesion of two dissimilar surfaces can be described by different theories, such as electronic, adsorption, wetting, diffusion (interpenetration) and fracture theories (Kinloch, 1980). For example, formation of an intimate molecular contact at the interface between two adhering surfaces may be necessary for adhesion (Kinloch, 1980).

The overall molecular conformation of adhesive silk gels may be partially similar to that of the solution state, i.e., presenting an unordered secondary structure in the gel systems. The adhesive pH-gel formation can be mainly due to physical, entanglement crosslinks and possible helical interactions between silk fibroin chains that are not associated with significant β-sheet formation.

The amorphous-rich structure and the hydrophilic nature of the pH-gels (as compared to the other silk gels, such as hydrophobic, β-sheet rich sonicated gels) and their strong viscoelastic properties can aid in the initial wetting and formation of a good interfacial contact between the gel and the surface of a subject. Once intimate contact is achieved, strong adhesion can be formed due to adsorption, i.e., adhesion due to surface forces acting between the gels and surface of the subject (e.g., a surface oxide layer). These surface forces may include hydrogen bonding due to the amide groups of the protein, and van der Waals interactions due to main chain and side chain polar groups, mobile ions and the residual surface charge.

The adhesive silk pH-gel according to the methods of the invention therefore has an enhanced viscoelastic property that can provide an intimate contact with a surface of a subject and physically or chemically interact with a component of the subject, thereby adhering to the subject by forming a bonded interface with the subject.

In one embodiment, the adhesive silk pH-gel adheres to a surface of a subject with a work of adhesion (WOA) of the adhesive to the surface of the subject being at least about 0.05 mJ.

In one embodiment, the adhesive silk pH-gel adheres to a surface of a subject with a work of adhesion (WOA) of the adhesive to the surface of the subject being at least about 1 mJ.

In one embodiment, the adhesive silk pH-gel adheres to a surface of a subject with a work of adhesion (WOA) of the adhesive to the surface of the subject being at least about 4 mJ.

The adhesive silk pH-gel can be used as bioadhesive to attach or adhere to hydrocolloids on biological tissues or organs.

In one embodiment, the adhesive silk pH-gel can be used as mucoadhesive to adhere to a mucosal surface. Mucoadhesion can involve, for instance, the formation of an intimate contact between the adhesive material and the mucus through wetting and swelling of the material (not necessary for a fully hydrated hydrogel); interpenetration of the adhesive and mucin chains and formation of entanglements; and possible formation of weak chemical bonds. Hydrogel characteristics such as high hydrogen bond formation propensity, high concentration of negative charge, high polymer molecular weight to increase entanglements with the mucin chains, high polymer chain flexibility to enable penetration into the mucus network and adequate surface free energy to enable proper wetting of the mucosal surface have been shown to increase mucoadhesion (Mathiowitz et al., 1999), while additional requirements include biocompatibility, non-toxicity and other factors. The adhesive silk gels of the invention satisfy the above discussed criteria and hence are suitable to be used as mucoadhesives. Further, silk e-gels (or pH titrated gels) may be used in applications such as biomimetic dynamic adhesion (Peattie, 2009) through engineering of reusability into their inherently reversible and substrate tolerant nature (Leisk et al., 2009).

Accordingly, some embodiments of the invention also provide methods of attaching or adhering an adhesive silk-based gel to a surface of a subject. The method comprises exposing the subject to a silk fibroin solution; and reducing pH level of the silk fibroin solution thereby forming an adhesive comprising silk-based gel, wherein the silk-based gel adheres to the subject. The subject can be any subject needs to be adhered to. When used as bioadhesive, the subject can be a biological tissue or organ. The subject can also be anything that presents a mucosal surface.

In one embodiment, the adhesive silk gels may contain at least one active agent. The silk fibroin can be mixed with the active agents prior to forming the gels, or the active agent can be loaded into the silk gels after it is formed.

The active agent can represent any material capable of being incorporated in the adhesive silk gels. For example, the agent may be a therapeutic agent, or a biological material, such as cells (including stem cells), proteins, peptides, nucleic acids (e.g., DNA, RNA, siRNA), nucleic acid analogs, nucleotides, oligonucleotides, peptide nucleic acids (PNA), aptamers, antibodies or fragments or portions thereof (e.g., paratopes or complementarity-determining regions), antigens or epitopes, hormones, hormone antagonists, growth factors or recombinant growth factors and fragments and variants thereof, cell attachment mediators (such as RGD), cytokines, enzymes, small molecules, drugs, dyes, amino acids, vitamins, antioxidants, antibiotics or antimicrobial compounds, anti-inflammation agents, antifungals, viruses, antivirals, toxins, prodrugs, chemotherapeutic agents, hemostatic agents, or combinations thereof. See, e.g., PCT/US09/44117; U.S. Patent Application Ser. No. 61/224,618). The active agent may also be a combination of any of the above-mentioned agents. Encapsulating either a therapeutic agent or biological material, or the combination of them, is desirous because the encapsulated product can be used for numerous biomedical purposes.

In some embodiments, the active agent may also be an organism such as a fungus, plant, animal, bacterium, or a virus (including bacteriophage). Moreover, the active agent may include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, and precursor cells. The active agents can also be the combinations of any of the cells listed above. See also WO 2008/106485; PCT/US2009/059547; WO 2007/103442.

Exemplary antibodies that may be incorporated in silk fibroin include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab. The active agents can also be the combinations of any of the antibodies listed above.

Exemplary antibiotic agents include, but are not limited to, actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics.

Optionally, the antibiotic agents may also be antimicrobial peptides such as defensins, magainin and nisin; or lytic bacteriophage. The antibiotic agents can also be the combinations of any of the agents listed above. See also PCT/US2010/026190.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like. Interactions between components may also be used to functionalize silk fibroin through, for example, specific interaction between avidin and biotin. The active agents can also be the combinations of any of the enzymes listed above. See e.g., PCT/US2010/042585.

When introducing therapeutic agents or biological material into the adhesive silk gels, other materials known in the art may also be added with the agent. For instance, it may be desirable to add materials to promote the growth of the agent (for biological materials), promote the functionality of the agent after it is released from the adhesive silk gels, or increase the agent's ability to survive or retain its efficacy during the period it is embedded in the adhesive silk gels. Materials known to promote cell growth include cell growth media, such as Dulbecco's Modified Eagle Medium (DMEM), fetal bovine serum (FBS), non-essential amino acids and antibiotics, and growth and morphogenic factors such as fibroblast growth factor (FGF), transforming growth factors (TGFs), vascular endothelial growth factor (VEGF), epidermal growth factor (EGF), insulin-like growth factor (IGF-I), bone morphogenetic growth factors (BMPs), nerve growth factors, and related proteins may be used. Growth factors are known in the art, see, e.g., Rosen & Thies, CELLULAR & MOLECULAR BASIS BONE FORMATION & REPAIR (R. G. Landes Co., Austin, Tex., 1995). Additional options for delivery via the adhesive silk gels biomaterial include DNA, siRNA, antisense, plasmids, liposomes and related systems for delivery of genetic materials; peptides and proteins to activate cellular signaling cascades; peptides and proteins to promote mineralization or related events from cells; adhesion peptides and proteins to improve silk-PEGs-tissue interfaces; antimicrobial peptides; and proteins and related compounds.

Silk fibroin in the adhesive silk gels can be chemically modified with active agents, for example through diazonium or carbodiimide coupling reactions, avidin-biodin interaction, or gene modification and the like, to alter the physical properties and functionalities of the silk protein. See, e.g., PCT/US09/64673; PCT/US10/41615; PCT/US10/42502; U.S. application Ser. No. 12/192,588.

The adhesive silk gels can also contain one or more biocompatible and/or biodegradable polymers blended with silk fibroin. For example, additional biopolymers, such as chitosan, exhibit desirable mechanical properties, can be processed in water, blended with silk fibroin, and form silk matrix. Other biopolymers, such as collagen, gelatin, agarose, chitin, polyhydroxyalkanoates, pullan, starch (amylose amylopectin), cellulose, alginate, fibronectin, keratin, hyaluronic acid, pectin, polyaspartic acid, polylysin, pectin, dextrans, and related biopolymers, or a combination thereof, may be utilized in specific applications, and synthetic biodegradable polymers such as polyethylene oxide, polyethylene glycol, polylactic acid, polyglycolic acid, polycaprolactone, polyorthoester, polycaprolactone, polyfumarate, polyanhydrides, and related copolymers may also be selectively used. The polymer selected herein to be blended into the silk matrix should not negatively impact the crosslinking ability or adhesive properties of the adhesive silk gels The adhesive silk gels, when embedded with active agents or biological materials, may be suitable for long term storage and stabilization of the active agents. Cells and/or active agents, when incorporated in the adhesive silk gels, can be stable (i.e., maintaining at least 50% of residual activity) for at least 30 days at room temperature (i.e., 22° C. to 25° C.) and body temperature (37° C.). Hence, temperature-sensitive active agents, such as some antibiotics or hemostatic agents, can be stored in adhesive silk gels without refrigeration. Importantly, temperature-sensitive bioactive agents can be delivered (e.g., through injection) into the body through the adhesive silk gels and maintain activity for a longer period of time than previously imagined. See, e.g., PCT/US2010/026190.

The adhesive silk gels with embedded active agents (e.g., therapeutic agents) can be suitable for biodelivery. Techniques for using silk fibroin as a biodelivery device may be found, for example, in U.S. patent application Ser. No. 10/541,182; Ser. No. 11/628,930; Ser. No. 11/664,234; Ser. No. 11/407,373; PCT/US07/020,789; PCT/US08/55072; PCT/US09/44117. Some embodiments of the present invention relate to the utility of adhesive silk gels with embedded therapeutic agents or biological materials as drug delivery systems for potential utility in medical implants, tissue sealants, and tissue repairs such as wound dressing.

A further aspect of the invention provides a method for producing a multi-layered silk-based gel. The method includes (a) reducing pH level of a first silk fibroin solution thereby forming a silk-based gel; (b) transferring the silk-based gel from step (a) to a second silk fibroin solution; (c) reducing pH level of the second silk fibroin solution, thereby forming a new layer of silk-based gel on an outer surface of the silk-based gel from step (a); and (d) repeating steps (b) and (c) thereby forming a multi-layered silk-based gel.

As used herein, the term "multi-layered" refers to at least two layers of silk-based gel. The number of layers of silk-based gels depends upon an application or an user's preference. For example, if a thicker silk-based gel is desirable, e.g., for enhanced mechanical strength, the preformed silk-based gel can be put into a new silk fibroin solution in order to form an additional layer of silk-based gel.

In some embodiments, the multi-layered silk-based gel can further comprise at least one active agent. In some embodiments, at least one silk-based gel layer further comprises one or more active agent, e.g., by adding the active agent into the silk fibroin solution during gel formation. The active agent in different silk-based gel layer can be the same or different. By embedding one or more active agents in different silk-based layers, various active agents can be released at a different rate or at a different time. For example, an active agent embedded in an outer layer of a multi-layered silk-based gel will be likely released from the multi-layered silk-based gel of the invention at a faster rate than an active agent embedded in an inner layer. Examples of active agents include, without limitation, cells, proteins, peptides, nucleic acids, nucleic acid analogs, nucleotides or oligonucleotides, peptide nucleic acids, aptamers, antibodies or fragments or portions thereof, antigens or epitopes, hormones, hormone antagonists, growth factors or recombinant growth factors and fragments and variants thereof, cell attachment mediators, cytokines, enzymes, antibiotics or antimicrobial compounds, viruses, toxins, prodrugs, chemotherapeutic agents, small molecules, drugs, and combinations thereof.

In some embodiments of a multi-layered silk-based gel, the percent of silk fibroin in each layer can vary, e.g., to control the release rate of the active agent from the layer, by using different percent of silk fibroin solution. Thus, multi-layered silk-based gels can be used for controlled release of at least one active agent.

In some embodiments, the multi-layered silk-based gel can further comprise one or more biocompatible and/or biodegradable polymers. The biocompatible and/or biodegradable polymers can be blended with silk fibroin, or they can be an individual layer in contact with a silk fibroin layer.

The structure of adhesive silk gels enables a controlled release of the delivery of the embedded active agents (e.g., therapeutic agents or biological materials). The techniques of controlled release of active agents from the adhesive silk gels are similar as discussed herein in the embodiments for silk e-gel.

A pharmaceutical formulation may be prepared that contains the adhesive silk gels having encapsulated bioactive agents (e.g., therapeutic agent). The compositions of the pharmaceutical formulation and the techniques of preparing and administering the pharmaceutical formulation are also similar as discussed herein in the embodiments for silk e-gel.

The silk pH-gels herein present desirable properties for application as bioadhesive such as tissue sealants: strong adhesive properties, good biocompatibility, adjustable biodegradability and side-product free chemistry.

The silk pH-gels formed as a bioadhesive at the wound site may further contain hemostatic agents since hemostatic agents typically act to stop bleeding and the silk adhesive can bind to and close defects in the tissues. Combining the hemostatic agents into the adhesive silk gels can therefore present desirable features during surgical repair to prevent or stop bleeding as well as promote tissue reconstruction. Exemplary hemostatic agents suitable for use herein include, but are not limited to, thrombin, fibrin, fibrinogen, gelatin, collagen, polysaccharide, cellulose, blood factors, and combinations thereof.

The embodiments of the invention also relate to applications of adhesive silk gels in other areas such as using silk pH-gels to prepare cosmetic compositions, cosmetic surgery materials, medical implants, tissue engineering materials and the like, as described in the embodiments of silk e-gel herein.

In some embodiments, an adhesive silk gel can be integrated into a microfluidic device, e.g., Lab-on-a-chip or Pharmacy-on-a chip such as the ones disclosed in U.S. Pat. Nos. 5,797,898 and 7,226,442. For example, in a microfluidic device with reservoirs containing active agents, the silk-based gel can be used as a permeable membrane over the reservoirs to control the release of active agents. In some embodiments, due to its adhesive property, it can be used to trap particles, e.g., proteins or cells, while flowing a fluid across a channel of the microfluidic device.

Further, because silk pH-gel may present inherently reversibility (e.g., the adhesive property is reversible for silk e-gels), the adhesive pH-gel may be used in applications such as biomimetic dynamic adhesion (Peattie, 2009) through engineering of reusability into their inherently reversible and substrate tolerant nature (Leisk et al., 2009). For example, a surveillance platform such as using a soft robot containing the adhesive silk gels of the invention was described in the embodiments of silk e-gel herein.

In various embodiments, a silk pH-gel can be reconstituted in a solution, e.g., by redissolving the silk pH-gel in a solution, e.g., buffered solution, saline and water.

EXAMPLES

Example 1

Parallel Electrode Gelation

Stock aqueous solutions of solubilized silk fibroin as were prepared as described previously. Sofia et al., 54 J. Biomed. Mater. Res. A 139-48 (2001). See U.S. patent application Ser. No. 11/247,358, WO/2005/012606, and WO/2008/127401. Briefly, cocoons of B. mori were boiled for 20 min in an aqueous solution of 0.02 M sodium carbonate, and then rinsed thoroughly with pure water. After drying, the extracted silk fibroin was dissolved in a 9.3 M LiBr solution at 60° C. for 4 hr, yielding a 20% (w/v) solution. The resulting solution was dialyzed against distilled water using Slide-A-Lyzer® 3.5K MWCO dialysis cassettes (Pierce, Rockford, Ill.) for three days to remove the residual salt. The solution was optically clear after dialysis and was centrifuged twice at 10,000 rpm for 20 min to remove silk aggregates as well as debris from original cocoons. The final concentration of silk fibroin aqueous solution was approximately 8% (w/v). This concentration was determined by drying the solution with a known volume and weighing the residual solid. The 8% silk fibroin solution was stored at 4° C. and diluted with ultrapure water before use. The silk fibroin solution may be diluted or concentrated to a higher concentration. To obtain a silk fibroin solution with a higher concentration, the silk fibroin solution with a lower concentration may be dialyzed against a hygroscopic polymer, for example, PEG, a polyethylene oxide, amylose or sericin. For example, an 8% silk fibroin solution may be dialyzed against 10% (w/v) PEG (10,000 g/mol) solution.

Figure 4:
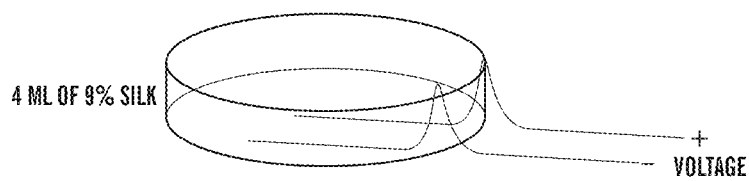
FIG. 4 presents a schematic of a parallel electrode electrogelation setup.

Two parallel wires (electrodes) were placed along the bottom of a 70 mm diameter plastic culture dish that contained 4 ml of ~9% silk fibroin solution, as shown in FIG. 4. The liquid level was slightly above the top of the electrodes and the electrodes were approximately 40 mm apart. A voltage of 22.2 VDC was applied using a high-current Li-Pol battery. FIGS. 5A, 5B, and 5C shows photos of the initial experiment at time points of 0 min, 20 min, and 275 min, respectively. As shown in FIG. 5A and FIG. 6, almost immediately upon applying the potential, gelation began at the positive electrode (+) and bubbles formed at the positive (+) and negative (−) electrodes. As shown in FIG. 5B, over the first 30 min of electrogelation, the gelation process continued, with steady growth of a "gel front" that emanated from the positive electrode (+) in the general direction of the negative electrode (−).

On closer inspection, radial patterns could be seen within the gelation zone, emanating from the positive electrode and pointing in the general direction of the negative. After about 30 min, gelation continued, but at a slower rate. The bubbles that formed on the positive electrode (+), likely oxygen gas, would become permanent features within the gel, as the solid formed around them. The barrier formed by the permanent bubbles on this electrode may play a key role in the decrease in the rate of gel front growth. Bubbles on the negative electrode (−), likely hydrogen gas, formed constantly, but also dissipated somewhat as their gaseous contents reached the silk solution surface. In all cases, the rate of bubble formation was greater than the rate of dissipation. The consistency of the gelated silk was highly viscous (soft) and very tacky; similar to the consistency of thick mucus. After the culture dish was refrigerated overnight, the gelated silk was quite stiff.

Example 2

Parallel Electrode Gelation

The same parallel electrode experimental setup of Example 1 was used with ~9% silk solution, with the exception that a higher voltage potential of 74.9 VDC was applied across the electrodes to generate the electric field. This tested whether higher voltage accelerates the gelation process and possibly results in more complete gelation. FIGS. 7A, 7B, and 7C show experimental results at time points of 0 min, 15 min, and 30 min, respectively. As described earlier, a similar gelation process was witnessed. For example, radial patterns in the gelation front are clearly seen in FIG. 7B. With the higher voltage, the gelation front expanded at a higher rate, but it also appeared that the electrogelated silk was not as dense as witnessed using a lower voltage. Bubbles on the negative electrode formed at a much higher rate at this voltage, as evidence of an accelerated underlying reaction.

Example 3

Extrusion Test Characterizes Texture of Electrogelated Silk Fibroin

The ability to rapidly electrogelate a controlled volume of silk solution provides numerous practical applications. A gelated portion of silk generated after 5 hours of electrogelation was extracted and poured into a 10 ml syringe. Using a 1 mm diameter syringe needle attached, the gelated silk was extruded slowly. The silk material ejected from needle was much stiffer than when it was extracted from the dish. This effect can be caused by flow-induced shear as the silk is forced through the small diameter needle. When the electrogelated silk holds a meta-stable silk I conformation, extrusion through a needle causes the additional alignment necessary to convert the microstructure to β-sheet. Many qualitative observations were made from this initial extruded gelation sample. For example, the material was sticky, fairly stiff, quite elastic, and cool to the touch. In fact, the entire gelation process, from electrogelation to extrusion, appears to maintain silk temperature around room temperature. As the silk was extruded through the needle, the resulting extruded gel was ejected as a coherent stream. Upon extruding, the resulting material is translucent. After about 5 min when exposed to air, the color changed to an opaque white.

Example 4

Magnetic Fields

The methods in accordance with the present embodiments demonstrated that an applied electric field results in gelation of solubilized silk. The magnetic field induced by the applied electrical field is not a true cause of gelation, however. To demonstrate the magnetic field effect, a variation in the electrogelation setup was used. A positive ring-shaped electrode, best shown in FIG. 8C, was formed by wrapping a bare wire around the outside of a culture dish, while a straight wire was used as a negative electrode. The negative electrode was submerged within a ~9% silk solution, in the middle of the culture dish. To gauge the rate of gelation, a second experiment was conducted simultaneously using the parallel electrode setup used previously, shown in FIG. 8A as a control. Both experiments were conducted with a voltage potential of 24.8 VDC. As shown in FIG. 8B, even after 30 min, no visible gelation occurred using the ring-shaped electrode setup (magnetic field). The significant gelation that occurred in the parallel-electrode setup confirmed that the lack of gelation in the ring-shaped electrode setup was not due to issues with the silk, electrode materials, or voltage applied.

Example 5

Aluminum Tube-Based Electrode

Successful electrogelation was achieved with a ring-shaped electrode submerged within a culture dish. This configuration provided evidence that increased electrode surface area could lead to greater electrogelation rates and total volume. Additionally, aluminum tubes can be used as electrodes. In one embodiment, an aluminum tube, acting as a positive electrode, was mounted vertically inside a culture dish using hot glue. An exposed wire, acting as a negative electrode, was positioned concentrically with the cylinder. A schematic illustration of this experimental setup is shown in FIG. 9A. Observations from beneath the culture dish, comparing electrogelation times of 0 min, 7.5 min, and 15 min showed that electrogelation occurred quickly with this configuration, and resulted in conversion of at least 80% of the silk solution into gel.

To further understand the effect that electrode surface area has on electrogelation, another embodiment utilized two concentric aluminum tubes as electrodes. A schematic of this setup is shown in FIG. 9B. Both tubes were hot glued to the bottom of a culture dish, with ~9% solubilized silk filling the annular volume. This experiment resulted in very fast gelation dynamics, producing rapid gelation and bubble formation. Nearly 100% of the annular volume was gelated. Both tube electrode embodiments clearly demonstrate that maximizing electrode surface area is one key to increasing electrogelation rate and final gelation volume.

Example 6

Syringe-Based Metallized (Foil) Plunger Electrode Experiments

Given the success of the aluminum tube-based electrode embodiments, a separate embodiment utilized a syringe to both contain the silk solution and provide the necessary cylindrical electrode geometry to mimic the result of the aluminum tube-based electrode embodiment. In some syringe embodiments, the syringes were mounted vertically using standard lab stand hardware. In an initial design, aluminum foil was used to metallize the plunger of a 3 ml syringe. A syringe needle was inverted and positioned through the syringe nozzle, acting as the other electrode. Testing configurations were executed with the foil as the positive electrode or needle the negative electrode and vice versa. In either configuration, the electrogelation results were somewhat poor. This may be attribute to the limited foil surface area or poor electrical conductivity of the foil.

In an effort to improve electrogelation results with an aluminum foil-coated plunger, a 10 ml syringe plunger was modified. In this setup, the larger surface area of the plunger would be exploited to understand the effect of exposed area of the electrode. Very little electrogelation was witnessed, even after 30 min of voltage application.

Example 7

Syringe-Based Metallized (Plug) Plunger Electrode

Another syringe design substituted a ⅜" diameter aluminum plug for the aluminum foil. This plug was mounted into the plunger, with about ¼" of the length extended into the silk solution volume. A syringe needle was passed into the solution from the nozzle end of the syringe. As in aluminum foil embodiments, this design was tested in two configurations: with the plug as the positive electrode and needle the negative and vice versa. With the needle as the positive electrode, more gelation was evidenced. The gelation process was slow for both configurations, however. The limited surface area of both plug and needle is likely the reason.

Example 8

Syringe-Based Spring and Needle Electrode

A spring-shaped electrode geometry was constructed in another embodiment of the present application. A conducting wire was passed from the plunger side of the syringe through the plunger head. The wire, stripped of its insulation past the plunger head, was helically coiled to provide a significant number of turns within the syringe. The coil was designated the positive electrode. A needle was employed again as a negative electrode, with special attention paid to ensure no contact would be made between the positive and negative electrodes. FIGS. 10A-10C show the results of the electrogelation experiment after 0 min, 5 min, and 15 min, respectively. With the spring-shaped electrode acting as the positive electrode, very fast gelation was achieved, with almost 90% gel volume achieved after 15 min. This configuration is especially important due to the fact that the design does not hinder the extrusion of the gel from the syringe directly. When the syringe plunger is depressed, the spring-shaped electrode compresses, forcing the gel out of the syringe body. The gel was extruded from the syringe as a sticky, coherent stream, even though a syringe needle was not used. The use of a syringe needle can increase the gel stiffness further due to flow-induced shear.

Example 9

Parallel Electrode Experiment Comparing New (13 Days) to Older (65 Days) Solubilized Silk After silk is solubilized, it can eventually self-assemble over time. In self-assembly, conversion of the random coil nature of the silk solution is induced into conversion to β-sheet content, creating a stiff solid. Certain conditions, such as elevated pH and temperature, can accelerate the solidification. Using the parallel electrode configuration shown in FIG. 4 with 24.8 VDC, a comparison was made between silk that had been prepared 13 days compared with silk that had been prepared 65 days prior to the test. FIG. 11 shows the results after 0 min and 10 min of voltage application. While the older silk solution generated a larger volume of bubbles on the negative electrode, gelation appears to be faster in the newer silk.

Example 10

Parallel Electrode Experiment Comparing Oxidized to Non-Oxidized Electrode Wire To compare electrogelation rates as a function of oxidation, two simultaneous parallel electrode embodiments were constructed: one with electrodes that had been exposed to air for a prolonged period, the other with freshly exposed wire as electrodes. Only subtle differences were observed in this experiment. There was a brightness gradient in the gelated silk with the non-oxidized wire, while there was mostly bright white color throughout the gelated silk produced with the oxidized wire. It is possible that the brightness gradient occurs because the gelation is progressing faster using the non-oxidized wire. To confirm this observation, in situ electrical resistance and current measurements are made.

Example 11

Three (3) ml Syringe-Based Spring and Needle

A practical gelation delivery tool was fashioned on the syringe-based spring and needle concept. A 3 ml syringe is a relatively small size that provides nearly complete electrogelation within a 10 min timeframe. FIG. 12 shows that nearly 90% gelation was achieved over 10 min of voltage application. The resulting material could be readily ejected from the syringe in a coherent stream using the plunger. One interesting observation is that as bubbles formed at the top of the silk solution, enough pressure built up to push the syringe plunger downward.

Example 12

Electrogelation Using Parallel Copper Coil Electrode

The electrogelation process involves an electrochemical reaction that is produced by an electrochemical cell including a DC voltage source, metallic positive and negative electrodes, and the solubilized silk solution. Gelation via parallel copper electrodes in solubilized silk confirmed the observations in other embodiments related to color change, bubble formation, and minor pitting of electrode metal; outcomes that can be associated with the proposed electrogelation mechanism. To provide enhanced gelation, both electrodes were formed into spring-like coils, increasing the surface area of both the positive and negative electrodes. The experimental results are shown in FIG. 13. The electrogelation process was highly reactive, generating significant bubble formation at the negative electrode and overall gelation after 10 min of voltage application. A fairly distinct green-blue-indigo-violet color spectrum was generated, with green at the positive electrode and violet at the negative electrode.

Example 13

Parallel Electrode Gelation of Solubilized Silk with Salt and DMEM

For applications of electrogelation to tissue engineering, it is important to understand the ability to create viable constructs that can provide the proper structural integrity and cell environment. In one proposed scaffold geometry, solubilized silk is combined with salt and DMEM (Dulbecco's modified Eagle's medium) and solidified. After soaking in water, the dissolved salt leaves an ideal porous geometry. A series of tests were conducted to explore the possibility that electrogelation can be used in the solidification of such scaffold materials. As shown in FIG. 14, parallel electrode experiments were conducted with salt- and DMEM-containing 4% and 8% solubilized silk. The DMEM gives the initial material a strong magenta color. During voltage application, an extreme amount of gaseous bubbles formed on the negative electrodes, with very little evidence of gelation on the positive. A strong green-blue coloration occurred, and after a short period of voltage application, the culture dish became too hot to touch. In addition, significant pitting of the positive electrode was apparent.

Example 14

Syringe-Based Spring and Needle Electrode Gelation of Solubilized Silk with Salt and DMEM The high temperatures generated during the parallel electrode experiments with the solubilized silk, salt and DMEM might reflect lower electrical resistance of the solution. The subsequent increase in current flow may make the process much more reactive. To investigate the ability to control the temperatures, a syringe-based version of the prior experiment has been conducted. The solubilized silk with the additives was placed in a 3 ml syringe, with a spring-shaped positive electrode and inverted needle used as the negative. The experiment was conducted in a 5° C. refrigerator. The gelation process was very reactive, generating extreme amounts of gaseous bubbles within 90 sec, eventually almost completely evacuating the syringe of silk. No visible silk gelation occurred, although a color change to dark brown was witnessed.

Example 15

Electrogelation Experiments Using Graphite Electrodes

Electrogelation tests show that the metallic electrodes used play a key role in driving the reaction rate. Especially when using solutions with low electrical resistance, it can be important to select electrode materials that are more noble; that is, materials that have lower electrochemical potential. In this context, experiments were conducted using graphite electrodes made from mechanical pencil leads as both positive and negative electrodes. As shown in FIG. 15, graphite makes very good electrodes, leading to rapid gelation, with a very well-defined three-dimensional gelation front. After just 10 min of voltage application, nearly the entire solubilized silk volume was gelated. Despite this fast and complete gelation, the gaseous bubble formation on the negative electrode was not excessive.

Example 16

Low Voltage (4 VDC) Electrogelation Experiments Using Graphite Electrodes and Solubilized Silk with Salt and DMEM In the prior pencil lead experiment, the use of a more noble material appears to have stabilized the gelation process. Of course, graphite pencil leads are not made of pure carbon; nevertheless, there was a reduction in the gaseous bubble formation and the gelation front was well defined. Another experiment was conducted using this setup with solubilized silk containing salt and DMEM. To further keep the gelation process under control, a voltage of 4 VDC was applied. This approach still did not provide discernable gelation of the silk with additives, even after 8 min of voltage application. Fairly significant bubble formation occurred. In addition, a slight color change from the magenta to orange/brown was witnessed. The DMEM contains a marker that turns the color from magenta to yellow when the pH drops to about pH 6. This is likely the cause of the color change.

Example 17

High Voltage (25 VDC) Electrogelation Using Pencil Lead Electrodes and Solubilized Silk with Salt and DMEM Prior experiments demonstrated that graphite electrodes maintained at low voltage can aid in controlling electrogelation processes. An experiment was conducted to understand the response of a pencil lead-based setup under high applied voltage. An applied voltage of 25 VDC caused a completely uncontrolled reaction in solubilized silk containing salt and DMEM. Most of the silk was displaced from the container by gaseous bubbles forming at the negative electrode and the rapid reaction created enough heat that the container was too hot to touch. No visible gelation was witnessed, although a hard, greenish residue was left behind in the sample container. This residue appeared to be precipitated solids in crystal form. Regardless of the electrode material, whether copper or carbon-based lead, it appears that high salt-content silk can be too conductive to allow a controlled gelation response in the silk without adjusting voltage and electrode efficiency.

Example 18

Monitored Electrogelation Using Graphite Electrodes

Previous experiments demonstrated excellent electrogelation results when graphite electrodes were used on solubilized silk. To more carefully measure the response of the electrogelation, a controlled graphite electrode (mechanical pencil lead) experiment was conducted. Using 25 VDC and monitoring the current draw with an ammeter generated rapid gelation occurred over a span of 10 min, producing no color change, but a well-formed gelation front that resulted in almost complete gelation of the silk volume. The current data indicated that immediately when the voltage is applied, about 7 mA is drawn from the battery. This level drops nonlinearly until a steady-state current of 3 mA is drawn. This current draw trend likely parallels the growth trend of the silk gelation.

Example 19

Electrogelation of Silk-Coated Raw Chicken

An important application for electrogelation is its application or administration to tissues. For example, electrogelation applied to skin might be employed to promote burn healing. An experiment was conducted as a proof-of-concept to see if raw chicken could be used to generate a silk-based gelation layer. A narrow strip of raw chicken was soaked in solubilized silk, acting as the positive electrode. A bare wire was used as the negative electrode. Upon applying a voltage, bubbles formed at the negative electrode, confirming that electrogelation was taking place. A lack of visual contrast between the semi-transparent silk gel and light-colored chicken tissue obscured visual results.

Example 20

High Voltage Electrogelation of Solubilized Silk

To explore the effect of high voltage levels on electrogelation, a series of experiments were conducted using a high voltage power supply from Gamma High Voltage. An example embodiment is shown in FIG. 16. A syringe needle was suspended 1 inch above the silk solution surface. The needle was set to either 10 kV or 20 kV positive potential. A bare wire electrode, submerged in the silk solution, was grounded. With the needle at +10 kV, significant sparks occurred, generated by the buildup of electrons at the needle tip and periodic discharge to the solution. No gelation was evident within the silk, although small bubbles were generated with each discharge. The cycling of the electron charging and discharging was controlled by the current-controlled power supply. With such a supply, the current draw is limited to prevent damage to the supply as the power level nears a peak allowable level. When the needle potential was increased to the +20 kV level, a significantly different response was witnessed. Instead of sparking and discharging of electrons, the silk solution directly under the needle pushed away from the needle position. The silk solution may have developed a positive charge on the top surface that was repelled by the needle. At this voltage level, the repulsion force caused the liquid volume to be manipulated. A follow-up experiment replicated this response. As the initial charge was applied, significant sparking occurred, with high current being drawn from the DC power supply. With adjustment of sample height and voltage, a stable trough in the silk solution was created. With decreased space between the solution and needle, the trough was driven deep enough that the bottom of the culture dish was nearly exposed. An additional observation with ambient lighting turned off, showed that a distinct blue halo was produced at the needle tip during the experiments. Upon further literature review, this appears to be a fairly well-known corona effect. The mechanism of creating the trough is likely attributable to ion wind—basically pumping ions at a high rate, causing the surface depression.

Example 21

Device Design—Use of Mixing to Increase Processing Speed

The original goal of these experiments was to focus a design effort on making an actual device that could produce electrogelated silk fast enough for real-time (continuous) usage. It is known that older silk can electrogelate faster than young (it is also known that after a certain age, the rate of electrogelation decreases—indicating that there is some limit to the positive effect of age on electrogelation rate). One key effect of time on silk is that self-assembly occurs, providing an increase in beta-sheet content. It was speculated that the shearing action of silk mixing could generate a similar effect; increasing beta-sheet content, like in older silk. An experiment was conducted with used 6 ml of 8.4% solubilized silk (32 days old) with 25 VDC and a conventional graphite electrode setup (0.5 mm type 2B pencil lead). The chamber was created by cutting a 10 ml Falcon tube in half (height-wise). A mixing auger was created by bending an insulated 22-gauge wire in one plane. The auger was mounted to a low RPM servo motor (10-15 RPM), controlled by a Parallax USB Servo board and a PC running Parallax Servo Controller Interface software version 0.9 h Beta. As shown in FIG. 18, the auger was positioned between the positive and negative electrodes, which are approximately 12 mm apart.

Over approximately the first 2 min of electrogelation, a solid would form on the positive pencil lead, as seen in prior experiments. As the solid grew in size, however, there was a transition during which the solid was pulled off of the positive electrode and became trapped on the auger as it was spinning. Once this transition occurred, the positive pencil lead would continue to generate silk gel, although it was continuously pulled onto the auger. After completion of the experiment, when the auger was removed from the Falcon tube, all of the silk gel remained on the auger (FIG. 18C). Some distinct differences were observed with this silk gel: The color of the gel was strikingly clear, in contrast to the whitish color of prior gel. The gel was not as stiff as prior gels, but was very sticky, and a coherent solid, which could withstand some deformation. After depositing this gel on a surface at room temperature, it was observed to begin returning to a liquid form. Nearly complete reversal (80%-90%) to a liquid occurred after five days. After fifteen days, this percentage was observed to be about the same; no further transition back to a liquid appeared to have occurred. It was speculated that it is the presence of bubbles in the gel that are driving the reversal back to a liquid. It is important to note that as the auger was pulling the gel from the positive electrode, it also was pulling the bubbles from the negative electrode. The resulting rotating mass contained both gel and a lot of bubbles. The pH of the silk gel/bubble combination appeared nearly neutral: around pH 7.0-pH 7.4. For applications in which quick gelation of a very sticky silk is desired and in which reversal back to liquid form is an advantage, this configuration is very promising. For example, this mechanism may be ideal for party string.

Example 22

Use of Mixing to Increase Processing Speed (Higher RPM)

Another mixing experiment was conducted using the same experimental parameters as Example 21 (8.4% silk, 33 days old, 0.5 mm 2B pencil lead, 25 VDC), except that only 4 ml of silk was used and a higher auger rotation rate (~400 RPM) was used. After the test, it was observed that about 30% of the silk had been electrogelated and was adhering to the auger. The silk gel appeared to have increased stiffness than in the lower rotation rate experiment.

Example 23

Instron® Device-Based Extrusion Testing of Electrogelated Silk

The stiffness of electrogelated silk was quantified by a series of mechanical tests. For most of the physical devices that would use electrogelated silk, it is likely that the silk would be extruded (pushed) out of an orifice. Therefore, the force required for extrusion and the mechanical properties of the extruded silk were studied. Applying shearing forces to solubilized silk causes beta-sheet formation, which increased the mechanical response of the silk. A very simple preliminary setup was used: the 8.4% concentration solubilized silk was electrogelated using a "standard" pencil lead embodiment. The electrogelated silk (about 2 ml) was removed from the experimental tube and inserted into a 5 ml syringe. The test was conducted on an Instron 3366 10-kN load frame with a 1 kN capacity load cell. A uniaxial compression method in BlueHill 2.0 was executed, which would push the silk out of the vertically-oriented syringe at a constant rate of 1 mm/second. As seen in FIG. 19, the silk was extruded as a very stiff, coherent stream. The force response was recorded on separate graphs. The act of forcing the silk through the small needle provided a dramatic increase in the material stiffness. The resulting silk was also very sticky, as the exiting silk stream would tend to cluster into a ball and tend to stick to the needle.

This experiment was repeated after thirty days to quantify the effect of aging on the extrusion process. During the next extrusion test, the forces required to extrude the older silk out of the syringe needle were so great that the internal silk pressures resulting in syringe damage and not extrusion. Hence it appears that under some circumstances aging has an effect on the ability to generate a stiff silk using shearing (related to β-sheet content).

Example 24

Voltage Generation

Earlier experiments indicated that the silk solution acts like an electrochemical cell after electrogelation is begun. In other words, when the voltage was removed from the electrodes, a voltmeter would indicate a non-trivial level of DC voltage. To explore the ability of silk to act as an electrochemical cell, a series of experiments were conducted. The first baseline experiment involved submerging new mechanical pencil lead electrodes into a non-electrogelated batch of silk (4 ml of ~8.4% silk, thirty-four days old) and recording any voltage present across them. Surprisingly, without ever having introduced an external voltage to this silk, a voltmeter indicated than 0.2 VDC was being generated. The anticipated current draw was likely in the micro-ampere range. It is speculated that the voltage generation could be due to the experiment acting as an electrochemical cell. Basically, the mechanical pencil lead is known to contain many materials beyond graphite, including metals. An electrochemical cell is typically set up by introducing electrodes of different material composition to an electrolyte. It is possible that the silk is acting as an electrolyte and the pencil lead has enough non-graphite metal, that it was acting like a battery. It is unknown at this time what determines which electrode is the positive or negative lead.

Example 25

Electrode Material Influence on Electrogelation

The use of graphite (mechanical pencil lead) as an electrode material was effective in electrogelation. The originally shiny surface of the electrode became rough after use in electrogelation. Knowing that the rate of electrogelation slows after initiation, it was speculated that the electrogelation could be largely driven by surface properties of the lead and not the bulk properties. To understand the effects of electrode degradation, a series of experiments were conducted. For each of these tests, new mechanical pencil lead electrodes were first used to electrogelate ~8.4% silk (25 VDC for 10 min). After electrogelation, whatever solid had formed on the positive electrode was removed. As discussed above, the portion of each electrode that had been submerged in silk during electrogelation was left with a roughened surface. These used electrodes were then subsequently submerged back into the remaining solubilized silk, using the configurations shown below. Using a voltmeter attached to the electrodes, the voltage generated by the silk was measured. Whether the shiny half or roughened half was submerged during the voltage recording and which electrode was used as a positive/negative. One consistent result of the experiment is that when the positive electrodes taken from electrogelation was submerged for the voltage reading, a relatively large voltage was recorded (~0.6 VDC). When the negative electrode was submerged, results were less consistent (possibly due to a change in ion kinetics). It is known that one influence on ion kinetics is solution pH, which may be dramatically affected by voltage applied in electrogelation.

Depending upon the electrogelation embodiment, while electrogelation is occurring the silk surrounding the positive electrode may have a lower pH than the virgin silk. After removal of the electrodes for use in the voltage measurement, the electrodes themselves will likely have pH values that reflect this behavior. When reintroduced into silk for voltage measurement, the silk likely continues to act as an electrochemical cell. The cell kinetics will be modified, depending upon whether the electrode pH enhances or suppresses the process. By submerging the positive electrode, which has a lower pH, the kinetics increase, producing a higher voltage reading. When the negative is submerged, which has an elevated pH, the kinetics are suppressed.

Possible physics behind electrogelation and implications for interpreting results warrant further discussion. When two different materials are either brought into direct contact or are brought into electrical contact through submersion in an electrolyte, a galvanic couple is created. Metals can have very different susceptibility to corrosion. Some metals, like zinc, can be very readily corroded, while others, most notably stainless steels and platinum, are corrosion-resistant. This property of metals is dictated by it's reaction in a galvanic couple. Less corrosive metals are more noble; that is, in a list of the galvanic series, these metals have a higher electrode potential. When the galvanic couple is created, the less noble metal will lose electrons which go into solution as metal cations. If a voltmeter were used to measure the potential between electrodes, the electrode made of the less noble metal could be considered the positive electrode and therefore the voltmeter would read a positive voltage potential. Electrons released will flow through the electrolyte to the more noble metal. On the surface of the more noble metal, dissolved oxygen will be reduced to hydroxide anions through the gaining of the electrons. If the less noble metal were not present, the other metal would still undergo reduction of oxygen to hydroxide, except the electrons would be furnished by this metal through oxidation.

Some of the electrode materials that have been used throughout the entire set of electrogelation experiments include platinum, copper, aluminum, and graphite. Platinum is very noble, while copper and aluminum are not (very low within the galvanic series). Although the main constituent in mechanical pencil lead is graphite, which is the most noble metal, there are other elements that are present. Unfortunately, it is therefore likely that the actual nobility of the graphite mechanical pencil lead is dependent not just on the graphite content, but the other elements as well. It is unknown what the actual composition of the graphite electrode used in these experiments is, or what is its corresponding electrochemical potential.

If electrodes of the same pure metal are used, a galvanic couple should not be created. From this point of view, unless another source of electrons is provided, no voltage potential should be measured across the electrodes. In the use of the aluminum, copper, and graphite electrodes in these electrogelation experiments, there are likely alloying elements and other material constituents that would cause a galvanic couple to be created. If one measures the voltage potential across the electrodes, the measurement would be nonzero and the voltage would be either positive or negative depending upon which electrode was contacted with the positive voltmeter lead. There appears to be an additional electrochemical response generated in the electrogelation process beyond the creation of a galvanic couple. Furthermore, silk is an unusual electrolyte. It is known that silkworm silk contains a variety of metal ions, which may remain in the solubilized silk solution after processing. It appears that these ions may influence the electrochemical process of electrogelation and are likely detected during voltmeter readings across electrodes.

Example 26

Effects of Platinum Electrodes on Electrogelation

In light of the discussion above, a series of experiments were undertaken to confirm that if a very noble, pure metal were used as electrodes, that the electrogelation would either not occur or would be much slower than if mechanical pencil leads were used. Using the frequently used experimental setup of Example 20, two electrodes were partially submerged in ~8% solubilized silk fibroin (48-days-old). For these experiments, both mechanical pencil lead and 0.02" diameter, 99.95% pure platinum (Pt) electrodes were used. In addition, pH paper was used to record the pH of the silk solution before and after electrogelation. The 48-day-old silk solution was found to have a pH of pH 6.0-pH 6.3. In the first experiment, a Pt electrode was used as a positive electrode, with a mechanical pencil lead negative electrode. With 25 VDC applied, electrogelation occurred at a rate that was significantly lower than if two pencil lead electrodes were used. Based on a visual observation from the power supply used, 2 mA of current was drawn during the experiment. After 10 min of electrogelation and the applied voltage was stopped, a voltage potential of 0.95 VDC was measured across the electrodes. This implies that the silk after electrogelation is acting like a battery; i.e., a DC voltage source. The resulting electrogelated silk was nearly transparent. Once the solid gel was removed from the non-electrogelated silk solution, the remaining solution was shown to have a pH 7.2-pH 7.6. The pH of the solid gel surface (the pH paper could not be inserted into the interior of the solid) was found to be pH 4.9-pH 5.1. The expected outcome of this experiment was that no electrogelation would occur, given the high nobility of Pt which was used as the positive electrode. While the gelation rate was slower, it clearly was occurring. As discussed herein, it is possible that the ions dispersed in the silk solution may have contributed to the electrochemical process that did occur (although one would expect the supply of electrons to be dissipated fairly quickly). Further, despite the fact that Pt is very corrosion-resistant, every metal does corrode at some level. Therefore, this very low corrosion rate could be contributing toward electrogelation.

Because both the positive and negative electrodes play a role in the galvanic corrosion explanation for electrogelation, a follow-up experiment was conducted to see which electrode plays the dominant role. The prior experiment was simply adjusted by using the mechanical pencil lead as the positive electrode and the Pt as the negative. All other experimental conditions remained the same. Electrogelation occurred at a rate that matched the rates observed when two mechanical pencil leads were used as electrodes. It appeared that the positive electrode plays the dominant role in dictating electrogelation rate. The resulting electrogelated silk was opaque and white (similar to the outcome from graphite electrodes). The remaining silk solution was found to have pH 9.4-pH 9.7, while the electrogelated silk had pH 4.6-pH 4.9. The measured voltage potential after gelation of 1.83 VDC is about double the voltage level observed when Pt was the positive electrode and graphite was the negative electrode. This voltage increase might be due to the increased number of electrons that would be ejected from the graphite electrode because it is less noble than the Pt and is much more susceptible to corrosion.

When two Pt electrodes were used for electrogelation, it was observed that electrogelation occurred, albeit at a slow rate. The rate was approximately the same as when the positive electrode was Pt and the negative was graphite. Interestingly, the resulting solid gel was observed to be an opaque white, not clear like the resulting gel in the experiment using a positive Pt electrode. The voltage potential across the Pt electrodes after electrogelation was measured to be 1.98 VDC. This is not consistent with the speculation that this "battery" potential is related to the amount of electrons pumped into the silk solution through a corrosion process. It is unknown what mechanism is causing the voltage increase and why transparency of the silk gel is influenced by the electrode combination. The remaining silk solution was found to have a pH of pH 8.0-pH 8.5, while the electrogelated silk had a pH of pH 4.6-pH 4.9.

Example 27

Platinum Electrodes with Solubilized Silk and DMEM

Prior experiments showed that the introduction of DMEM solution containing salt had a dramatic effect on electrogelation. Because the use of a Pt positive electrode still resulted in electrogelation while dramatically reducing the amount of corrosion that occurred, it was thought that the addition of DMEM would have a positive effect on the gelation rate, without contributing significantly to greater corrosion. Furthermore, the pH of the ungelated silk solution and the resulting gel is effected by electrogelation. It was also observed that the pH of DMEM was greater than the pH of solubilized silk. This elevated pH was speculated to be able to increase gelation rate when mixed with the solubilized silk before electrogelation. Experiments were conducted to observe the influence of DMEM on electrogelation rate when two Pt electrodes are used.

The DMEM and solubilized silk used in these experiments was observed to have pHs of pH 8.2-pH 8.5 and pH 6.0-pH 6.3, respectively. When mixed with a DMEM concentration of 40%, the resulting solution had a pH of pH 7.9-pH 8.2. Using 25 VDC, the two Pt electrodes resulted in extremely fast gelation (~1 min to achieve 90%-95% gel). Along with the fast forming of a solid on the positive electrode, very significant bubble formation occurred on the negative Pt electrode. The initially light purple coloration of the DMEM was changed to a light yellow where the silk electrogelated. The DMEM has a pH marker included that transitions to yellow when a pH of about pH 6 is reached. The non-electrogelated silk was observed have a pH of pH 8.8-pH 9.7, while the gel was observed to have a pH of pH 3.1-pH 3.4. The presence of the DMEM had a effect on electrogelation. In this case, however, the use of Pt electrodes resulting in controlled gelation rates. Changes in pH accompany the dramatic gelation rate changes; pH of the liquid increases and of the solid decreases.

In another experiment, the same double Pt electrode setup with a DMEM and silk mixture was used, although a lower voltage of 5 VDC was applied. This experiment resulted in an electrogelation rate that was about the same rate observed with graphite electrodes with an applied voltage of 25 VDC and solubilized silk only. After electrogelation of 10 min, about 90%-95% gelation was achieved. The resulting liquid silk and gel had pHs of pH 9.5 to pH 10.0 and pH 3.1 to pH 3.4, respectively.

Example 28

Use of a Dialysis Cassette to Isolate the Electrodes and Electrogelation Products One of the concerns of the electrogelation process is that the pH levels of the solution and gel can achieve extreme values (from pH 3-pH 14). Another concern is that the process may involve electrolysis—the breaking down of the water content of the silk solution into hydrogen and oxygen gas, the hydrogen gas being problematic for cell survival. Therefore, an experiment was conducted using a dialysis cassette using a porous membrane to separate the products generated during electrogelation. A platinum electrode was inserted into the syringe port of a dialysis cassette filled with 8 wt % silk solution. This electrode was used initially as the positive electrode. A negative platinum electrode was immersed in de-ionized water containing common table salt. The application of 25 VDC to this electrogelation setup resulted in a good gelation response.

During this process, the hydrogen gas which typically forms on the negative electrode was kept outside of the dialysis cassette, away from the gel. After completion of the experiment, the pH of the un-gelated silk solution was shown to be between pH 7.9 and pH 8.2. This likely represents a slight pH rise over the pH of the virgin silk solution (for the 74-day-old silk solution used, the pH is likely about pH 6). The pH of the liquid on the surface of the gel was measured to be around pH 6-pH 7.2. This experiment provides a method for keeping hydrogen gas segregated from the silk solution and gel by employing an appropriate membrane material. It is also clear that the pH range measured around the gel is much closer to neutral than in arrangements in which the positive and negative electrodes were submerged in the solubilized silk fibroin solution.

Electrogelation was also performed using a dialysis cassette setup, but with the negative electrode inside the cassette, positive outside, and using a 30 VDC supply voltage. Initially, the results were ambiguous: no visible gelation had occurred and the only visible response was the formation of bubbles on the electrodes. When the positive electrode was brought into contact with the dialysis cassette membrane, however, gel formed on the inside of the membrane along the area of contact of the electrode. Based on this result, the dialysis cassette was removed from the de-ionized water bath. Using the positive electrode like a writing instrument, it was possible to form shapes and letters on the inside surface of the membrane from silk gel. This result is intriguing because the cassette did not have to be in a bath and produced a controlled gelated geometry. This process might be exploited in the future to make a 3D, rapid prototyping tool using silk gel material. Application areas include the creation of customized silk-based tissue engineering scaffolds.

Example 29

Reversed Electrogelation—Solidifying and Re-Liquifying Silk Gel

The silk gel microstructure generated in electrogelation may comprise primarily silk I structure (FTIR and CD measurements will confirm/refute this assertion). This metastable material phase is intriguing because it typically can be manipulated to go back to a random coil conformation (silk solution) or to form a β-sheet conformation (stiff gel and solid). Knowing that silk I can be re-liquified, an experiment was conducted to study this phenomenon as applied to electrogelation. Platinum electrodes were submerged in a 4 wt % silk solution. The electrodes were used to charge the solution with 25 VDC for 3 minutes. The outcome is shown in FIG. 21B. The electrical connections were then reversed; what was a positive electrode was changed to be a negative electrode and the former negative electrode was made positive. The experimental outcome is shown in FIG. 21C. The silk gel that had formed originally on the positive electrode became semi-transparent before entirely disappearing. A new gel formed on the electrode that was formerly the negative electrode, as shown. This experiment showed that the gelation process can be fully reversed. Electrogelation, therefore, shows promise as a process for applications in which a transition from liquid to solid is important. For example, it can be envisioned that electrogelation could be used to actuate a soft "leg" in a soft-bodied robot; cyclic solidification and re-liquification would cause locomotion.

Example 30 pH Induced Silk Fibroin Bioadhesives

The inventors have discovered that pH-induced silk fibroin gels display adhesive characteristics that can be utilized in bioadhesive applications. The investigation on pH induced silk gels can also help understanding the significance of increase proton concentration in the mechanism of electrogel (e-gel) formation. In a typical experiment, an aqueous silk solution can be titrated using a strong acid to control the solution pH. A dilute aqueous HCl solution was added into an 8 wt % silk solution (pH 6.4) at a 1:10 volumetric ratio to adjust the final proton concentration due to strong acid from 0.01 M (pH~4) to 0.1 M (pH~1.5). This process led to the formation of a sticky, soft-solid, gel-like material. This adhesive silk gels formed due to pH titration of the silk fibroin solution is termed herein as the "pH-gels".

Materials and Methods

Preparation of Aqueous Silk Fibroin Solutions.

Silk fibroin aqueous solutions were prepared as previously described (Sofia, 2001). Briefly, *Bombyx mori* cocoons were boiled for 20 min in an aqueous solution of 0.02 M sodium carbonate and then rinsed thoroughly with deionized water. After overnight drying, the silk fibroin was dissolved in an aqueous solution containing 9.3 molar LiBr at 60° C. The solution was dialyzed against deionized water using Slide-A-Lyzer® dialysis cassettes (MWCO 3,500, Pierce Chemicals, Rockford, Ill.) for 2 days to remove the residual salt. The final concentration of the silk fibroin was approximately 8 wt %.

Preparation of Silk Hydrogels.

pH-gels (i.e., silk hydrogelation triggered by dropping acid in silk fibroin solution to reduce pH) was prepared by adding a dilute aqueous HCl solution into a 8 wt % silk solution (pH 6.4) at a 1:10 volumetric ratio to adjust the final proton concentration due to strong acid from 0.01 M (pH~4) to 0.1 M (pH~1.5).

Dynamic Oscillatory Rheology.

Dynamic oscillatory time, frequency and strain sweeps were performed using an ARES strain-controlled rheometer (TA Instruments, New Castle, Del.). In a typical experiment, the silk solution was loaded onto the bottom plate gently to prevent shearing of the sample and the top plate was lowered to a measuring gap distance of 0.5 mm. The normal force applied on the solution during lowering of the top plate was less than 0.05 N. A low viscosity mineral oil was used to prevent sample evaporation from the sides of the plate. Dynamic oscillatory time sweep tests were collected at low strain amplitudes ($\gamma=1\%$) to prevent sample manipulation at an angular frequency of $\omega=10$ rad/s. Subsequently, frequency sweeps were collected over a wide frequency range ($\gamma=1\%$, $\omega=0.1$-100 rad/s). Strain sweep measurements were performed from $\gamma=0.01$-1000% ($\omega=10$ rad/s) to determine the linear viscoelastic regime.

Dynamic Mechanical Analysis.

In a typical experiment, ~0.1 mL of sample was gently loaded onto the 8 mm diameter stainless steel plates of a TA Instruments RSA3 Dynamic Mechanical Analyzer (DMA) directly. The top plate was lowered to a gap of 2 mm, applying less than 0.05 N compressive force on the sample. Sample equilibration was followed by a strain-controlled dynamic time sweep test at low strain amplitude (1-5% strain at 1 Hz). Subsequently, a transient tensile test at a constant transducer speed of 5 mm/min was collected until complete de-adhesion. The sample-plate interface was observed throughout the test for possible decrease in contact area. The work of adhesion was calculated from the integral of the normal stress-strain curve (Ponchel, 1987) using TA Instruments data analysis software.

Raman Spectroscopy.

A Jasco NRS-3000 Series Laser Raman Spectrophotometer (Jasco, Tokyo, Japan) was used to obtain Raman spectra, with a 785 nm laser at a power of 180 mW. A 20× objective was employed and spectra were collected in the range of 283-1970 $cm^{-1}$ with an exposure time of 20 sec and 10 consecutive accumulations. Spectra were then analyzed using Jasco Spectra Manager Software for the NRS-3000 Series Raman.

Polarized Optical Microscopy.

A Nikon Eclipse E600 Polarizing Optical Microscope (Nikon, Tokyo, Japan) connected to a CCD camera (Diagnostic Instruments, Minnesota, USA) was used to obtain images that were then analyzed using the Spot 4.09 Image Analysis Software (Diagnostic Instruments, Minn., USA). A 20× objective was used for all samples.

Results and Discussion

Figure 33:
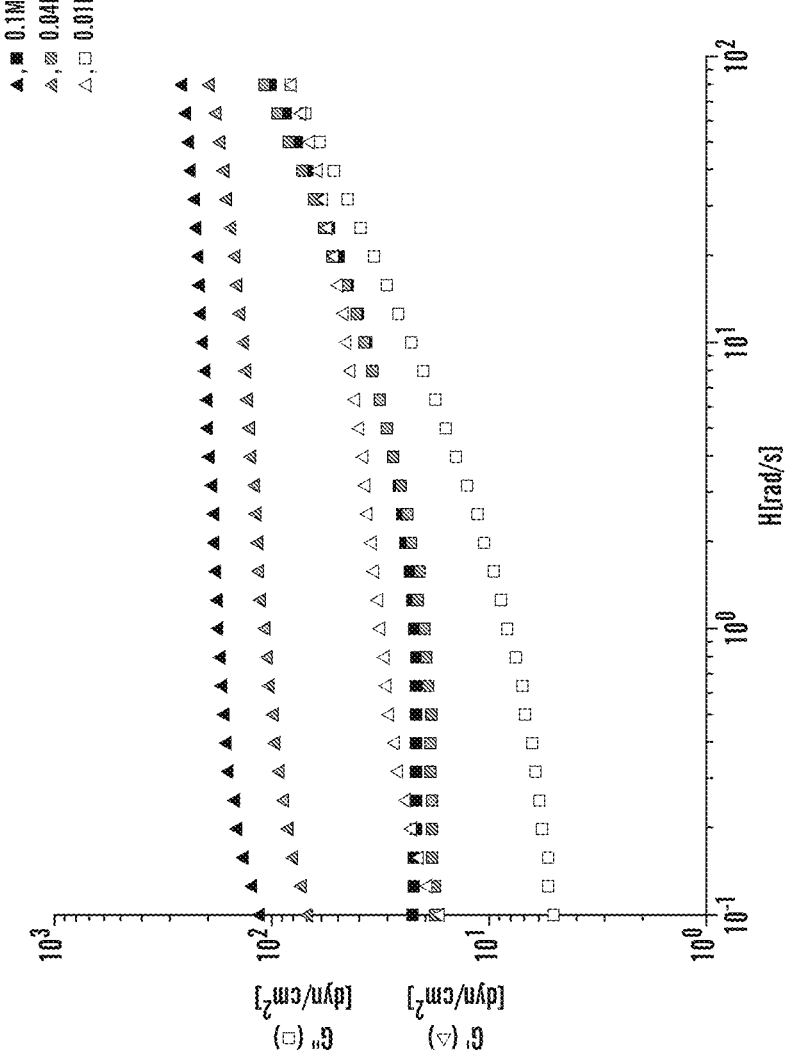
FIG. 33 is a graph depicting the results of dynamic oscillatory frequency sweeps collected from 8 wt % silk solutions titrated with 1 M HCl to a final proton concentration due to acid of 0.01 M, 0.04 M and 0.1 M.

The changes in solution viscoelastic properties due to the addition of acid were investigated using dynamic oscillatory rheology. After titration of the silk solution, pH-gels displayed viscoelastic behavior where the shear storage modulus, G', is greater than the shear loss modulus, G", for the measured frequencies, albeit a clear frequency dependence of G', indicating relatively long inter-chain crosslink relaxation times (FIG. 33). The hydrogel stiffness increased with increasing acid concentration or decreasing solution pH.

Figure 34:
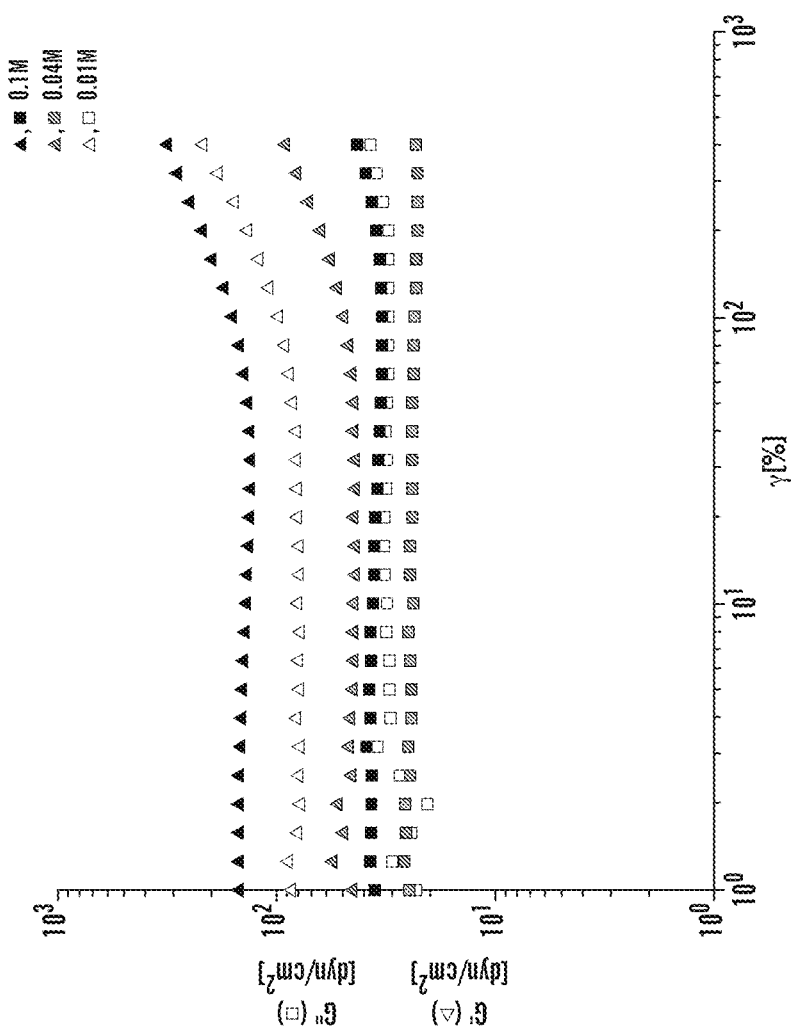
FIG. 34 is a graph depicting the results of dynamic oscillatory strain sweeps collected from 8 wt % silk solutions titrated with 1 M HCl to a final proton concentration due to acid of 0.01 M, 0.04 M and 0.1 M.

FIG. 34 compares the dynamic shear strain sweeps of G' collected from pH-gels. pH-gels showed a large linear viscoelastic regime and a subsequent non-linear regime similar to that observed for silk solutions, including a slight but reproducible strain-stiffening at high shear. Within the measurable strain amplitudes there were no apparent yielding for pH-gels regardless the final proton concentration. The strain hardening was reversible over several cycles.

FIG. 35 shows Raman spectra collected from silk solution and pH-gels ([$H^+$]=0.1 M). In the amide I region (FIG. 35A), peaks at around 1662 $cm^{-1}$ roughly correspond to a β-sheet and random coil conformation. Peaks around 1665 $cm^{-1}$ and 1660 $cm^{-1}$ have been associated with the stretching of the C=O bonds along the backbone chains in β-sheets (Rousseau, 2004) and random coils (Monti, 1998), respectively. The broad shoulders in the amide I region (1600-1700 $cm^{-1}$) for the silk solution resembled that of the pH-gel, suggesting a predominantly unordered conformation. In the amide III region (FIG. 35B), silk solution and pH-gels share a broad peak centered at about 1250 $cm^{-1}$, which along with the broad amide I peaks lends more evidence to an unordered secondary structure in these systems. On the other hand, the possible presence of silk I structures rich in helical interactions in pH-gels can not be ruled out, considering the similarity between the Raman spectral patterns of the random coil and silk I structure. Overall, the Raman data suggest that pH-gel formation is predominantly due to physical, entanglement crosslinks and possible helical interactions between silk fibroin chains that are not associated with significant β-sheet formation.

Figure 36:
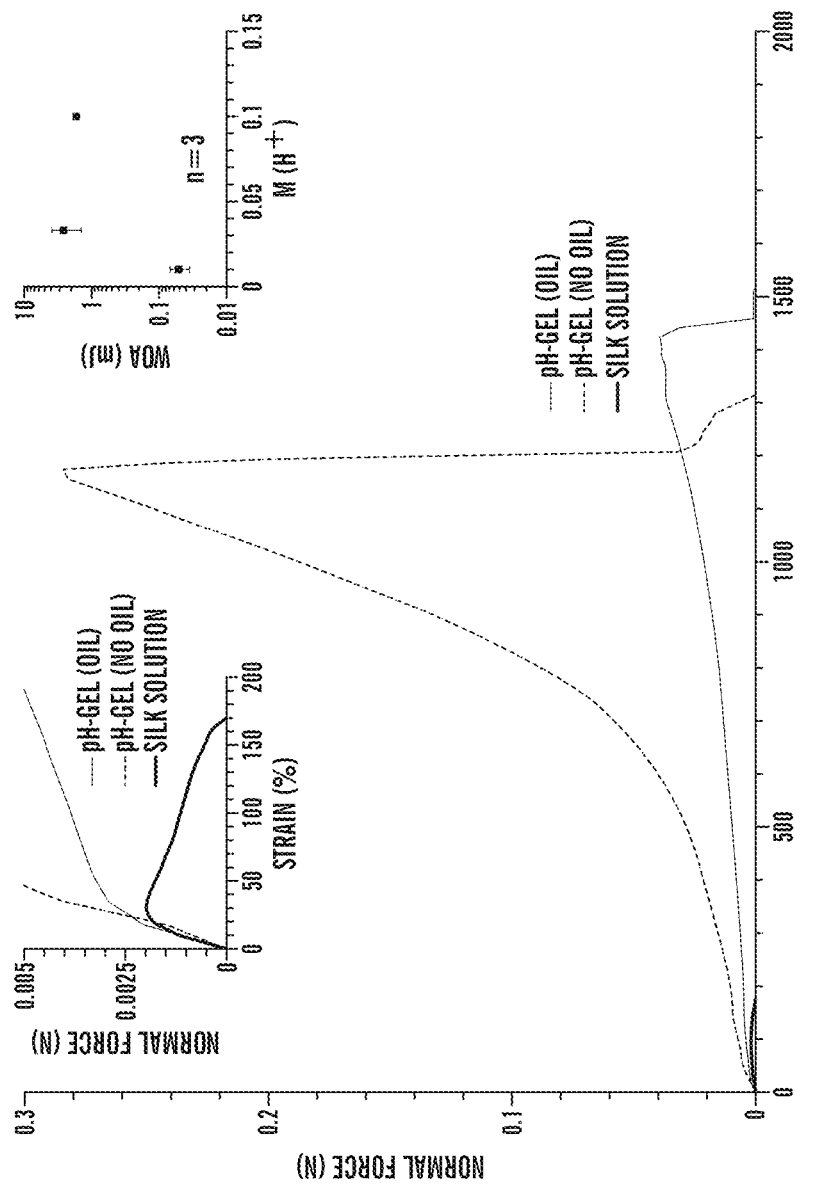
FIG. 36 is a graph depicting the results of adhesive characteristics of silk solutions and pH-gels measured by DMA transient testing. The graph shows engineering normal stress-strain curves for silk solution and pH-gels (with or without oil) on stainless steel surfaces. The inset panel on the left shows the low strain response, and the inset panel on the right shows the dependence of work of adhesion values for pH-gels on proton molarity.

FIG. 36 shows the adhesive characteristics of silk solution and pH-gels ([$H^+$]=0.03 M) on stainless steel surfaces measured by a dynamic mechanical analyzer operated in strain controlled, transient tensile testing mode. All samples displayed similar, linear stress-strain behavior at low strains (<20%) (FIG. 36, left inset). At higher strains, sample/plate contact area progressively decreased. For the silk solution, the decrease in the contact area led to a peak in the normal force which quickly diminished at ca. 150% strain. On the other hand, pH-gels showed unique, non-linear adhesion characteristics when compared to other synthetic bioadhesive systems (Mathiowitz, 1999). For pH-gels, after the initial linear regime, the normal force progressively increased. The non-linear regime was rather smooth, with an increasing slope despite the decreasing sample/plate interface. The increasing slope of the stress-strain curve that was observed in pH-gels was presumably due to stiffening due to surface effects and elongational forces. Application of a low viscosity oil around the pH-gel samples prior to adhesion testing in order to minimize possible surface effects led to a significant drop in the work of adhesion values, suggesting that surface effects may play a significant role in pH-gel adhesion. Both with and without oil application, very high strain-to-failure values (>1000%) were recorded. FIG. 36 right inset shows the dependence of work of adhesion values for pH-gels on proton concentration. Within the probed proton concentration range, [$H^+$]~0.03 mM was observed to have a stronger adhesive characteristics than other concentrations.

References
1. Leisk, G. G., et al., Electrogelation for Protein Adhesives. Advanced Materials, 2010, 22(6): 711-715.
2. Yucel, T. et al., Non-equilibrium Silk Fibroin Adhesives, Journal of Structural Biology, J Struct Biol. 2010, 170(2): 406-12.
3. Sofia, S., et al., Functionalized silk-based biomaterials for bone formation. Journal of Biomedical Materials Research, 2001, 54(1): 139-48.

4. Ponchel, G., et al., Bioadhesive Analysis of Controlled-Release Systems. 1. Fracture and Interpenetration Analysis in Poly(acrylic acid) Containing Systems. Journal of Controlled Release, 1987, 5: 129-41.
5. Rousseau, M. E., et al., Study of protein conformation and orientation in silkworm and spider silk fibers using Raman microspectroscopy. Biomacromolecules, 2004, 5(6): 2247-57.
6. Monti, P., et al., Raman spectroscopic studies of silk fibroin from *Bombyx mori*. Journal of Raman Spectroscopy, 1998, 29(4): 297-304.
7. Mathiowitz, E., et al., Bioadhesive Drug Delivery Systems, in Encyclopedia of Controlled Drug Delivery, E. Mathiowitz, Editor. 1999, Wiley: New York. p. 9-45.
8. Kinloch, A. J., The Science of Adhesion. 1. Surface and Interfacial Aspects. Journal of Materials Science, 1980, 15(9): 2141-66.
9. Peppas, N. A. and P. A. Buri, Surface, Inerfacial and Molecular Aspects of Polymer Bioadhesion on Soft Tissues. Journal of Controlled Release, 1985, 2: 257-75.

Example 31

Non-Equilibrium Silk Fibroin Adhesives

Electric field-responsive assembly of biopolymers has been utilized for biomaterials applications (Cheng et al., 2008; Leisk et al., 2009; Servoli et al., 2008). However, most research efforts have concentrated on "apparent equilibrium" state properties/applications of these systems. For example, Akkus et al. applied weak DC fields to synthesize dense and oriented collagen constructs and studied the biophysical characteristics of these scaffolds for tissue/ligament repair (Cheng et al., 2008). Servoli and coworkers employed small amplitude AC fields to enforce orientation of silk fibroin molecules for anisotropic film processing to induce directional spreading of MRCS fibroblasts (Servoli et al., 2008).

The inventors, however, discovered that the silk fibroin aqueous solutions transition into a "non-equilibrium", soft-solid-like material (electrogel or e-gel) via application of DC electric fields on the order of a few tens of V/mm (Leisk et al., 2009). This system displays unique, viscoelastic and adhesive properties suggesting prospects for biomedical applications.

Silk hydrogels have been studied for potential biotechnological applications due to their exceptional mechanical properties, biocompatibility, controllable degradation rates and self-assembly into 3-sheet rich networks (Kim et al., 2004; Altman et al., 2003; Horan et al., 2005; Ishida et al., 1990; Jin and Kaplan, 2003; Yucel et al., 2009). Self-assembly and subsequent hydrogelation of silk fibroin was triggered in vitro in solution conditions such high temperatures or high ionic strength (Kim et al., 2004) or alternatively in physiologically relevant solution conditions via ultra sonication (Wang et al., 2008) or vortexing (Yucel et al., 2009) for cell/drug encapsulation/delivery. In the majority of these silk hydrogel systems, the hydrated network is rich in non-covalent but essentially irreversible, intermolecular 3-sheet cross-links. In contrast, the e-gel system involves temperature reversible, dynamic self-assembly of silk (Leisk et al., 2009). This material displayed interesting viscoelastic properties, such as reversible shear stiffening at low shear amplitudes followed by irreversible stiffening at high shear amplitude. Increasing the electric field strength and/or the electrogelation duration, as well as application of elongational and/or shear forces resulted in transitioning of the e-gel into more stable hydrogels richer in 3-sheet content, with remarkable changes in viscoelastic and adhesive properties.

In this example, insight into the electrogelation process of silk has been provided. The changes in rheological behavior of the silk fibroin aqueous solution associated with the electrogelation process in situ via electric field rheology to minimize dehydration and shear/elongational force effects have been characterized; and the dependence of viscoelastic characteristics on various processing conditions has been identified. Additionally, the structure, micron-scale morphology and adhesion of e-gels are compared with other silk hydrogel systems to develop an electrogelation model, en route to understanding the origins of unique adhesive characteristics of the e-gel system.

Methods and Materials

Preparation of Aqueous Silk Fibroin Solutions.

Silk fibroin aqueous solutions were prepared as previously described (Sofia et al., 2001). Briefly, *Bombyx mori* cocoons were boiled for 20 min in an aqueous solution of 0.02 M sodium carbonate and then rinsed thoroughly with deionized water. After overnight drying, the silk fibroin was dissolved in an aqueous solution containing 9.3 M LiBr at 60° C. The solution was dialyzed against deionized water using Slide-A-Lyzer® dialysis cassettes (MWCO 3,500, Pierce Chemicals, Rockford, Ill.) for 2 days to remove the residual salt. The final concentration of the silk fibroin was approximately 7.3 wt. %.

Preparation of Silk Hydrogels.

pH-gels (i.e., silk hydrogelation triggered by dropping acid in silk fibroin solution to reduce pH was prepared by adding a dilute aqueous HCl solution into a 7.3 wt. % silk solution (pH 6.4) at a 1:10 volumetric ratio to adjust the final proton concentration due to strong acid from 0.01 M (pH 4) to 0.1 M (pH 1.5). Sonicated gels (s-gel) were prepared according to the previously described procedure (Wang et al., 2008); namely, 1 mL of 5 wt. % silk solution kept in a glass vial was sonicated for 5 s using a Branson Sonifier (Danbury, Conn.) at 10% power setting.

In Situ Electric Field Dynamic Oscillatory Rheology.

Dynamic oscillatory time, frequency and strain sweeps were performed using an ARES strain-controlled rheometer (TA Instruments, New Castle, Del.). Twenty-five millimeter diameter thin platinum disks were attached to the surface of custom-machined acrylic plates, which insulated the disks from the manufacturer supplied rheometer fixtures. The platinum disks were connected to conductive wires embedded in the acrylic insulation to enable in situ application of electric field during rheological testing.

In a typical experiment, the silk solution was loaded onto the bottom plate gently to prevent shearing of the sample and the top plate was lowered to a measuring gap distance of 0.5 mm. The normal force applied on the solution during lowering of the top plate was less than 0.05 N. A low viscosity mineral oil was used to prevent sample evaporation from the sides of the plate. The electric field was applied one minute after starting a dynamic oscillatory time sweep test (shear strain ($\gamma$)=1%, angular frequency ($\omega$)=10 rad/s). Frequency sweeps were collected over a wide frequency range ($\gamma$=1%, w=0.1-100 rad/s). Strain sweep measurements were performed from $\gamma$=0.01-1000% ($\omega$=10 rad/s) to determine the linear viscoelastic regime.

Dynamic Mechanical Analysis (DMA).

For DMA experiments, silk e-gels were prepared by immersion of two platinum electrodes in 0.5-1 mL of 7.3 wt. % aqueous silk solution and by application of 25 VDC over a 1-4 min period. The gel-like material that formed at the positive electrode (e-gel) was separated from the silk solution using tweezers. In a typical experiment, 0.1 mL of sample was gently loaded onto the 8 mm diameter stainless steel plates of a RSA3 dynamic mechanical analyzer (TA Instruments, Delaware, U.S.A.) directly. The top plate was lowered to a gap of 2 mm, applying less than 0.05 N compressive force on the sample. Sample equilibration was followed by a strain-controlled dynamic time sweep test at low strain amplitude (1-5% strain at 1 Hz). Subsequently, a transient tensile test at a constant transducer speed of 5 mm/min was collected until complete de-adhesion. The sample-plate interface was observed throughout the test for possible decrease in contact area. The work of adhesion was calculated from the integral of the normal stress-strain curve (Ponchel et al., 1987) using TA instruments data analysis software.

Raman Spectroscopy.

E-gel samples for Raman spectroscopy were prepared using the same procedure as in DMA sample preparation. A Jasco NRS-3000 Series Laser Raman Spectrophotometer (Jasco, Tokyo, Japan) was used to obtain Raman spectra, with a 785 nm laser at a power of 180 mW. A 20× objective was employed and spectra were collected in the range of 283-1970 cm$^{-1}$ with an exposure time of 20 s and 10 consecutive accumulations. Spectra were then analyzed using Jasco Spectra Manager Software for the NRS-3000 Series Raman.

Polarized Optical Microscopy (POM).

For POM experiments, a drop of 7.3 wt. % silk solution was applied between two platinum wires placed on a glass slide. After application of the silk solution, the wires were encapsulated between the glass slide and a cover slip and possible changes in morphology were observed during electric field application. A Nikon Eclipse E600 Polarizing Optical Microscope (Nikon, Tokyo, Japan) connected to a CCD camera (Diagnostic Instruments, Minn., USA) was used to obtain images that were then analyzed using the Spot 4.09 Image Analysis Software (Diagnostic Instruments, Minn., USA). A 20× objective was used for all samples.

Results and Discussion

Electrogelation Kinetics by In Situ Electric Field Rheology.

Figure 37A:
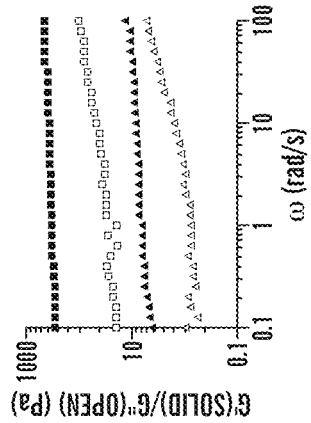
FIGS. 37A-37D show results of in situ rheological characterization of electrogelation kinetics.

FIG. 37A shows the time evolution of viscoelastic properties of the silk solution in response to a stepwise increase in the applied electric field from 0 to 20 V/mm at a rate of 1 V/mm/min. The initial, low elastic (G') and loss (G") modulus values corresponding to low applied electric fields were indicative of the initial solution state. At this stage, the viscoelastic properties of the silk fibroin solution were below the detection limit of the setup due to the small applied strain leading to high noise levels. An increase in both G' and G" was observed with increasing field strength, while the rate of increase was higher for G' than that of G", with an apparent G'/G" cross-over at an electric field of $E_x$~11 V/mm (the value of $E_x$ decreased with increasing rate of increase in the applied field). After the apparent G'/G" cross-over, there was a gradual increase in G' values, which approached a plateau of about 300 Pa. and a simultaneous decrease in the loss tangent for electric fields greater than $E_x$, typical of a gelling system. The final e-gel displayed a slight frequency dependence in the measured frequency range (FIG. 37B), indicating the formation of a hydrogel network via relatively long lifetime physical crosslinks between silk fibroin molecules.

Figure 37B:
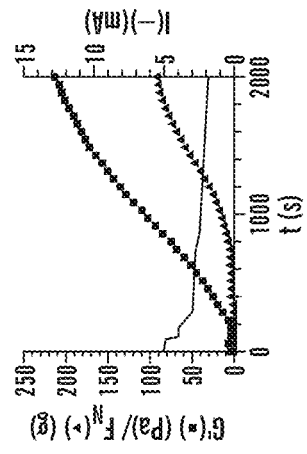
Figure 37C:
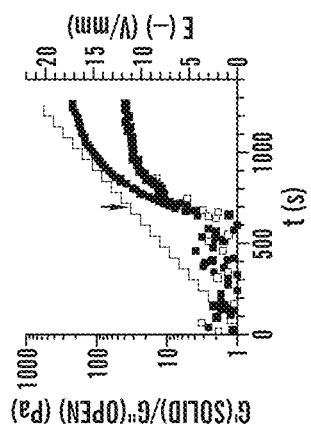

The kinetics of silk electrogelation at various applied electric fields was investigated to clarify the observed decrease in apparent $E_x$ with increasing rate of increase in the electric field. FIG. 37C shows dynamic oscillatory time sweeps collected from 7.3 wt. % silk solutions at different applied electric fields. For electric fields 65 V/mm, there were no apparent changes in viscoelastic properties during a 100 min test, while electrogelation was observed for fields of >7 V/mm, suggesting that a critical field of 5-7 V/mm was required to trigger electrogelation. The electrogelation kinetics increased with increasing field strength up to 15 V/mm. However, high electric field values lead to inconsistencies in the measured G' values (e.g., the drop in stiffness for the 15V/mm sample after ca. 500 s) after the initial stiffening, presumably due to increased bubble formation at the electrodes. The intrinsic bubble formation in e-gels can lead to an underestimation of the measured final hydrogel stiffness. On the other hand, a significant effect of bubble formation was expected on the measured apparent G'/G" cross-over time or $E_x$ values.

Figure 37D:
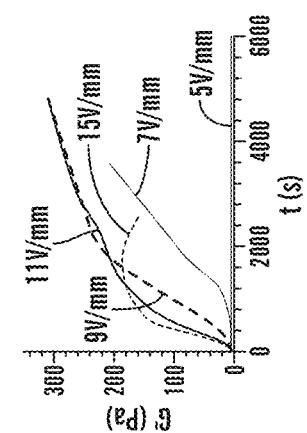

The increase in stiffness due to electrogelation was accompanied by a concomitant, substantial increase in the negative normal force (e-gel pulling the rheometer plates together) (FIG. 37D). Negative normal force generation was previously reported in semi-flexible biopolymer networks, such as crosslinked F-actin collagen, fibrin, neurofilaments and Matrigel, due to strain stiffening behavior in response to applied shear in these systems (Janmey et al., 2007). This normal force generation was attributed to the differences in the stress response of semi-flexible biopolymer chains for different modes of applied strain (greater stress response in tension than that in compression) leading to a net negative normal force. Even though a slight strain hardening was previously observed in e-gels, the amplitude of strain applied during the current dynamic time sweeps is lower than those corresponding to e-gel strain stiffening (Leisk et al., 2009). On the other hand, substantial negative normal force generation was also observed in electrorheological (ER) fluids (Jordan et al., 1992), particle suspensions that solidify at strong electric fields on the order of kilovolts per mm. For example, Jordan et al. observed a linear dependence of the negative normal force on the square of the electric field strength for an ER fluid, which could be attributed to the normal stress/field strength relationship in a capacitor (Jordan et al., 1992), a mechanism that is possibly more relevant to silk electrogelation. In addition to the negative normal force generation, electrogelation was also accompanied by a decrease in current reading, presumably due to the insulating effect of the e-gel and the increasing concentration of bubbles covering the electrode surface.

Figure 38:
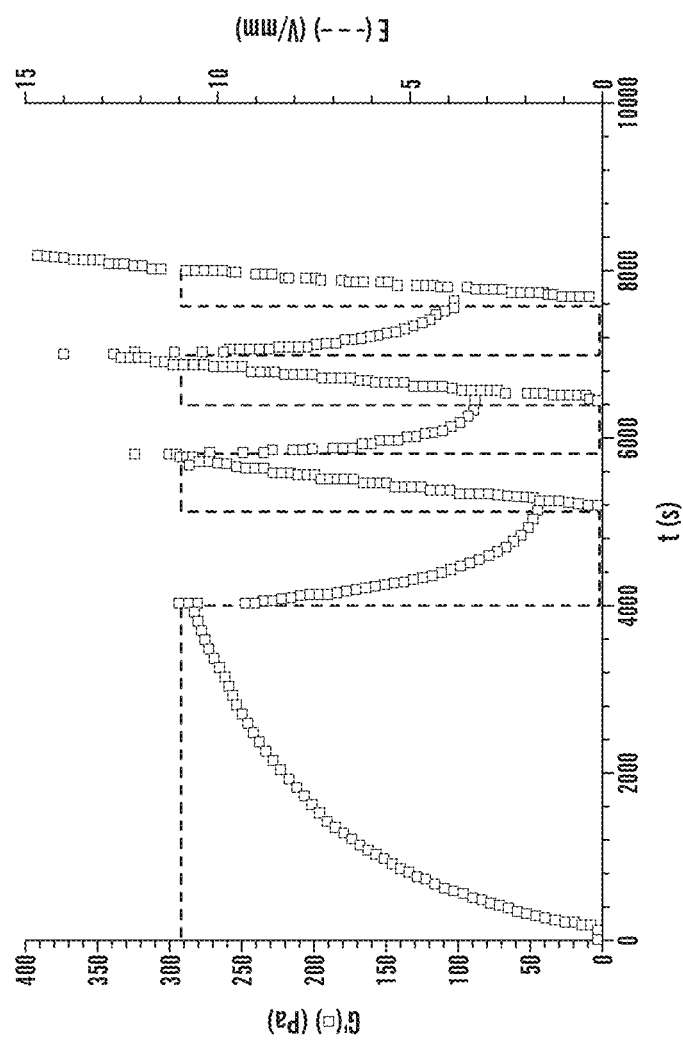
FIG. 38 is a graph showing the reversibility of electrogelation with application/removal of applied field.

FIG. 38 shows the effects of repetitive application and subsequent removal of the electric field on the rheological behavior of e-gels. Following the initial electrogelation, removal of the applied electric field led to a decrease in the measured storage modulus. E-gel stiffness dropped from ca. 300 to ca. 30 Pa in 10 min, suggesting partial reversibility of the electrogelation process. This apparent reversibility of hydrogel stiffness could be attributed to the dynamic nature of electric field induced physical crosslinks between silk fibroin molecules. Subsequent application of electric field led to rapid stiffening with faster kinetics than the initial electrogelation process. The decrease in the measured G' values immediately after the reapplication of electric field as compared to those measured immediately before the field application could be due to formation of bubbles or the build-up of negative normal force, both leading to underestimation of the measured final hydrogel stiffness, as discussed before. Increasing electrogelation kinetics during the second application of the electric field was probably due to the formation of physical crosslinks at a higher rate when compared with that during the initial electrogelation, perhaps because the initial electrogel network only partially disentangled due to removal of the applied field. When the electric field was removed the second time, a decrease in the stiffness similar to that due to the first field removal was observed. Overall, the stiffness of the e-gel could dynamically be controlled and partially reversed through repetitive application and removal of electric field.

Figure 39A:
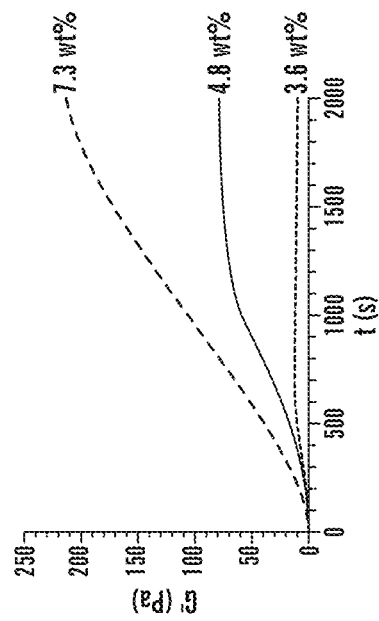

Electrogelation kinetics and the final e-gel stiffness were strongly dependent on various assembly conditions (FIG. 39) in addition to the applied field strength. For example, for an electric field of 9 V/mm, electrogelation kinetics slowed down significantly when the concentration was reduced from 7.3 to 4.8 wt. % with a significant drop in the final hydrogel stiffness (from >200 to ca. 80 Pa) (FIG. 39A). On the other hand, for a 3.6 wt. % solution, there were no apparent changes in the rheological behavior within 2000 s, suggesting a critical minimum silk concentration for e-gel formation at a given electric field strength.

Similarly, solution pH had a drastic effect on electrogelation kinetics. pH effects were only investigated at basic solution conditions, since slightly acidic (pH≤5) 4.8 wt. % silk solutions gelled immediately. For a field strength of 9 V/mm, increasing the solution pH from 6.5 to 8.3 led to a fourfold decrease in the measured G' values, while no electrogelation was observed when solution pH was initially adjusted to pH 9.3. Slowing down the electrogelation kinetics with increasing pH highlights the importance of increased proton concentration at the positive electrode due to the applied field on e-gel formation.

Structural Characterization by Raman and POM.

Figure 40:
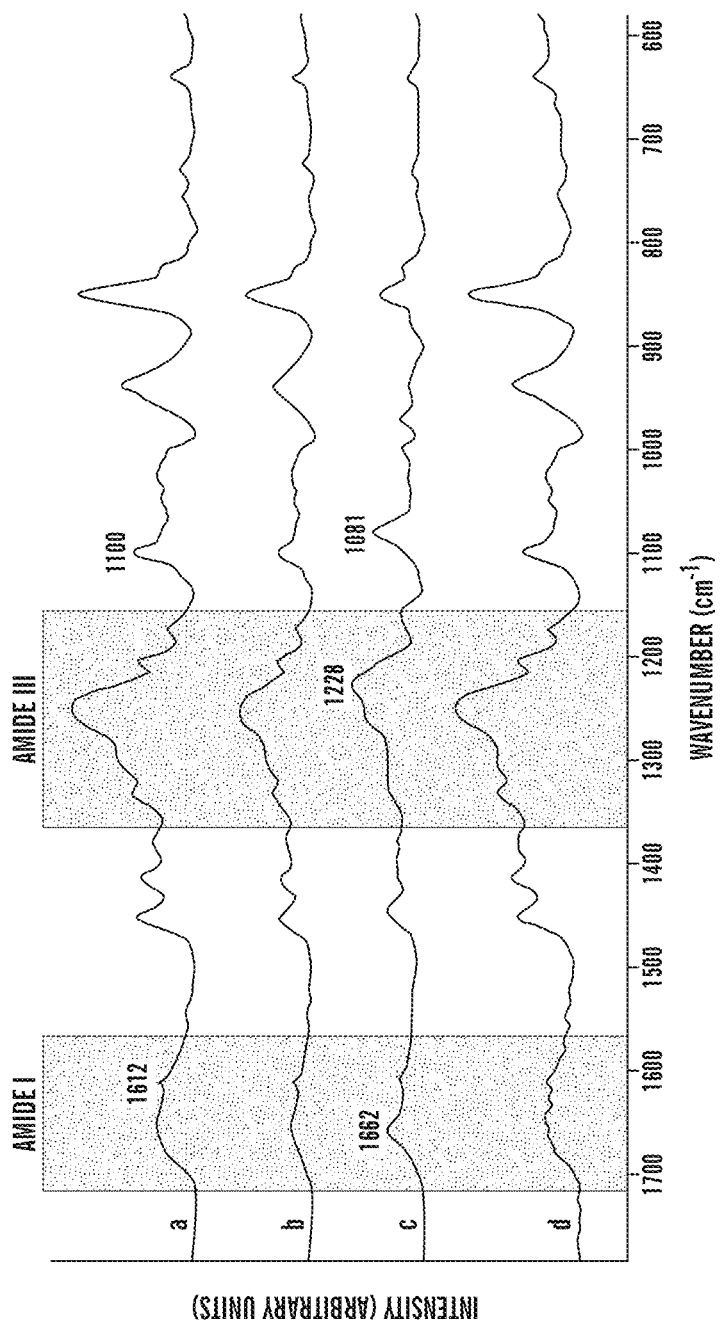
FIG. 40 is a graph showing the results of Raman spectra collected from e-gel (a), pH-gel (b), s-gel (c), and silk fibroin solution (d).

FIG. 40 shows Raman spectra collected from silk solution, pH-gels ([H$^+$]=0.1 M), e-gels and sonicated gels (s-gels). Raman data indicate clear differences between the s-gel and the other three cases (solution, e-gels and pH-gels). In the amide I region, s-gel showed a peak at around 1662 cm$^{-1}$ that roughly corresponds to a β-sheet and random-coil conformation, as prior studies have associated the peaks around 1665 cm$^{-1}$ and 1660 cm$^{-1}$ with the stretching of the C=O bonds along the backbone chains in β-sheets (Rousseau et al., 2004; Sirichaisit et al., 2003) and random coils (Monti et al., 1998), respectively. The broad shoulders in the amide I region (1600 cm$^{-1}$-1700 cm$^{-1}$) for the silk solution resembled that of the e-gel and the pH-gel, suggesting a predominantly unordered conformation (Rousseau et al., 2004). In the amide III region the peak for the s-gel at 1228 cm$^{-1}$ can be assigned to stretching of C—N bonds consistent with a β-sheet conformation (Sirichaisit et al., 2003; Qiu et al., 2009). Again, in the amide III region, silk solution, e-gels and pH-gels share a broader peak centered at about 1250 cm$^{-1}$, which along with the broad amide I peaks lends more evidence to an unordered secondary structure in these systems (Rousseau et al., 2004). The Raman spectrum of s-gel also differed from those collected from other three systems in presenting a peak at 1081 cm$^{-1}$, consistent with β-sheet conformation (Rousseau et al., 2004; Monti et al., 1998; Qiu et al., 2009), whereas the peak around 1100 cm$^{-1}$ for the other three systems is more indicative of the presence of random coils and turns (Rousseau et al., 2004). Overall, the Raman data suggest that the s-gel is richer in β-sheet content when compared with the other three systems. This high β-sheet content could be attributed to intramolecular folding of silk molecules into β-strands followed by intermolecular assembly into β-sheet rich hydrogel networks due to sonication, in good agreement with previous results (Wang et al., 2008). On the other hand, the overall molecular conformation of e-gels and pH-gels seem to be very similar to that of the solution state. Furthermore, the possible presence of silk I structures rich in helical interactions in both e-gels and pH-gels can not be ruled out, considering the similarity between the Raman spectral patterns of the random-coil and silk I structure (Monti et al., 1998). The lack of the previously reported, low helical spectral signature in e-gels (Leisk et al., 2009) could also be due to partial disruption of helical interactions and/or partial reversal of hydrogelation due to Raman sample preparation. In sum, the Raman data suggest that e-gel and pH-gel formation is predominantly due to physical, entanglement crosslinks and possible helical interactions between silk fibroin chains that are not associated with significant β-sheet formation.

It was reported that orientation of silk fibroin molecules in air dried films parallel or antiparallel to an applied AC electric field due to the net dipole moment of the silk fibroin protein, resulting from the surface charge, polar groups and mobile ions (Servoli et al., 2008; Motta et al., 2002). Hence, possible similar micron- to macro-scale alignment of previously reported micron-scale spherical and elongated silk fibroin micelles (Leisk et al., 2009) may be present in DC fields. Polarizing Optical Microscopy (POM) (Martin et al., 2000; Sohn et al., 2004; Xu et al., 2005) was used to characterize the possible alignment and birefringence of aforementioned pattern was expected. POM images were collected from the silk solution, e-gel and pH-gel [H$^+$=0.1 M] both under normal light transmission and at maximal birefringence (cross-polarizers at 90°). In both cases, no structural features were observed from silk solutions, while a similar micron-scale structural heterogeneity that resembles previously observed spherical and elongated, micellar microstructures, was observed for the e-gel (Leisk et al., 2009) and pH-gel. Neither e-gels nor pH-gels displayed birefringence patterns, which would have been expected to appear as bright color patterns with the polarizers at 90° (Martin et al., 2000; Sohn et al., 2004; Xu et al., 2005), suggesting the absence of long-range alignment of silk fibroin micelles in DC fields.

Adhesive Characteristics.

Figure 41:
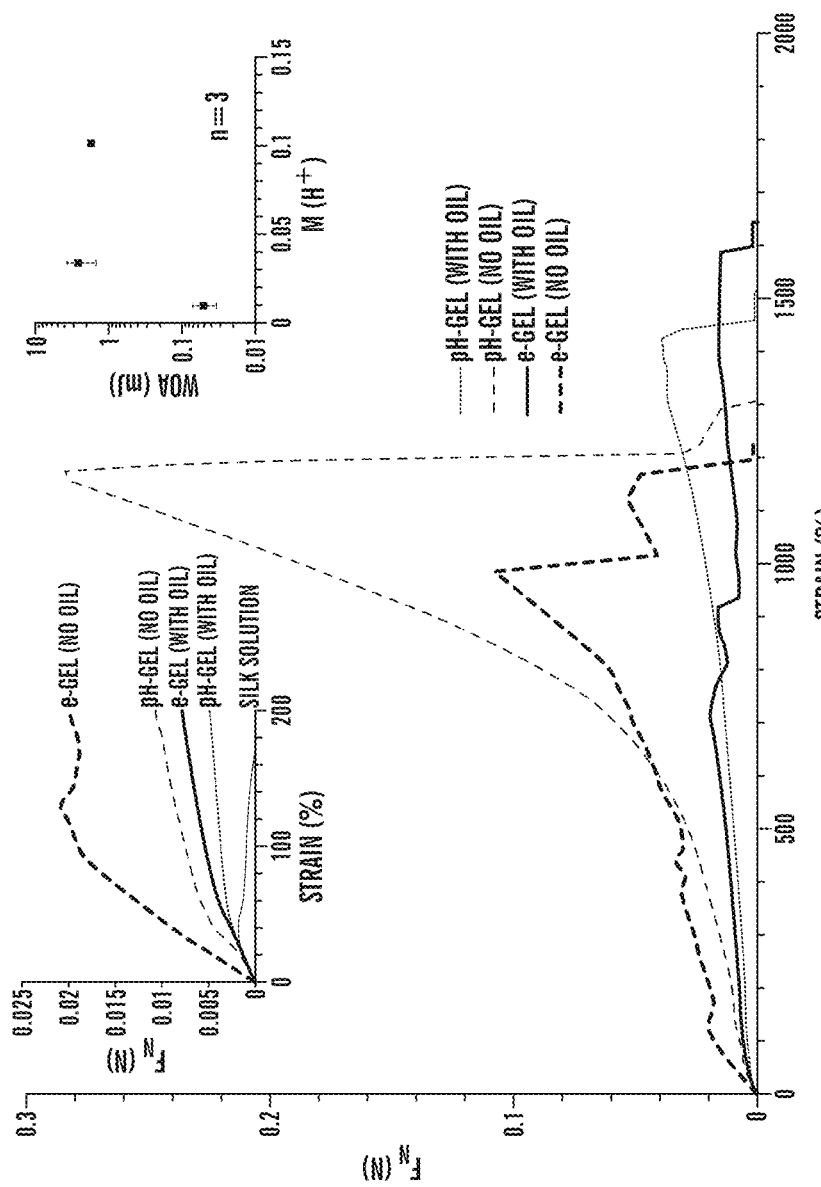
FIG. 41 is a graph showing the adhesive characteristics of silk hydrogels measured by DMA transient testing. The graph depicts the engineering normal stress-strain curves for silk solution (+), e-gels (◇, no oil; ○, with oil) and pH-gels (□, no oil; Δ, with oil) on stainless steel surfaces. The inset graph on the left shows the low strain response, and the inset graph on the right shows the dependence of work of adhesion values for pH-gels on proton molarity.

FIG. 41 shows the adhesive characteristics of silk solution, pH-gels ([H$^+$]=33 mM) and e-gels on stainless steel surfaces measured by a dynamic mechanical analyzer operated in strain controlled, transient tensile testing mode. All samples displayed similar, linear stress-strain behavior at low strains (<20%) (FIG. 41 left inset). At higher strains, sample/plate contact area progressively decreased. For the silk solution, the decrease in the contact area led to a peak in the normal force which quickly diminished at ca. 150% strain. On the other hand, both e-gels and pH-gels showed unique, non-linear adhesive characteristics when compared with other synthetic bioadhesive systems (Mathiowitz et al., 1999). After the initial linear regime, the normal force progressively increased for both systems. For pH-gels, the non-linear regime was rather smooth, with an increasing slope despite the decreasing sample/plate interface. A similar increase in the slope of the stress strain curve was also observed for e-gels, albeit random fluctuations in stress that are attributable to trapped gas bubbles in the e-gel acting as crack nucleation sites, which may lead to premature failure of e-gels. The increased slope of the stress-strain curve observed in both pH-gels and e-gels was perhaps due to stiffening of both systems due to surface effects and elongational forces. Application of a low viscosity oil around the samples prior to adhesion testing to minimize possible surface effects led to a significant drop in the work of adhesion values, suggesting that surface effects play a significant role in e-gel adhesion. In all samples, high strain-to-failure values (>1000%) were recorded.

The measured adhesion values of e-gels described in this example can be taken as a lower limit of the real intrinsic adhesive characteristics of the e-gel due to entrapped bubbles. The above adhesion testing results indicate that the essential adhesive properties of the e-gel can be captured by pH adjustment of the silk solution (e.g., the right inset of FIG. 41 shows the dependence of work of adhesion values for pH-gels on proton concentration). Interestingly, pH-gels that displayed a strong adhesive characteristics (e.g., [$H^+$] =33 mM, shown in the right inset of FIG. 41) were more compliant than e-gels in dynamic shear (FIG. 37B).

Electrogelation Mechanism.

Figure 42:
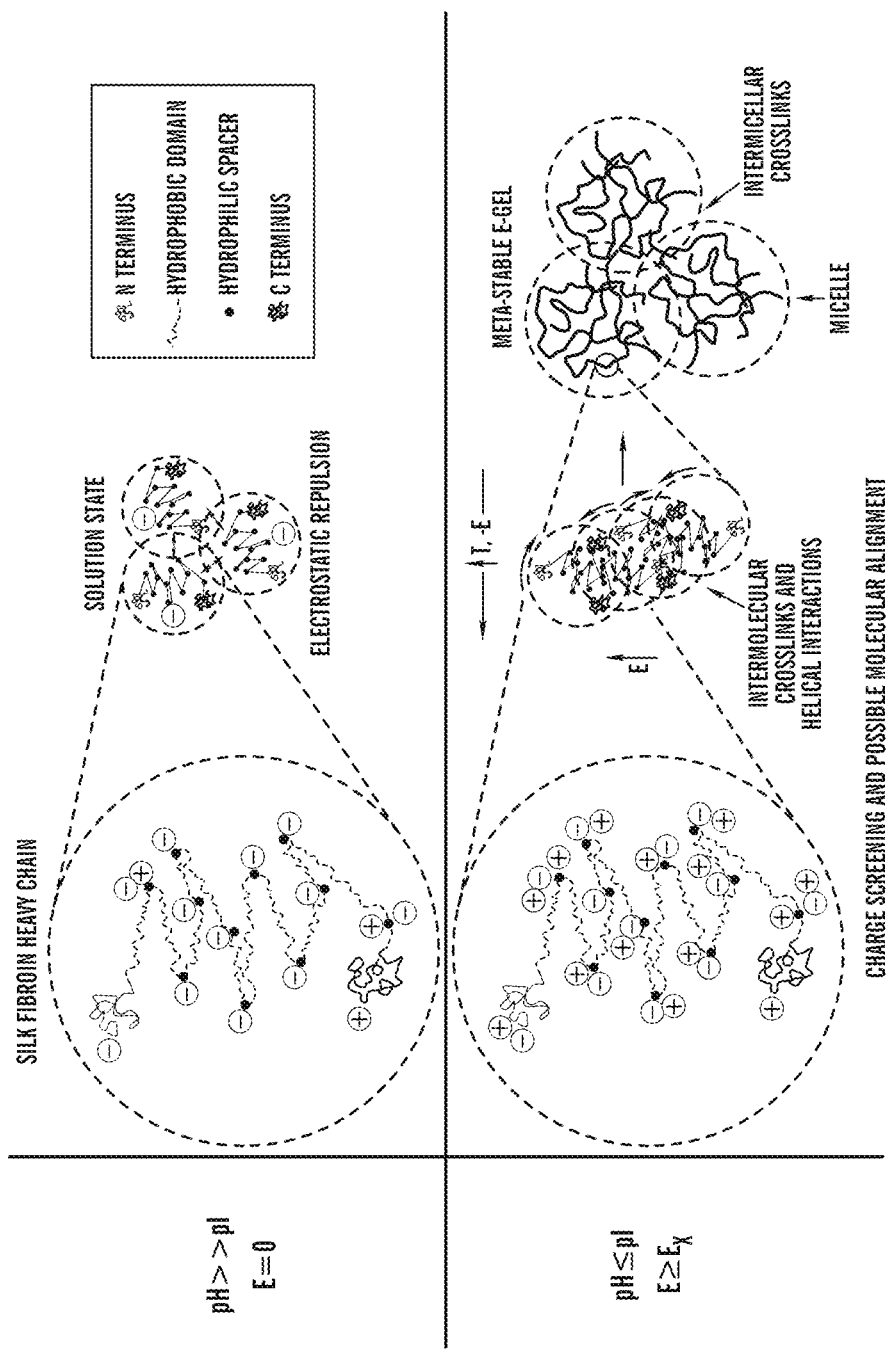
FIG. 42 is a schematic depicting the putative electrogelation mechanism.

FIG. 42 shows a schematic of the proposed electrogelation mechanism based on combined structural and mechanical data that is summarized in Table 1.

TABLE 1

Comparison of the structure and mechanical properties of e-gels with those of other silk hydrogel systems.

|  | Raman peak positions ($cm^{-1}$) | | | Rheology | | Adhesion |
|---|---|---|---|---|---|---|
|  | Amide I | Amide III | Other | G' (Pa) ($\omega$ = 1 rad/s) | Strain stiffening | WOA (mJ) |
| e-gel | 1600-1700 (broad, random) | ~1250 (broad, random) | ~1100 (random, turns) | ~300 | Leisk et al. (2009) | ~1 |
| pH-gel | 1600-1700 (broad, random) | ~1250 (broad, random) | ~1100 (random, turns) | 5-20 | Leisk et al. (2009) | 0.05-4 |
| s-gel | 1662 ($\beta$, random) | 1228 ($\beta$) | 1081 ($\beta$) | ~100,000 | N | ~0 |

In neutral to basic aqueous solution, the acidic charged groups in the amorphous domains of the silk fibroin heavy chain prevent intramolecular β-sheet folding, while the overall negative surface charge due to these charged domains prevent intermolecular self-assembly. The dependence of electrogelation kinetics on solution pH measured by rheology and similarities between the structure and adhesive characteristics of the e-gel and pH-gels according to combined Raman, POM and DMA data suggest that the increase in proton concentration in the vicinity of the positive electrode due to the applied electric field is possibly a predominant factor in electrogelation. This local decrease in solution pH presumably leads to screening of the acidic surface charged groups enabling intermolecular self-assembly events.

Dynamic shear rheology data indicated that e-gels were generally stiffer than pH-gels (FIG. 37B), albeit with similar adhesive characteristics. Higher stiffness of e-gels may stem from possible molecular alignment/chain stretching of fibroin dipoles facilitating a higher concentration of intermolecular crosslinks. However, such potential electric field induced structural changes may not be detectable using the current experimental techniques. Previous SEM (Leisk et al., 2009) and the above POM data suggest initial intermolecular assembly of silk fibroin molecules into micronsized micelles. Moreover, the overall e-gel concentration was very close to that of the silk solution (Leisk et al., 2009). The large size of micron-scale micelles as compared to that of the single fibroin molecule suggests self-assembly of amphiphilic fibroin molecules into complex micelles, in which hydrophobic interactions between repetitive domains of the fibroin could be screened by less hydrophobic, amorphous spacers that are more readily exposed to water. These micelles could be comprised of a low-density, fractal-like substructure leading to the relatively low overall concentration of the e-gel (FIG. 42). The lack of a significant increase in the β-sheet content in e-gels when compared to the solution state measured by Raman spectroscopy suggests that both the intermolecular self-assembly events leading to micelle formation and the crosslinks between these micelles leading to the observed soft-solid-like rheological behavior are mainly dominated by physical entanglements between random-coil-rich silk fibroin molecules and/or possible temperature reversible, helical interactions between the amorphous spacers in the silk fibroin chain. Rheology data indicate that these entanglements act as long lifetime crosslinks, perhaps due to increased hydrophobic interactions between tangled fibroin chains. Molecular weight dependence of silk electrogelation kinetics may not be easily estimated because increased molecular weight could increase the intermolecular entanglement crosslink density, while decreasing molecular alignment propensity with the applied field. Other factors, such as overall charge/charge distribution and solution temperature can also affect the electrogelation kinetics. For example, the removal of the negatively charged light chain may potentially decrease the critical field for electrogelation and/or speed up electrogelation kinetics at a given field strength through a shift in the pI.

Possible Origins of Adhesion.

Several theories have been proposed to describe adhesion of two dissimilar surfaces (e.g. electronic, adsorption, wetting, diffusion (interpenetration) and fracture theories (Kinloch, 1980)). For example, it is believed that formation of an intimate molecular contact at the interface between two adhering surfaces is perhaps necessary for adhesion (Kinloch, 1980).

The adhesive characteristics of e-gels and pH-gels on smooth stainless steel surfaces were different than that of the s-gel. Contrary to the strong adhesion of e-gels and pH-gels, s-gels did not show any detectable adhesion. The amorphous-rich structure and the hydrophilic nature of the e-gels and the pH-gels (as compared to the hydrophobic, β-sheet rich s-gels) and their viscoelastic properties can aid in the initial wetting and formation of a good interfacial contact between the gel and the stainless steel surface. Once intimate contact is achieved, strong adhesion can be formed mainly due to adsorption, i.e., adhesion due to surface forces acting between the gels and stainless steel surface oxide layer. For both the e-gel and the pH-gel, these surface forces can include hydrogen bonding due to the amide groups of the protein, and van der Waals interactions due to main chain and side chain polar groups, mobile ions and to a lesser extent the residual surface charge.

Some adhesion theories have also been applied to bioadhesion, the attachment of synthetic and biological macromolecules and hydrocolloids on biological tissue (Peppas and Buri, 1985). For example, mucoadhesion, which implies adhesion to a mucosal surface, is generally accepted to involve (1) the formation of an intimate contact between the adhesive material and the mucus through wetting and swelling of the material (not necessary for a fully hydrated hydrogel), (2) interpenetration of the adhesive and mucin chains and formation of entanglements and (3) possible formation of weak chemical bonds. Hydrogel characteristics such as high hydrogen bond formation propensity, high concentration of negative charge, high polymer molecular weight to increase entanglements with the mucin chains, high polymer chain flexibility to enable penetration into the mucus network and adequate surface free energy to enable proper wetting of the mucosal surface have been shown to increase mucoadhesion (Mathiowitz et al., 1999), while additional requirements include biocompatibility, non-toxicity and other factors.

Silk e-gels and pH-gels satisfy the above discussed criteria and hence are suitable to be used as mucoadhesives. Further, silk e-gels and pH-gels may be used in applications such as biomimetic dynamic adhesion (Peattie, 2009) through engineering of reusability into their inherently reversible and substrate tolerant nature (Leisk et al., 2009).

Studies aimed at addressing the main processing parameters controlling silk fibroin electrogelation were conducted. The structure and adhesive characteristics of e-gels and pH-gels were similar, highlighting the contribution of pH effects in e-gel formation. On the other hand, differences in shear rheological response between the e-gel and pH-gel suggested that additional factors, such as solution temperature and molecular weight, may also play a role in silk electrogelation kinetics.

References:

Cheng, X. G. et al., 2008. An electrochemical fabrication process for the assembly of anisotropically oriented collagen bundles. Biomaterials 29 (22), 3278-3288.

Leisk, G. G. et al., 2009. Electrogelation for protein adhesives. Advanced Materials 21, in press.

Servoli, E. et al., 2008. Folding and assembly of fibroin driven by an AC electric field: effects on film properties. Macromolecular Bioscience 8 (9), 827-835.

Inoue, S. et al., 2000. Silk fibroin of *Bombyx mori* is secreted, assembling a high molecular mass elementary unit consisting of H-chain, L-chain, and P25, with a 6:6:1 molar ratio. Journal of Biological Chemistry 275 (51), 40517-40528.

Zhou, C. Z. et al., 2000. Fine organization of *Bombyx mori* fibroin heavy chain gene. Nucleic Acids Research 28 (12), 2413-2419.

Jin, H. J. et al., 2002. Electrospinning *Bombyx mori* silk with poly(ethylene oxide). Biomacromolecules 3 (6), 1233-1239.

Jin, H. J. et al., 2004. Biomaterial films of *Bombyx mori* silk fibroin with poly(ethylene oxide). Biomacromolecules 5 (3), 711-717.

Kim, U. J. et al., 2004. Structure and properties of silk hydrogels. Biomacromolecules 5 (3), 786-792.

Nazarov, R., Jin, H. J., Kaplan, D. L., 2004. Porous 3-D scaffolds from regenerated silk fibroin. Biomacromolecules 5 (3), 718-726.

Vepari, C., Kaplan, D. L., 2007. Silk as a biomaterial. Progress in Polymer Science 32 (8-9), 991-1007.

Wang, X. Q. et al., 2008. Sonication-induced gelation of silk fibroin for cell encapsulation. Biomaterials 29 (8), 1054-1064.

Wang, X. Q. et al., 2007. Silk microspheres for encapsulation and controlled release. Journal of Controlled Release 117 (3), 360-370.

Altman, G. H. et al., 2003. Silk-based biomaterials. Biomaterials 24 (3), 401-416.

Horan, R. L. et al., 2005. In vitro degradation of silk fibroin. Biomaterials 26 (17), 3385-3393.

Ishida, M. et al., 1990. Solvent-induced and mechanical-treatment-induced conformational transition of silk fibroins studied by high-resolution solidstate C-13 NMR spectroscopy. Macromolecules 23 (1), 88-94.

Jin, H. J., Kaplan, D. L., 2003. Mechanism of silk processing in insects and spiders. Nature 424 (6952), 1057-1061.

Yucel, T., Cebe, P., Kaplan, D. L., 2009. Vortex-induced injectable silk fibroin hydrogels. Biophysical Journal 97 (7), 2044-2050.

Sofia, S. et al., 2001. Functionalized silk-based biomaterials for bone formation. Journal of Biomedical Materials Research 54 (1), 139-148.

Ponchel, G. et al., 1987. Bioadhesive analysis of controlled-release systems. 1. Fracture and interpenetration analysis in poly(acrylic acid) containing systems. Journal of Controlled Release 5, 129-141.

Janmey, P. A. et al., 2007. Negative normal stress in semiflexible biopolymer gels. Nature Materials 6 (1), 48-51.

Jordan, T. C., Shaw, M. T., McLeish, T. C. B., 1992. Viscoelastic response of electrorheological fluids. 2. Field strength and strain dependence. Journal of Rheology 36 (3), 441-463.

Rousseau, M. E. et al., 2004. Study of protein conformation and orientation in silkworm and spider silk fibers using Raman microspectroscopy. Biomacromolecules 5 (6), 2247-2257.

Sirichaisit, J. et al., 2003. Analysis of structure/property relationships in silkworm (*Bombyx mori*) and spider dragline (*Nephila edulis*) silks using Raman spectroscopy. Biomacromolecules 4 (2), 387-394.

Monti, P. et al., 1998. Raman spectroscopic studies of silk fibroin from *Bombyx mori*. Journal of Raman Spectroscopy 29 (4), 297-304.

Qiu, W. G. et al., 2009. Wet-spinning of recombinant silk-elastin-like protein polymer fibers with high tensile strength and high deformability. Biomacromolecules 10 (3), 602-608.

Motta, A., Fambri, L., Migliaresi, C., 2002. Regenerated silk fibroin films: thermal and dynamic mechanical analysis. Macromolecular Chemistry and Physics 203 (10-11), 1658-1665.

Martin, R. et al., 2000. Liquid crystalline ordering of procollagen as a determinant of three-dimensional extracellular matrix architecture. Journal of Molecular Biology 301 (1), 11-17.

Sohn, S., Strey, H. H., Gido, S. P., 2004. Phase behavior and hydration of silk fibroin. Biomacromolecules 5 (3), 751-757.

Xu, Y. et al., 2005. Solubility and rheological behavior of silk fibroin (*Bombyx mori*) in N-methyl morpholine N-oxide. International Journal of Biological Macromolecules 35 (3-4), 155-161.

Mathiowitz, E. et al., 1999. Bioadhesive Drug Delivery Systems. In: Mathiowitz, E. (Ed.), Encyclopedia of Controlled Drug Delivery. Wiley, New York, pp. 9-45.

Kinloch, A. J., 1980. The science of adhesion. 1. Surface and interfacial aspects. Journal of Materials Science 15 (9), 2141-2166.

Peppas, N. A., Buri, P. A., 1985. Surface, interfacial and molecular aspects of polymer bioadhesion on soft tissues. Journal of Controlled Release 2, 257-275.

Peattie, A. M., 2009. Functional demands of dynamic biological adhesion: an integrative approach. Journal of Comparative Physiology B—Biochemical Systemic and Environmental Physiology 179 (3), 231-239.

What is claimed is:

1. A silk-based gel comprising silk fibroin, wherein the silk fibroin is predominantly in silk I conformation such that the silk-based gel is characterized by material properties selected from the group consisting of adhesive and viscosity properties that allow it to:
   show mechanical response suitable for tissue restoration applications;
   form a coherent stream or material when delivered from a needle;
   fill a tissue void; and/or
   stay in place when applied to a wound, wherein the silk-based gel is capable of reversibly forming a silk fibroin solution.

2. The silk-based gel of claim 1, further comprising at least one active agent.

3. The silk-based gel of claim 1, wherein the silk-based gel is characterized by an adhesive property such that the work of adhesion (WOA) of the silk-based gel to a surface is at least 0.05 mJ.

4. An adhesive composition comprising a silk-based gel of claim 1.

5. A pharmaceutical formulation comprising a silk-based gel of claim 1 and a pharmaceutically acceptable carrier.

6. The pharmaceutical formulation of claim 5, further comprising at least one active agent encapsulated in the silk-based gel.

7. The pharmaceutical formulation of claim 5, wherein the pharmaceutical formulation is an injectable formulation.

8. A method comprising injecting the silk-based gel of claim 1 to a void or crease present in a tissue, thereby filling the void or crease in the tissue with the gel.

* * * * *